(12) United States Patent
Bleich

(10) Patent No.: US 8,613,745 B2
(45) Date of Patent: Dec. 24, 2013

(54) METHODS, SYSTEMS AND DEVICES FOR CARPAL TUNNEL RELEASE

(75) Inventor: Jeffery L. Bleich, Palo Alto, CA (US)

(73) Assignee: Baxano Surgical, Inc., Raleigh, NC (US)

( * ) Notice: Subject to any disclaimer, the term of this patent is extended or adjusted under 35 U.S.C. 154(b) by 334 days.

(21) Appl. No.: 13/112,918

(22) Filed: May 20, 2011

(65) Prior Publication Data

US 2011/0224710 A1 Sep. 15, 2011

Related U.S. Application Data

(63) Continuation-in-part of application No. 11/251,199, filed on Oct. 15, 2005, now Pat. No. 8,192,435, which is a continuation-in-part of application No. 11/429,377, filed on May 4, 2006, now Pat. No. 8,048,080, which is a continuation-in-part of application No. PCT/US2005/037136, filed on Oct. 15, 2005, said application No. 11/429,377 is a continuation-in-part of application No. 11/375,265, filed on Mar. 13, 2006, now Pat. No. 7,887,538, application No. 13/112,918, which is a continuation-in-part of application No. 11/687,548, filed on Mar. 16, 2007, now Pat. No. 8,062,300.

(60) Provisional application No. 60/619,306, filed on Oct. 15, 2004, provisional application No. 60/622,865, filed on Oct. 28, 2004, provisional application No. 60/681,719, filed on May 16, 2005, provisional application No. 60/681,864, filed on May 16, 2005, provisional application No. 60/685,190, filed on May 27, 2005, provisional application No. 60/869,070, filed on Dec. 7, 2006.

(51) Int. Cl.
*A61B 17/00* (2006.01)

(52) U.S. Cl.
USPC ......................................................... 606/79

(58) Field of Classification Search
USPC ............ 606/79, 85, 103, 110, 119, 131, 163, 606/171–176, 167
See application file for complete search history.

(56) References Cited

U.S. PATENT DOCUMENTS 184,804 A  11/1876  Stohlmann
(Continued)

FOREIGN PATENT DOCUMENTS

DE  3209403 A1  9/1983
DE  4036804 A1  5/1992
(Continued)

OTHER PUBLICATIONS

Arcenio et al.; U.S. Appl. No. 12/980,165 entitled "Systems and Methods for Performing Spinal Fusion", filed Dec. 28, 2010.

(Continued)

*Primary Examiner* — Sameh Boles
(74) *Attorney, Agent, or Firm* — Shay Glenn LLP

(57) ABSTRACT

Described herein are methods, systems, and devices for performing a minimally invasive carpal tunnel release procedure to cut a target transverse carpal ligament. In some embodiments, the method may include the steps of advancing a probe percutaneously though a patient's skin from a first location, advancing a tissue modification device from the first location and between the target ligament and non-target tissue so that a proximal handle on the tissue modification device extends from the patient at the first location, attaching a distal handle in communication with the distal end of the tissue modification device. In some embodiments, a system may include a probe configured to be advanced percutaneously though a patient's skin from a first location, a tissue modification device comprising a proximal handle and a flexible distal region having uni-directional blades, and a distal handle configured to connect to the distal end of the tissue modification device.

12 Claims, 47 Drawing Sheets

(56) References Cited

U.S. PATENT DOCUMENTS

| | | |
|---|---|---|
| 289,104 A | 11/1883 | How |
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al |
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,200,814 A | 8/1965 | Taylor et al. |
| 3,214,824 A | 11/1965 | Brown |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,123,400 A | 6/1992 | Edgerton |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,591,170 A | 1/1997 | Spievack et al. |
| 5,598,848 A | 2/1997 | Swanson et al. |
| 5,620,447 A | 4/1997 | Smith et al. |

(56) References Cited

U.S. PATENT DOCUMENTS

| | | |
|---|---|---|
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A | 7/1998 | Raymond et al. |
| 5,779,642 A | 7/1998 | Nightengale |
| 5,788,653 A | 8/1998 | Lorenzo |
| 5,792,044 A | 8/1998 | Foley et al. |
| 5,795,308 A | 8/1998 | Russin |
| 5,800,350 A | 9/1998 | Coppleson et al. |
| 5,803,902 A | 9/1998 | Sienkiewicz et al. |
| 5,803,904 A | 9/1998 | Mehdizadeh |
| 5,807,263 A | 9/1998 | Chance |
| 5,810,744 A | 9/1998 | Chu et al. |
| 5,813,405 A | 9/1998 | Montano, Jr. et al. |
| 5,824,040 A | 10/1998 | Cox et al. |
| 5,830,151 A | 11/1998 | Hadzic et al. |
| 5,830,157 A | 11/1998 | Foote |
| 5,830,188 A | 11/1998 | Abouleish |
| 5,833,692 A | 11/1998 | Cesarini et al. |
| 5,836,810 A | 11/1998 | Åsum |
| 5,836,948 A | 11/1998 | Zucherman et al. |
| 5,843,110 A | 12/1998 | Dross et al. |
| 5,846,196 A | 12/1998 | Siekmeyer et al. |
| 5,846,244 A | 12/1998 | Cripe |
| 5,851,191 A | 12/1998 | Gozani |
| 5,851,209 A | 12/1998 | Kummer et al. |
| 5,851,214 A | 12/1998 | Larsen et al. |
| 5,853,373 A | 12/1998 | Griffith et al. |
| 5,865,844 A | 2/1999 | Plaia et al. |
| 5,868,767 A | 2/1999 | Farley et al. |
| 5,879,353 A | 3/1999 | Terry |
| 5,885,219 A | 3/1999 | Nightengale |
| 5,895,417 A | 4/1999 | Pomeranz et al. |
| 5,897,583 A | 4/1999 | Meyer et al. |
| 5,899,909 A | 5/1999 | Claren et al. |
| 5,904,657 A | 5/1999 | Unsworth et al. |
| 5,916,173 A | 6/1999 | Kirsner |
| 5,918,604 A | 7/1999 | Whelan |
| 5,919,190 A | 7/1999 | VanDusseldorp |
| 5,928,158 A | 7/1999 | Aristides |
| 5,928,159 A | 7/1999 | Eggers et al. |
| 5,941,822 A | 8/1999 | Skladnev et al. |
| 5,961,522 A | 10/1999 | Mehdizadeh |
| 5,972,013 A | 10/1999 | Schmidt |
| 5,976,110 A | 11/1999 | Greengrass et al. |
| 5,976,146 A | 11/1999 | Ogawa et al. |
| 6,002,964 A | 12/1999 | Feler et al. |
| 6,004,326 A | 12/1999 | Castro et al. |
| 6,004,330 A | 12/1999 | Middleman et al. |
| 6,010,493 A | 1/2000 | Snoke |
| 6,015,406 A | 1/2000 | Goble et al. |
| 6,022,362 A | 2/2000 | Lee et al. |
| 6,030,383 A | 2/2000 | Benderev |
| 6,030,401 A | 2/2000 | Marino |
| 6,038,480 A | 3/2000 | Hrdlicka et al. |
| 6,048,345 A | 4/2000 | Berke et al. |
| 6,068,642 A | 5/2000 | Johnson et al. |
| 6,073,051 A | 6/2000 | Sharkey et al. |
| 6,099,514 A | 8/2000 | Sharkey et al. |
| 6,102,930 A | 8/2000 | Simmons, Jr. |
| 6,106,558 A | 8/2000 | Picha |
| 6,113,534 A | 9/2000 | Koros et al. |
| D432,384 S | 10/2000 | Simons |
| 6,132,387 A | 10/2000 | Gozani et al. |
| 6,136,014 A | 10/2000 | Sirimanne et al. |
| 6,142,993 A | 11/2000 | Whayne et al. |
| 6,142,994 A | 11/2000 | Swanson et al. |
| 6,146,380 A | 11/2000 | Racz et al. |
| 6,152,894 A | 11/2000 | Kubler |
| 6,169,916 B1 | 1/2001 | West |
| 6,205,360 B1 | 3/2001 | Carter et al. |
| 6,214,001 B1 | 4/2001 | Casscells et al. |
| 6,214,016 B1 | 4/2001 | Williams et al. |
| 6,236,892 B1 | 5/2001 | Feler |
| 6,251,115 B1 | 6/2001 | Williams et al. |
| 6,256,540 B1 | 7/2001 | Panescu et al. |
| 6,259,945 B1 | 7/2001 | Epstein et al. |
| 6,261,582 B1 | 7/2001 | Needham et al. |
| 6,266,551 B1 | 7/2001 | Osadchy et al. |
| 6,266,558 B1 | 7/2001 | Gozani et al. |
| 6,267,760 B1 | 7/2001 | Swanson |
| 6,272,367 B1 | 8/2001 | Chance |
| 6,277,094 B1 | 8/2001 | Schendel |
| 6,280,447 B1 | 8/2001 | Marino et al. |
| 6,292,702 B1 | 9/2001 | King et al. |
| 6,298,256 B1 | 10/2001 | Meyer |
| 6,312,392 B1 | 11/2001 | Herzon |
| 6,324,418 B1 | 11/2001 | Crowley et al. |
| 6,324,432 B1 | 11/2001 | Rigaux et al. |
| 6,325,764 B1 | 12/2001 | Griffith et al. |
| 6,334,068 B1 | 12/2001 | Hacker |
| 6,343,226 B1 | 1/2002 | Sunde et al. |
| 6,358,254 B1 | 3/2002 | Anderson |
| 6,360,750 B1 | 3/2002 | Gerber et al. |
| 6,364,886 B1 | 4/2002 | Sklar |
| 6,368,324 B1 | 4/2002 | Dinger et al. |
| 6,370,411 B1 | 4/2002 | Osadchy et al. |
| 6,370,435 B2 | 4/2002 | Panescu et al. |
| 6,383,509 B1 | 5/2002 | Donovan et al. |
| 6,390,906 B1 | 5/2002 | Subramanian |
| 6,391,028 B1 | 5/2002 | Fanton et al. |
| 6,416,505 B1 | 7/2002 | Fleischman et al. |
| 6,423,071 B1 | 7/2002 | Lawson |
| 6,423,080 B1 | 7/2002 | Gellman et al. |
| 6,425,859 B1 | 7/2002 | Foley et al. |
| 6,425,887 B1 | 7/2002 | McGuckin et al. |
| 6,428,486 B2 | 8/2002 | Ritchart et al. |
| 6,436,101 B1 | 8/2002 | Hamada |
| 6,442,848 B1 | 9/2002 | Dean |
| 6,446,621 B1 | 9/2002 | Svensson |
| 6,451,335 B1 | 9/2002 | Goldenheim et al. |
| 6,454,767 B2 | 9/2002 | Alleyne |
| 6,464,682 B1 | 10/2002 | Snoke |
| 6,466,817 B1 | 10/2002 | Kaula et al. |
| 6,468,289 B1 | 10/2002 | Bonutti |
| 6,470,209 B2 | 10/2002 | Snoke |
| 6,478,805 B1 | 11/2002 | Marino et al. |
| 6,487,439 B1 | 11/2002 | Skladnev et al. |
| 6,488,636 B2 | 12/2002 | Bryan et al. |
| 6,491,646 B1 | 12/2002 | Blackledge |
| 6,500,128 B2 | 12/2002 | Marino |
| 6,500,189 B1 | 12/2002 | Lang et al. |
| 6,512,958 B1 | 1/2003 | Swoyer et al. |
| 6,516,223 B2 | 2/2003 | Hofmann |
| 6,520,907 B1 | 2/2003 | Foley et al. |
| 6,527,786 B1 | 3/2003 | Davis et al. |
| 6,533,749 B1 | 3/2003 | Mitusina et al. |
| 6,535,759 B1 | 3/2003 | Epstein et al. |
| 6,540,742 B1 | 4/2003 | Thomas et al. |
| 6,540,761 B2 | 4/2003 | Houser |
| 6,546,270 B1 | 4/2003 | Goldin et al. |
| 6,558,353 B2 | 5/2003 | Zohmann |
| 6,558,390 B2 | 5/2003 | Cragg |
| 6,562,033 B2 | 5/2003 | Shah et al. |
| 6,564,078 B1 | 5/2003 | Marino et al. |
| 6,564,079 B1 | 5/2003 | Cory et al. |
| 6,564,088 B1 | 5/2003 | Soller et al. |
| 6,569,160 B1 | 5/2003 | Goldin et al. |
| 6,575,979 B1 | 6/2003 | Cragg |
| 6,579,291 B1 | 6/2003 | Keith et al. |
| 6,584,345 B2 | 6/2003 | Govari |

(56) References Cited

U.S. PATENT DOCUMENTS

| | | |
|---|---|---|
| 6,592,559 B1 | 7/2003 | Pakter et al. |
| 6,595,932 B2 | 7/2003 | Ferrera |
| 6,597,955 B2 | 7/2003 | Panescu et al. |
| 6,606,523 B1 | 8/2003 | Jenkins |
| 6,607,530 B1 | 8/2003 | Carl et al. |
| 6,609,018 B2 | 8/2003 | Cory et al. |
| 6,610,066 B2 | 8/2003 | Dinger et al. |
| 6,620,129 B2 | 9/2003 | Stecker et al. |
| 6,622,731 B2 | 9/2003 | Daniel et al. |
| 6,624,510 B1 | 9/2003 | Chan et al. |
| 6,626,916 B1 | 9/2003 | Yeung et al. |
| 6,632,184 B1 | 10/2003 | Truwit |
| 6,638,233 B2 | 10/2003 | Corvi et al. |
| RE38,335 E | 11/2003 | Aust et al. |
| 6,648,883 B2 | 11/2003 | Francischelli et al. |
| 6,666,874 B2 | 12/2003 | Heitzmann et al. |
| 6,673,063 B2 | 1/2004 | Brett |
| 6,673,068 B1 | 1/2004 | Berube |
| 6,678,552 B2 | 1/2004 | Pearlman |
| 6,682,535 B2 | 1/2004 | Hoogland |
| 6,682,536 B2 | 1/2004 | Vardi et al. |
| 6,685,709 B2 | 2/2004 | Sklar |
| 6,699,246 B2 | 3/2004 | Zucherman et al. |
| 6,723,049 B2 | 4/2004 | Skladnev et al. |
| 6,726,531 B1 | 4/2004 | Harrel |
| 6,726,685 B2 | 4/2004 | To et al. |
| 6,733,496 B2 | 5/2004 | Sharkey et al. |
| 6,736,815 B2 | 5/2004 | Ginn |
| 6,736,835 B2 | 5/2004 | Pellegrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,764,491 B2 | 7/2004 | Frey et al. |
| 6,772,012 B2 | 8/2004 | Ricart et al. |
| 6,776,765 B2 | 8/2004 | Soukup et al. |
| 6,786,876 B2 | 9/2004 | Cox |
| 6,788,966 B2 | 9/2004 | Kenan et al. |
| 6,790,210 B1 | 9/2004 | Cragg et al. |
| 6,795,737 B2 | 9/2004 | Gielen et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,895,283 B2 | 5/2005 | Erickson et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,953,461 B2 | 10/2005 | McClurken et al. |
| 6,962,587 B2 | 11/2005 | Johnson et al. |
| 6,969,392 B2 | 11/2005 | Gitis et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,069,083 B2 | 6/2006 | Finch et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,172,562 B2 | 2/2007 | McKinley |
| 7,177,677 B2 | 2/2007 | Kaula et al. |
| 7,181,289 B2 | 2/2007 | Pflueger et al. |
| 7,189,240 B1 | 3/2007 | Dekel |
| 7,192,430 B2 | 3/2007 | Truckai et al. |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al |
| 7,214,186 B2 | 5/2007 | Ritland |
| 7,214,197 B2 | 5/2007 | Prass |
| 7,216,001 B2 | 5/2007 | Hacker et al. |
| 7,223,278 B2 | 5/2007 | Davison et al. |
| 7,236,832 B2 | 6/2007 | Hemmerling et al. |
| 7,238,189 B2 | 7/2007 | Schmieding et al. |
| 7,239,911 B2 | 7/2007 | Scholz |
| 7,245,789 B2 | 7/2007 | Bates et al. |
| 7,270,658 B2 | 9/2007 | Woloszko et al. |
| 7,270,659 B2 | 9/2007 | Ricart et al. |
| 7,282,033 B2 | 10/2007 | Urmey |
| 7,282,061 B2 | 10/2007 | Sharkey et al. |
| 7,295,881 B2 | 11/2007 | Cohen et al. |
| 7,318,823 B2 | 1/2008 | Sharps et al. |
| 7,337,005 B2 | 2/2008 | Kim et al. |
| 7,337,006 B2 | 2/2008 | Kim et al. |
| 7,367,972 B2 | 5/2008 | Francischelli et al. |
| 7,383,639 B2 | 6/2008 | Malandain |
| 7,390,330 B2 | 6/2008 | Harp |
| 7,419,487 B2 | 9/2008 | Johnson et al. |
| 7,449,019 B2 | 11/2008 | Uchida et al. |
| 7,452,351 B2 | 11/2008 | Miller et al. |
| 7,470,236 B1 | 12/2008 | Kelleher et al. |
| 7,476,226 B2 | 1/2009 | Weikel et al. |
| 7,494,473 B2 | 2/2009 | Eggers et al. |
| 7,500,977 B2 | 3/2009 | Assell et al. |
| 7,503,920 B2 | 3/2009 | Siegal |
| 7,507,218 B2 | 3/2009 | Aliski et al. |
| 7,522,953 B2 | 4/2009 | Gharib et al. |
| 7,553,307 B2 | 6/2009 | Bleich et al. |
| 7,555,343 B2 | 6/2009 | Bleich |
| 7,578,819 B2 | 8/2009 | Bleich et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,738,968 B2 | 6/2010 | Bleich |
| 7,738,969 B2 | 6/2010 | Bleich |
| 7,740,631 B2 | 6/2010 | Bleich et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |

(56) References Cited

U.S. PATENT DOCUMENTS

| | | | |
|---|---|---|---|
| 8,366,712 B2 | 2/2013 | Bleich et al. |
| 8,398,641 B2 | 3/2013 | Wallace et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2002/0022788 A1 | 2/2002 | Corvi et al. |
| 2002/0029060 A1 | 3/2002 | Hogendijk |
| 2002/0106681 A1 | 8/2002 | Wexler et al. |
| 2002/0138091 A1 | 9/2002 | Pflueger |
| 2002/0165590 A1 | 11/2002 | Crowe et al. |
| 2002/0183647 A1 | 12/2002 | Gozani et al. |
| 2003/0015203 A1 | 1/2003 | Makower et al. |
| 2003/0074037 A1 | 4/2003 | Moore et al. |
| 2003/0105503 A1 | 6/2003 | Marino |
| 2003/0113906 A1 | 6/2003 | Sangha et al. |
| 2003/0130655 A1 | 7/2003 | Woloszko et al. |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0030330 A1 | 2/2004 | Brassell et al. |
| 2004/0049208 A1 | 3/2004 | Hill et al. |
| 2004/0059260 A1 | 3/2004 | Truwit |
| 2004/0064058 A1 | 4/2004 | McKay |
| 2004/0097927 A1 | 5/2004 | Yeung et al. |
| 2004/0106940 A1 | 6/2004 | Shaolian et al. |
| 2004/0111084 A1 | 6/2004 | Brett |
| 2004/0122433 A1 | 6/2004 | Loubens et al. |
| 2004/0122459 A1* | 6/2004 | Harp ........................ 606/171 |
| 2004/0122482 A1 | 6/2004 | Tung et al. |
| 2004/0127893 A1 | 7/2004 | Hovda |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199159 A1 | 10/2004 | Lee et al. |
| 2004/0220576 A1 | 11/2004 | Sklar |
| 2004/0225233 A1 | 11/2004 | Frankowski et al. |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0149035 A1 | 7/2005 | Pimenta et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1 | 10/2005 | Wahlstrand et al. |
| 2005/0256423 A1 | 11/2005 | Kirsner |
| 2005/0261692 A1 | 11/2005 | Carrison et al. |
| 2005/0267529 A1 | 12/2005 | Crockett et al. |
| 2005/0277942 A1 | 12/2005 | Kullas et al. |
| 2005/0283148 A1 | 12/2005 | Janssen et al. |
| 2005/0283204 A1 | 12/2005 | Buhlmann et al. |
| 2006/0004369 A1 | 1/2006 | Patel et al. |
| 2006/0015035 A1 | 1/2006 | Rock |
| 2006/0025702 A1 | 2/2006 | Sterratino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089650 A1 | 4/2006 | Nolde |
| 2006/0089688 A1 | 4/2006 | Panescu |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0264952 A1 | 11/2006 | Nelson et al. |
| 2006/0264994 A1 | 11/2006 | Schomer et al. |
| 2006/0271080 A1 | 11/2006 | Suddaby |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123766 A1 | 5/2007 | Whalen, III et al. |
| 2007/0123888 A1 | 5/2007 | Bleich et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213733 A1 | 9/2007 | Bleich et al. |
| 2007/0213734 A1 | 9/2007 | Bleich et al. |
| 2007/0213795 A1 | 9/2007 | Bradley et al. |
| 2007/0225703 A1 | 9/2007 | Schmitz et al. |
| 2007/0255162 A1 | 11/2007 | Abboud et al. |
| 2007/0255369 A1 | 11/2007 | Bonde et al. |
| 2007/0260252 A1 | 11/2007 | Schmitz et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0293782 A1 | 12/2007 | Marino |
| 2007/0299403 A1 | 12/2007 | Crowe et al. |
| 2007/0299459 A1 | 12/2007 | Way et al. |
| 2008/0033465 A1 | 2/2008 | Schmitz et al. |
| 2008/0051812 A1 | 2/2008 | Schmitz et al. |

(56) References Cited

U.S. PATENT DOCUMENTS

| | | |
|---|---|---|
| 2008/0058820 A1 | 3/2008 | Harp |
| 2008/0058874 A1 | 3/2008 | Westlund et al. |
| 2008/0064945 A1 | 3/2008 | Marino et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0086034 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0197024 A1 | 8/2008 | Simpson et al. |
| 2008/0200912 A1 | 8/2008 | Long |
| 2008/0221383 A1 | 9/2008 | Way et al. |
| 2008/0221586 A1 | 9/2008 | Garcia-Bengochea et al. |
| 2008/0255439 A1 | 10/2008 | Tang et al. |
| 2008/0275458 A1 | 11/2008 | Bleich et al. |
| 2008/0288005 A1 | 11/2008 | Jackson |
| 2008/0312660 A1 | 12/2008 | Bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0036936 A1 | 2/2009 | Solsberg et al. |
| 2009/0054804 A1 | 2/2009 | Gharib et al. |
| 2009/0054936 A1 | 2/2009 | Eggen et al. |
| 2009/0054941 A1 | 2/2009 | Eggen et al. |
| 2009/0062871 A1 | 3/2009 | Chin et al. |
| 2009/0062872 A1 | 3/2009 | Chin et al. |
| 2009/0069709 A1 | 3/2009 | Schmitz et al. |
| 2009/0082763 A1 | 3/2009 | Quick et al. |
| 2009/0105604 A1 | 4/2009 | Bertagnoli et al. |
| 2009/0105788 A1 | 4/2009 | Bartol et al. |
| 2009/0118709 A1 | 5/2009 | Sand et al. |
| 2009/0124934 A1 | 5/2009 | Rabbitte et al. |
| 2009/0138056 A1 | 5/2009 | Anderson et al. |
| 2009/0143807 A1 | 6/2009 | Sand |
| 2009/0143829 A1 | 6/2009 | Shluzas |
| 2009/0149865 A1 | 6/2009 | Schmitz et al. |
| 2009/0171381 A1 | 7/2009 | Schmitz et al. |
| 2009/0177112 A1 | 7/2009 | Gharib et al. |
| 2009/0177144 A1 | 7/2009 | Masmanidis et al. |
| 2009/0177241 A1 | 7/2009 | Bleich et al. |
| 2009/0182382 A1 | 7/2009 | Justis et al. |
| 2009/0192403 A1 | 7/2009 | Gharib et al. |
| 2009/0204016 A1 | 8/2009 | Gharib et al. |
| 2009/0204119 A1 | 8/2009 | Bleich et al. |
| 2009/0209879 A1 | 8/2009 | Kaula et al. |
| 2009/0216284 A1 | 8/2009 | Chin et al. |
| 2009/0299166 A1 | 12/2009 | Nishida et al. |
| 2010/0004654 A1 | 1/2010 | Schmitz et al. |
| 2010/0010334 A1 | 1/2010 | Bleich et al. |
| 2010/0057087 A1 | 3/2010 | Cha |
| 2010/0094231 A1 | 4/2010 | Bleich et al. |
| 2010/0274250 A1 | 10/2010 | Wallace et al. |
| 2010/0331883 A1 | 12/2010 | Schmitz et al. |
| 2010/0331900 A1 | 12/2010 | Garabedian et al. |
| 2011/0004207 A1 | 1/2011 | Wallace et al. |
| 2011/0046613 A1 | 2/2011 | Schmitz et al. |
| 2011/0060314 A1 | 3/2011 | Wallace et al. |
| 2011/0112539 A1 | 5/2011 | Wallace et al. |
| 2011/0224709 A1 | 9/2011 | Bleich |
| 2012/0016368 A1 | 1/2012 | Bleich et al. |
| 2012/0022538 A1 | 1/2012 | Schmitz et al. |
| 2012/0065639 A1 | 3/2012 | Schmitz et al. |
| 2012/0123294 A1 | 5/2012 | Sun et al. |
| 2012/0143206 A1 | 6/2012 | Wallace et al. |
| 2012/0184809 A1 | 7/2012 | Bleich et al. |
| 2012/0191003 A1 | 7/2012 | Garabedian et al. |
| 2012/0239041 A1 | 9/2012 | Bleich et al. |
| 2013/0012831 A1 | 1/2013 | Schmitz et al. |
| 2013/0053851 A1 | 2/2013 | Schmitz et al. |
| 2013/0053853 A1 | 2/2013 | Schmitz et al. |
| 2013/0150855 A1 | 6/2013 | Bleich et al. |
| 2013/0150856 A1 | 6/2013 | Mimran et al. |
| 2013/0172895 A1 | 7/2013 | Wallace et al. |

FOREIGN PATENT DOCUMENTS

| | | |
|---|---|---|
| EP | 359883 A1 | 9/1983 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| JP | 2960140 B2 | 10/1999 |
| JP | 23116868 | 4/2003 |
| JP | 24065380 A2 | 3/2004 |
| RU | 2107459 | 3/1998 |
| WO | WO92/22259 A2 | 12/1992 |
| WO | WO-96/22057 | 7/1996 |
| WO | WO97/14362 A1 | 4/1997 |
| WO | WO-97/34536 A | 9/1997 |
| WO | WO-99/18866 A1 | 4/1999 |
| WO | WO-99/21500 A1 | 5/1999 |
| WO | WO-00/67651 A1 | 11/2000 |
| WO | WO-01/08571 A1 | 2/2001 |
| WO | WO-01/62168 A2 | 8/2001 |
| WO | WO-02/07901 A1 | 1/2002 |
| WO | WO-02/34120 A2 | 5/2002 |
| WO | WO-02/076311 A2 | 10/2002 |
| WO | WO-03/026482 A2 | 4/2003 |
| WO | WO-03/066147 A1 | 8/2003 |
| WO | WO-2004/002331 A1 | 1/2004 |
| WO | WO-2004/028351 A2 | 4/2004 |
| WO | WO-2004/043272 A1 | 5/2004 |
| WO | WO-2004/056267 A1 | 7/2004 |
| WO | WO-2004/078066 A2 | 9/2004 |
| WO | WO-2004/080316 A1 | 9/2004 |
| WO | WO-2004/096080 A2 | 11/2004 |
| WO | WO-2005/009300 A1 | 2/2005 |
| WO | WO-2005/057467 A2 | 6/2005 |
| WO | WO-2005/077282 A1 | 8/2005 |
| WO | WO-2005/089433 A2 | 9/2005 |
| WO | WO-2006/009705 A2 | 1/2006 |
| WO | WO-2006/015302 A1 | 2/2006 |
| WO | WO-2006/017507 A2 | 2/2006 |
| WO | WO-2006/039279 A2 | 4/2006 |
| WO | WO-2006/042206 A2 | 4/2006 |
| WO | WO-2006/044727 A2 | 4/2006 |
| WO | WO-2006/047598 A1 | 5/2006 |
| WO | WO-2006/058079 A3 | 6/2006 |
| WO | WO-2006/058195 A2 | 6/2006 |
| WO | WO-2006/062555 A2 | 6/2006 |
| WO | WO-2006/086241 A2 | 8/2006 |
| WO | WO-2006/099285 A2 | 9/2006 |
| WO | WO-2006/102085 A2 | 9/2006 |
| WO | WO-2007/008709 A2 | 1/2007 |
| WO | WO-2007/021588 A1 | 2/2007 |
| WO | WO-2007/022194 A2 | 2/2007 |
| WO | WO-2007/059343 A2 | 2/2007 |
| WO | WO-2007/067632 A2 | 6/2007 |
| WO | WO-2008/008898 A2 | 1/2008 |
| WO | WO-2008/157513 A1 | 12/2008 |
| WO | WO-2009/012265 A2 | 1/2009 |
| WO | WO-2009/018220 A1 | 2/2009 |
| WO | WO-2009/021116 A2 | 2/2009 |
| WO | WO-2009/036156 A1 | 3/2009 |
| WO | WO-2009/046046 A1 | 4/2009 |
| WO | WO-2009/058566 A1 | 5/2009 |

(56) References Cited

FOREIGN PATENT DOCUMENTS

| WO | WO-2009/151926 A2 | 12/2009 |
|---|---|---|
| WO | WO-2010/014538 | 4/2010 |

OTHER PUBLICATIONS

Bleich et al.; U.S. Appl. No. 12/984,162 entitled "Devices and Methods for Tissue Access", filed Jan. 4, 2011.
Saadt et al.: U.S. Appl. No. 13/078,376 entitled "Powered Tissue Modification Devices and Methods", filed Apr. 1, 2011.
Schmitz et al.; U.S. Appl. No. 13/090,944 entitled "Method, System and Apparatus for Neural Localization", filed Apr. 20, 2011.
US Surgical Kerrison Spinal Rongeur K943116 [online] Retrieved from the internet: <URL: http://www.ussurg.com/uss/inex.html>. Jul. 27, 1994.
Edwards et al.; "T-Saw Laminoplasty for the Management of Cervical Spondylotic Myelopathy," SPINE, Lippincott Williams & Wilkins, Inc., 2000, vol. 25 (14): 1788-1794. Jan. 1, 2000.
Honl et al.; "The Use of Water-Jetting Technology in Protheses Revision Surgery—First Results of Parameter Studies on Bone and Bone Cement," J. Biomed Mater Res (Applied Biomaterials), John Wiley & Sons, Inc, 2000, 53, 6: 781-790. Jan. 1, 2000.
Jun Byung-Yoon, "Posterior Lumbar Interbody Fusion With Restoration of Lamina and Facet Fusion ," SPINE, Lippincott Williams & Wilkins, Inc., 2000. vol. 25, No. 8, 917-922. Jan. 1, 2000.
Abdel-Wanis et al., "Tumor growth potential after tumoral and instrument contamination: an in-vivo comparative study of T-saw, Gigli saw, and scalpel," Journal of orthopaedic science, 2001, vol. 48, No. 1, pp. 235-239. Jan. 1, 2001.
Hara et al., "En Bloc Laminoplasty Performed with Threadwire Saw: Technical Note." Neurosurgery. Jan. 2001, vol. 48, No. 1, 99. 235-239. Jan. 1, 2001.
Hata et al., "A less invasive surgery for rotator cuff tear: Mini-open repair," Journal of Shoulder and Elbow Surgery, 2001, vol. 10, No. 1, 11-16. Jan. 1, 2001.
Sen, Cengiz, Tibia proksimalinde Gigli testeresi ile yapilanperkütan osteotominin güvenilirligi Kadavra callsmasi. Acta orthopaedica et traumatologica turcica, 2002, vol. 36, 136-140; (In Russian w/ Eng Summary). Jan. 1, 2002.
Shiraishi T., "A new technique for exposure of the cervical spin laminae," Journal of neurosurgery, Spine, 2002, vol. 96 (1), 122-126, Jan. 1, 2002.
Shiraishi T., Skip laminectomy—a new treatment for cervical spondylotic myelopathy, preserving bilateral muscular attachments to the spinous processes: a preliminary report. Spine, 2002, vol 2(2), 108-115. Jan. 1, 2002.
Tomita et al., "The Use of the T-Saw for Expansive Midline laminoplasty in the Treatment of Cervical Myelopathy," Orthopedics and Traumatology, No. 3, pp. 169-178, 2002 Jan. 1, 2002.
Martin-Benlloch et al. "Expansive Laminoplasty as a Method for Managing Cervical Multilevel Spondylotic Myelopathy," Spine, Lippinott Williams & Wilkins, Inc., 2003, vol. 28, No. 7, 680-684, Jan. 1, 2003.
Miyamoto et al., "Kyphectomy Using a Surgical Threadwire (T-saw) for Kyphotic Deformity in a Child With Myelomeningocels," SPINE, Lippincott Williams & Wilkins, Inc., 2003, vol. 28 No. 10, E187-E190. Jan. 1, 2003.
Shiraishi et al., "Results of Skip Laminectomy—Minimum 2-Year Follow-up Study Compared With Open-Door Laminoplasty," Spine, Lippincott Williams & Wilkins, Inc., 2003, vol. 28 No. 24, 2667-2672, Jan. 1, 2003.
Takada et al., "Unusual Metastasis to the Cauda Equina From Renal Cell Carcinoma," SPINE, Lippincott Williams & Wilkins, Inc., 2003, vol. 28 No. 6, E114-E117. Jan. 1, 2004.
Eralp et al., "A comparison of two osteotomy techniques for tibial lengthening," Archives of orthopaedic and trauma surgery, 2004, vol. 124:298-300, Jan. 1, 2003.
Skippen et al., "The Chain Saw—A Scottish Invention," Scottish Medical Journal, 2004, vol. 49(2), 72-75. Jan. 1, 2004.
Bohinski et al., "Novel use of a threadwire saw for high sacral amputation," Journal of neirosurgery: Spine, 2005, vol. 3, 71-78, Jan. 1, 2005.
Nakagiri et al., "Thoracoscopic Rib Resection Using a Gigli Saw," The Annals of Thoracic Surgery, 2005, vol. 80, 755-756. Jan. 1, 2005.
Osaka et al., "Clinical Significance of a wide excision policy for sacrococcygeal chordoma," J Cancer Res Clin Oncol, 2005, Total pp. 6. Jan. 1, 2005.
Fessler Richard G, "Minimally Invasive Microendoscopic Decompressive Laminotomy for Lumbar Stenosis," American Association of Neurological Surgeons, 2006, Online CME course, [Retrieved on Jun. 29, 2006] from the internet http://www.aans.emedtrain.com/lumbar_ste Jan. 1, 2006.
Park et al., "Cases of the Excision of Carious Joints," John Scrymgeour Glasgow, 1806, Total pp. 6. Jan. 1, 1806.
Pancoast, Joseph, "A Treatise on Operative Surgery," Carey and Hart, Philadelphia, 1844, Total pp. 11, Jan. 1, 1844.
Truax, Charles, "The Mechanics of Surgery," Chicago, IL; 1899, Total pp. 3. Jan. 1, 1899.
Burrows, Harold. "Surgical instruments and appliances used in operations," Faber and Faber, London, 1937, total pp. 4, Jan. 1, 1937.
Wilkins, Robert H. "Neurosurgical Classics," Johnson Reprint Coporation, New York, 1965, 377-382. Jan. 1, 1965.
Dammann, Gordon, Pictorial Encyclopedia of Civil War Medical Instruments and Equipment, Pictorial Histories Publishing Company, Missoula, Montana, 1983, Total pp. 2. Jan. 1, 1983.
Barer Malvin, "Instrument to Enhance Passage of the Gigli Saw," Journal of Pediatric Orthopedics, Raven Press, New York, 1984, 4:762-763. Jan. 1, 1984.
Paley et al., "Percutaneous Osteotomies," Orthopedic Clinics of North America, 1991, vol. 22, No. 4, 613-624, Jan. 1, 1993.
Paktiss et al., "Afghan Percutaneous Osteotomy," Journal of Pediatric Orthopaedics, Raven Press Ltd, New York, 1993, vol. 13 No. 4, 531-533. Jan. 1, 1993.
Peltier, Leonardo Orthopedic: A History and Iconography, Norman Publishing, San Francisco, 1993, Total pp. 3. Jan. 1, 1993.
Rutkow, Ira, "Surgery an Illustrated History," Mosby—Year Book, Inc., St. Louis, 1993, Total pp. 4, Jan. 1, 1993.
Goel, Atul, "Neurosurgrical forum, Supraorbital Craniotomy," Journal of Neurosurgery, 1994, vol. 81, 642-643, Jan. 1, 1994.
Tomita et al., "Total en bloc spondylectomy and circumspinal decompression for solitary spinal metastasis," Paraplegia, 1994, 32: 36-46. Jan. 1, 1994.
Tomita K. et al., "Total en bloc spondylectomy for solitary spinal metastases," International Orthopaedics (SICOT), 1994, 18: 291-298. Jan. 1, 1994.
Brunori et al., "Celebrating the centennial (1894-1994): Leonardo Gigli and his wire saw," J Neurosurg, 1995, 82:1086-1090, Jan. 1, 1995.
Tomita et al., "The Threadwire Saw: a New Device for Cutting Bone," The Journal of Bone and Joint Surgery, 1996, vol. 78, 1915-1917, Jan. 1, 1998.
Baumgart et al., "Indikation and Technik der Knochendurchtrennung," Der Chirurg, 1998, vol. 69: 1188-1196. (in German with Eng Summary). Jan. 1, 1998.
Stevens et al., "Calvarial Bone Graft Harvest Using the Gigli Saw," Journal of Oral and Maxilofacial Surgery, 1998, vol. 56, 798-799. Jan. 1, 1998.
Tomita et al., "Expansive Midline T-Saw Laminoplasty (Modified Spinour Process-Splitting) for the Management of Cervical Myelopathy," SPINE, Lippincott Williams & Wilkins, Inc, 1998, 23(1), 32-37. Jan. 1, 1998.
Fujita et al.: "Chorderna in the. Cervicai Spine Managed vvile En Bloc Excision," Spine, Lippincott Williams & Wilkins, Inc., 1999, 24(17), 1848-1851. Jan. 1, 1999.
Gore Smoother User Manual, W.L. Gore & Associates, Inc. Flagstaff, AZ, Dec. 1999, Total pp. 3. Jan. 1, 1999.
Kawahara et al., "Recapping T-Saw Laminoplasty for Spinel Cord Turnore." SPINE, 1999. vol. 24 No. 13 pp. 1363-1370. Jan. 1, 1999.

(56) References Cited

OTHER PUBLICATIONS

Peavy et ei., "Comparison of Cortical Bane Ablations by Using Infrared Laser Wavelengths 2.9 to 9.2 µm, Lasers in Surgery and: Medicine," 1999. vol. 26, 421-434. Jan. 1, 1999.

Zeppelin Laminectomy Rongeur K901372, [online] Retrieved from the internet: <URL:http://www.zeppelin-medical.com/download/instruments.pdf>, Oct. 24, 2006.

Reckling Frederick; "Modified Stethoscope Earpiece Makes Excellent Gigli Saw Guide," J Bone and Joint Surgery Am, Dec. 1972, 54-A(8), 1787-1788. Dec. 1, 1972.

Ellman Int Disc-FX System Accessories K052241 [oniine] Retrieved from the Internet: <URL: http://www.ellman.com/medical/>. Feb. 27, 2006.

Bartol et al., "Arthoroscopio Microscopic Discectomy in Awake Patients: The Effectiveness of Local/Neurolept Anaesthetic," Canadian Spine Society Meeting, Vernon BC, Canada, Mar. 2002. 2002.

Bartol et el., "Use of Neve Stimulator to Localise the Spinal Nerce Root During Arthroscopic Discectomy Precedores," Canadian Spine Society Meeting, Vernon BC, Canada Mar. 2002. 2002.

Ohta at at, "Superimposed Mechanomygraphic Response at Different Contraction Intensity in Medial Gastronemius and Soleus Muscles" International journal of Sport and Health Science: vol. 5; 63-70; 2007. 2007.

Schwieger et al., "Abrasive Water Jet Cutting as a New Procedure for Cutting Cancellous Bona—In Vitro Testing in Comparison with the Oscillating Saw," Wiley Intrescience, www.interscience.wiley.com, Sep. 20, 2004, 223-228. Sep. 20, 2004.

Mopec Bone-Cutting tool, Product brochure, Total pp. 4. First accessed Dec. 15, 2005.

Codman Laminectomy Shaver (a Johnson & Johnson company www.codman.com) catalogue, pp. 416-431, [online] Retrieved from the internet: <URL: http:llwww.codman.com/PDFs/Catalog_04_R.pdf>. First accessed Oct. 24, 2006.

Integra Ruggles TM Kerrison Rongeurs [online] Retrieved from the intrenet: <URL: http://www.integra-Is.com/products!?product=22>. First accessed Oct. 24, 2006.

Herkowitz, "The Cervical Spine Surgery Atlas", 2004, Lippincott Williams & Wilkins; 2nd Edition; pp. 203-206, & 208; Dec. 2003.

\* cited by examiner

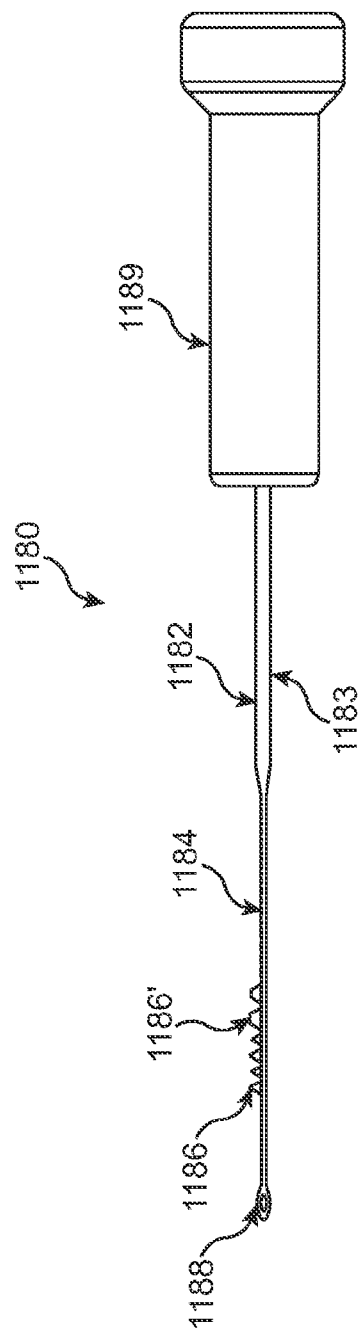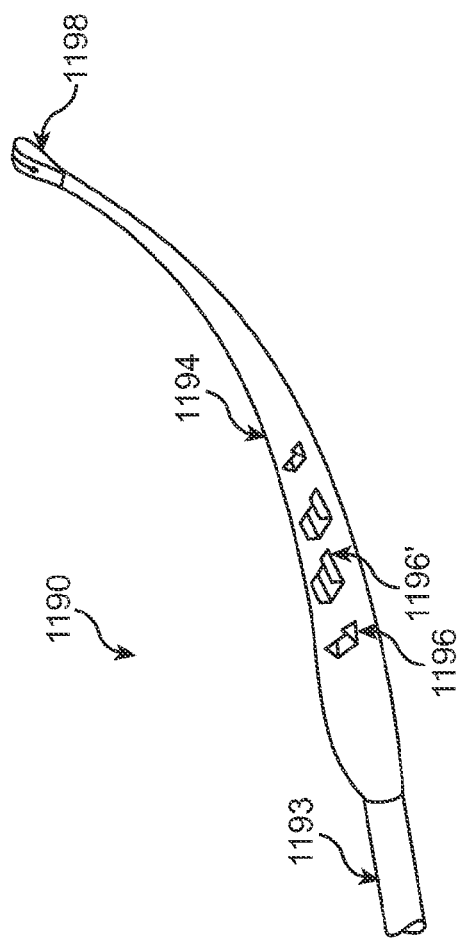

SECTION A-A

SECTION B-B

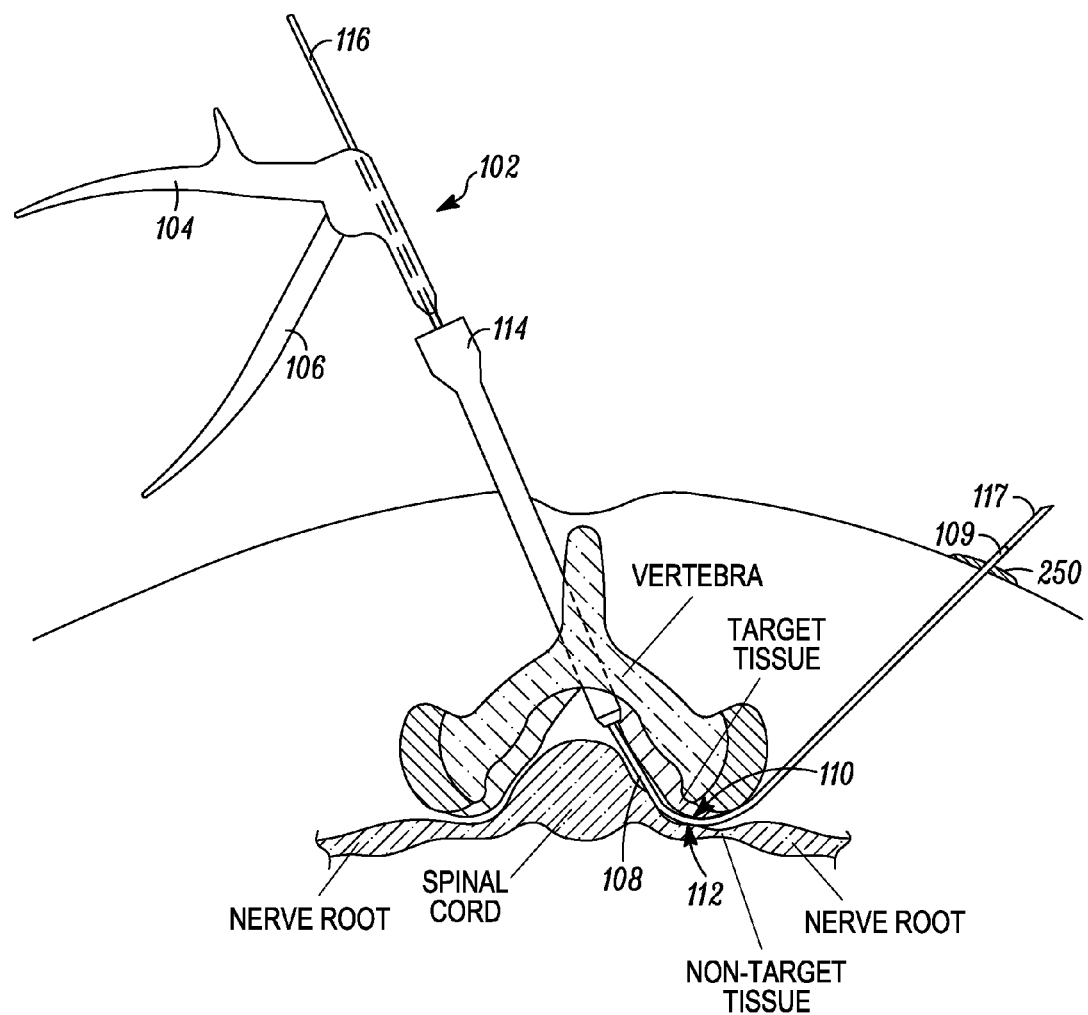
*FIG.* 69A

METHODS, SYSTEMS AND DEVICES FOR CARPAL TUNNEL RELEASE

CROSS-REFERENCES TO RELATED APPLICATIONS

This patent application is a continuation-in-part of U.S. patent application Ser. No. 11/251,199, titled "DEVICES AND METHODS FOR TISSUE MODIFICATION", filed Oct. 15, 2005, which claims the benefit of U.S. Provisional Patent Application Nos. 60/619,306, filed Oct. 15, 2004; 60/622,865, filed Oct. 28, 2004; 60/681,719, filed May 16, 2005; 60/681,864, filed May 16, 2005; and 60/685,190, filed May 27, 2005, each of these applications is herein incorporated by reference in its entirety.

This patent application is also a continuation-in-part of U.S. patent application Ser. No. 11/429,377, titled "FLEXIBLE TISSUE RASP", filed May 4, 2006, which is a continuation-in-part of PCT Patent Application No. PCT/US52005/037136, filed Oct. 15, 2005, which claims the benefit of U.S. Provisional Application Nos. 60/619,306, filed Oct. 15, 2004; 60/622,865, filed Oct. 28, 2004; 60/681,719, filed May 16, 2005; 60/681,864, filed May 16, 2005; and 60/685,190, filed May 27, 2005, each of these applications is herein incorporated by reference in its entirety. U.S. patent application Ser. No. 11/429,377 is also a continuation-in-part of U.S. patent application Ser. No. 11/375,265, entitled "METHODS AND APPARATUS FOR TISSUE MODIFICATION", filed Mar. 13, 2006, now U.S. Pat. No. 7,887,538, which is a continuation-in-part of PCT Patent Application No. PCT/US2005/037136, filed Oct. 15, 2005, which claims the benefit of U.S. Provisional Application Nos. 60/619,306, filed Oct. 15, 2004; 60/622,865, filed Oct. 28, 2004; 60/681,719, filed May 16, 2005; 60/681,864, filed May 16, 2005; and 60/685,190, filed May 27, 2005, each of these applications is herein incorporated by reference in its entirety.

This patent application is also a continuation-in-part of U.S. patent application Ser. No. 11/687,548, titled "TISSUE REMOVAL WITH AT LEAST PARTIALLY FLEXIBLE DEVICES", filed Mar. 16, 2007, which is a continuation-in-part of U.S. patent application Ser. No. 11/429,377, filed May 4, 2006, and also claims the benefit of 60/869,070, filed Dec. 7, 2006, each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are systems, devices, and methods for performing surgical procedures. In particular, described herein are systems, devices and methods for carpal tunnel release procedures.

BACKGROUND OF THE INVENTION

The present invention relates generally to medical/surgical devices and methods. More specifically, the present invention relates to flexible tissue modification devices and methods.

A significant number of surgical procedures involve modifying tissue in a patient's body, such as by removing, cutting, shaving, abrading, shrinking, ablating or otherwise modifying tissue. Minimally invasive (or "less invasive") surgical procedures often involve modifying tissue through one or more small incisions or percutaneous access, and thus may be more technically challenging procedures. Some of the challenges of minimally invasive tissue modification procedures include working in a smaller operating field, working with smaller devices, and trying to operate with reduced or even no direct visualization of the tissue (or tissues) being modified. For example, using arthroscopic surgical techniques for repairing joints such as the knee or the shoulder, it may be quite challenging to modify certain tissues to achieve a desired result, due to the required small size of arthroscopic instruments, the confined surgical space of the joint, lack of direct visualization of the surgical space, and the like. It may be particularly challenging in some surgical procedures, for example, to cut or contour bone or ligamentous tissue with currently available minimally invasive tools and techniques. For example, trying to shave a thin slice of bone off a curved bony surface, using a small-diameter tool in a confined space with little or no ability to see the surface being cut, as may be required in some procedures, may be incredibly challenging or even impossible using currently available devices.

One area of surgery which would likely benefit from the development of less invasive techniques is the treatment of spinal stenosis. Spinal stenosis occurs when nerve tissue and/or the blood vessels supplying nerve tissue in the spine become impinged by one or more structures pressing against them, causing symptoms. The most common form of spinal stenosis occurs in the lower (or lumbar) spine and can cause severe pain, numbness and/or loss of function in the lower back and/or one or both lower limb.

FIG. 1 is a top view of a vertebra with the cauda equina (the bundle of nerves that extends from the base of the spinal cord) shown in cross section and two nerve roots branching from the cauda equina to exit the central spinal canal and extend through intervertebral foramina on either side of the vertebra. Spinal stenosis can occur when the spinal cord, cauda equina and/or nerve root(s) are impinged by one or more tissues in the spine, such as buckled or thickened ligamentum flavum, hypertrophied facet joint (shown as superior articular processes in FIG. 1), osteophytes (or "bone spurs") on vertebrae, spondylolisthesis (sliding of one vertebra relative to an adjacent vertebra), facet joint synovial cysts, and/or collapse, bulging or herniation of an intervertebral disc. Impingement of neural and/or neurovascular tissue in the spine by one or more of these tissues may cause pain, numbness and/or loss of strength or mobility in one or both of a patient's lower limbs and/or of the patient's back.

In the United States, spinal stenosis occurs with an incidence of between 4% and 6% (or more) of adults aged 50 and older and is the most frequent reason cited for back surgery in patients aged 60 and older. Patients suffering from spinal stenosis are typically first treated with conservative approaches such as exercise therapy, analgesics, anti-inflammatory medications, and epidural steroid injections. When these conservative treatment options fail and symptoms are severe, as is frequently the case, surgery may be required to remove impinging tissue and decompress the impinged nerve tissue.

Lumbar spinal stenosis surgery involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods and devices for modifying target tissue in a spine to help ameliorate or treat spinal stenosis, while inhibiting unwanted damage to non-target tissues. Ideally, such techniques and devices would reduce neural and/or neurovascular impingement without removing significant amounts of vertebral bone, joint, or other spinal support structures, thereby avoiding the need for spinal fusion and, ideally, reducing the long-term morbidity resulting from currently available surgical treatments. It may also be advantageous to have minimally invasive or less invasive tissue modification devices capable of treating target tissues in parts of the body other than the spine. At least some of these objectives will be met by the present invention.

SUMMARY OF THE INVENTION

In various embodiments, devices, systems and methods of the present invention provide for minimally invasive or less invasive modification of tissue in a patient. For the purposes of this application, the phrase "tissue modification" includes any type of tissue modification, such as but not limited to removing, cutting, shaving, abrading, shrinking, ablating, shredding, sanding, filing, contouring, carving, melting, heating, cooling, desiccating, expanding, moving, delivering medication or other substance(s) to tissue and/or delivering an implantable device, such as a stent, to tissue to modify the tissue's configuration, shape, position or the like.

In one aspect of the present invention, a device for modifying tissue in a patient may include: an elongate body having a rigid proximal portion and a flexible distal portion having first and second major surfaces; a proximal handle coupled with the proximal portion of the body; one or more tissue modifying members disposed along the first major surface of the distal portion of the body; a guidewire coupled with and extending from the distal portion of the body; and a distal handle removably couplable with the guidewire outside the patient. In some embodiments, the device may be configured to modify spinal tissue, and the device may be configured to extend into the patient's body, along a curved path through an intervertebral foramen of the spine, and out of the patient's body, such that at least part of the flexible distal portion of the elongate body of the device extends into the intervertebral foramen, and the proximal and distal handles reside outside the patient. In one embodiment, a height of the tissue modifying member(s) may be greater than a thickness of a ligamentum flavum of the spine. In alternative embodiments, the device may be configured for use in modifying any of a number of other tissues in the spine or in other parts of a patient's body. In one embodiment, for example, a device may be used to incise the transverse carpal ligament while inhibiting damage of the median nerve to perform a minimally invasive carpal tunnel release procedure. Other tissues in the knee, shoulder, elbow, foot, ankle or other parts of the body may be addressed in alternative embodiments. For example, a device may be used to release of the lacinate ligament of the tarsal tunnel of the foot and/or decompress the posterior tibial nerve, while inhibiting damage of the tibial nerve or its associated branches to perform a minimally invasive tarsal tunnel release procedure.

In various alternative embodiments, the tissue modifying member(s) of a tissue modification device may include, but are not limited to, one or more uni-directional blades, bi-directional blades, teeth, hooks, barbs, hooks, pieces of Gigli saw (or other wire saw), wires, meshes, woven material, knitted material, braided material, planes, graters, raised bumps, other abrasive surfaces, other abrasive materials and/or deliverable substances adhered to or formed in the first major surface. Some embodiments may include one type of tissue modifying member, white other embodiments may include a combination of different tissue modifying members. In some embodiments, the tissue modifying member(s) may be fixedly attached to or formed in the first major surface, and the device may operate by reciprocating the entire device (or most of it) back and forth to cause the tissue modifying member(s) to modify tissue. In alternative embodiments, the tissue modifying member(s) may be moveably attached to or formed in the first major surface, and the device may further include an actuator coupled with the tissue modifying member(s) and extending to the proximal handle for actuating the tissue modifying member(s).

In one embodiment, the elongate body may be at least partially hollow, the distal portion may be flatter than the proximal portion, and the tissue modifying members may comprise blades formed in the first major surface of the distal portion. In some embodiments, the guidewire may be removably coupled with the distal portion of the elongate body via a guidewire coupler comprising a cavity for containing a shaped tip of the guidewire, and wherein the guidewire comprises at least one shaped tip for fitting within the cavity.

Some embodiments may further include a material disposed over a portion of the elongate body distal portion to provide the distal portion with smooth edges. For example, such a material may comprise, in some embodiments, a polymeric cover disposed over the distal portion with one or more openings through which the tissue modifying member(s) protrude. In one embodiment, the material may be further configured to collect tissue removed by the tissue modifying member(s). In some embodiments, the device may include a tissue collection chamber formed in or attached to the elongate body.

In another aspect of the present invention, a device for modifying tissue in a patient may include an elongate body, a proximal handle coupled with the proximal portion of the body, one or more tissue modifying members disposed along the first major surface of the intermediate portion of the body, and a distal handle removably couplable with the distal portion of the body outside the patient. In some embodiments, the elongate body may include a rigid proximal portion, a flexible distal portion, and an intermediate flexible portion disposed between the proximal and distal portions and having first and second major surfaces. In some embodiments, the device may be configured to modify spinal tissue, and the device may be configured to extend into the patient's body, along a curved path through an intervertebral foramen of the spine, and out of the patient's body, such that at least part of the flexible intermediate portion of the elongate body of the device extends into the intervertebral foramen, and the proximal and distal handles reside outside the patient.

In some embodiments, the distal portion of the elongate body may comprise a guidewire coupled with the intermediate portion of the body. In some embodiments, at least the proximal and intermediate portions of the elongate body are at least partially hollow, thus forming at least one lumen. For example, in some embodiments, the at least one lumen may include a suction lumen and/or an irrigation lumen. Optionally, some embodiments may include at least one tissue transport member slidably disposed within the lumen and configured to remove tissue out of the device. For example, in one embodiment the tissue transport member may comprise one or more flexible wires having tissue collection portions disposed under the tissue modifying member(s) of the device. Such tissue collection portions may include, for example, shaped portions of the wire(s), adhesive coating(s) on the wire(s), tissue collecting materials) on the wire(s), adhesive material(s) used to make the wire(s) themselves and/or the like. In alternative embodiments, the tissue transport member may comprise a piece of tissue adhering material disposed under the tissue modifying member(s) of the device. In other alternative embodiments, the tissue transport member may comprise a removable tissue collection chamber disposed under the tissue modifying member(s) of the device. Alternatively, the tissue transport member may comprise at least one uni-directional valve for allowing tissue to pass through the shaft toward the proximal handle while preventing the cut tissue from passing through the valve(s) toward the tissue modifying member(s) of the device.

In some embodiments, at least part of the elongate body may be sufficiently flexible to be compressible, such that tissue may be moved through the elongate body by compressing the compressible portion. Some embodiments of the device may further include a tissue collection chamber formed in or attached to the elongate body.

In another aspect of the present invention, a kit for modifying tissue in a patient may include a tissue modification device, a guidewire configured to couple with a guidewire coupler of the device, and a distal handle removably couplable with the guidewire outside the patient. The tissue modification device may include a rigid shaft having a proximal end and a distal end, a flexible substrate extending from the distal end of the shaft, a proximal handle coupled with the shaft at or near its proximal end, one or more tissue modifying members disposed along one side of the substrate, and a guidewire coupler disposed on the substrate. In some embodiments, the tissue modification device and guidewire, coupled together, may be configured to extend into the patient's body, along a curved path through an intervertebral foramen of the spine, and out of the patient's body, such that at least part of the flexible substrate extends into the intervertebral foramen, and the proximal and distal handles reside outside the patient.

Optionally, some embodiments may also include at least one probe for passing the guidewire between target and non-target tissues in a patient. For example, in some embodiments, the probe may comprise a needle. In alternative embodiments, the probe may comprise a curved, cannulated probe. In any case, a probe may optionally include a flexible guide member for passing through the probe, and such a guide member may have an inner diameter selected to allow passage of the guidewire therethrough.

In some embodiments, the tissue modification device may further include a tissue collection member coupled with the substrate and configured to collect tissue. Such an embodiment may optionally further include tissue transport means configured to transport the collected tissue through the device.

In another aspect of the present invention, a method for modifying target tissue in a patient while inhibiting damage to non-target tissues may involve: advancing a flexible distal portion of an elongate tissue modification device into the patient's body and along a curved path between target and non-target tissues, such that a distal end of the distal portion exits the patient's body; coupling a first handle with the distal portion outside the patient; applying a first tensioning force to the first handle; applying a second tensioning force to a second handle coupled with a rigid proximal portion of the device, the first and second tensioning forces urging one or more tissue modifying members disposed along the flexible distal portion against the target tissue; and reciprocating at least a portion of the device back and forth, while maintaining at least some of the tensioning force, to cause the tissue modifying member(s) to modify the target tissue.

In some embodiments, advancing the distal portion may involve advancing through an intervertebral foramen of the patient's spine, and reciprocating the device may involve modifying ligamentum flavum and/or bone. In some embodiments, advancing the distal portion may involve advancing percutaneously into the patient. In some embodiments, the distal portion of the device may be advanced into the patient's spine without removing bone, and only ligamentum flavum tissue may be modified. The method may optionally further involve manipulating the second handle and thus the rigid proximal portion to steer the flexible portion of the device.

In one embodiment, the flexible distal portion may include a flexible substrate coupled with a flexible guidewire, coupling the first handle may involve coupling with the guidewire, and advancing the distal portion may involve pulling the guidewire with the first handle to advance the flexible substrate between the target and non-target tissue. In various embodiment, the target tissue may include, but is not limited to, ligament, tendon, bone, tumor, cyst, cartilage, scar, osteophyte and inflammatory tissue, and the non-target tissue may include, but is not limited to, neural tissue and neurovascular tissue. In one embodiment, for example, the target tissue may include a transverse carpal ligament, and the non-target tissue may include a median nerve. Alternatively, for example, a device may be used to release of the lacinate ligament of the tarsal tunnel of the foot and/or decompress the posterior tibial nerve, while inhibiting damage of the tibial nerve or its associated branches to perform a minimally invasive tarsal tunnel release procedure.

In some embodiments, the tensioning forces may urge a plurality of tissue modifying members against a curved target tissue along a length of the flexible portion. In some embodiments, reciprocating at least a portion of the device may involve reciprocating an entire portion between the first and second handles, and reciprocating may cause a tissue modifying surface of the flexible portion to modify the target tissue while an atraumatic surface of the flexible portion faces the non-target tissue. In alternative embodiments, reciprocating at least a portion of the device may involve reciprocating a tissue moth surface of the flexible portion, and reciprocating may cause the tissue modifying surface to modify the target tissue white an atraumatic surface of the flexible portion faces the non-target tissue.

Optionally, in some embodiments, the method may further involve collecting cut tissue in the tissue modification device. In some embodiments, the method may additionally include transporting the cut tissue out of the patient through the tissue modification device. For example, transporting the cut tissue may involve applying suction and/or irrigation in the tissue collection chamber. Alternatively, transporting the cut tissue may involve collecting the cut tissue on or in one or more tissue transport members and withdrawing the tissue transport member(s) through the tissue modification device.

In another aspect, the invention provides a method for removing a target ligament and/or bone tissue of a patient. The method comprises providing an elongate body having an axis and an elongate, axially flexible portion affixed to a rigid shaft portion. The flexible portion is positioned within the patient so that a first surface of the flexible portion is oriented toward the target tissue. The first surface is shifted toward a target region of the target tissue by moving the rigid portion, and the target region of the target tissue is removed with a tissue modifying member disposed along the first surface.

Optionally the rigid portion extends axially from a first end of the flexible portion. The flexible portion can be flexible in one lateral orientation, and may be stiffer in another lateral orientation (for example, in the direction in which it is shifted). The flexible portion can be positioned so that the first surface of the flexible portion bends over the target tissue, and/or the flexible portion may be axially tensioned to urge the first surface toward the target tissue. The tension can be applied to the first end by pulling the rigid portion from outside the patient.

In many embodiments, the surface will be shifted by applying torque to the rigid portion from outside the body portion. The rigid portion can then rotate the flexible portion about the axis an as to shift an orientation of the first surface toward a target region of the target tissue. Where the target tissue has a convex surface defining an outward orientation and an inward orientation, and where the first surface is bordered by first and second opposed edges, the target tissue adjacent the first edge may be inward of the target tissue adjacent the second edge. As a result, the tension of the flexible portion may induce rolling of the flexible portion about the axis toward the first edge. The torquing of the shaft portion may counteract the tension-induced rolling to inhibit flipping of the flexible portion.

A distal handle may be coupled with a second end of the flexible portion, and the flexible portion may be manually tensioned by simultaneous pulling, from outside the patient, on the first and second handles. Axially moving the tissue modifying member along a curving path may be performed within the patient by relative movement between the first and second handles, the curving path including the bend over the target tissue. Lateral translation of the rigid portion from outside the patient can be used to induce the lateral shifting of the first surface, particularly where the flexible portion is stiffer in a second lateral orientation extending along the first surface, with the first surface typically shifting along that second lateral orientation.

In some embodiments, pivoting of the rigid portion about tissues disposed along the rigid portion may be used to induce the lateral shifting of the first surface. Optionally, a first handle may be attached to the rigid portion outside the patient, and the flexible portion can be manually tensioned and shifted by manipulating the first handle with a hand. A distal handle can be coupled with a second end of the flexible portion, and the flexible portion can be manually tensioned by simultaneous pulling, from outside the patient, on the first and second handles. Axially moving of the tissue modifying member along a curving path within the patient can be effected by relative movement between the first and second handles, typically with the curving path including a bend over the target tissue. Reciprocation of the tissue modifying member along the curved path and against the target tissue can be provided by sequentially pulling on the first and second handles so that a cutting edge of the tissue modifying member incises the target tissue. In some embodiments, another rigid portion extends from the second handle to the second end of the flexible portion inside the patient, with the first surface of the flexible portion being shifted using both rigid portions.

In yet another aspect, the invention provides a system for removing a target tissue of a patient. The system comprises an elongate flexible portion having a first end and a second end with an axis therebetween. The flexible portion has a first surface extending along the axis and is axially bendable in a first lateral orientation. A rigid portion is extendable from the flexible body portion so that pulling on the rigid portion can axially tension the flexible portion to urge the first surface toward the target tissue. Movement of the rigid portion can be used to shift the first surface toward a target region of the target tissue. A tissue modifying member disposed along the first surface can be configured to effect removal of the target region of the target tissue.

Also described herein are methods of cutting a ligament of a patient. In general, the method may include the steps of advancing a cannulated probe into a patient, advancing a tissue modification device assembly through the cannulated probe and anterior to a ligament of a patient, advancing the distal end of the tissue modification device assembly posteriorly through the skin of the patient such that it exits the patient, exposing at least one tissue modification element of the tissue modification device assembly, and reciprocating at least a portion of the tissue modification device assembly by alternately pulling on proximal and distal portions of the tissue modification device assembly to draw the at least one tissue modification element across the ligament to cut the ligament.

In some embodiments, the method may further include the step of confirming proper placement with a nerve stimulator. In some embodiments, the method may further include the step of attaching a nerve stimulator to a tissue modification device assembly.

In some embodiments, the method may further include the step of coupling a distal handle to the distal end of the tissue modification device assembly, exterior to the patient.

Alternatively, in some embodiments, the method of cutting a ligament of a patient may include the steps of advancing a tissue modification device assembly into a patient and anterior to a ligament of a patient, advancing the distal end of the tissue modification device assembly posteriorly through the skin of the patient such that it exits the patient, exposing at least one tissue modification element of the tissue modification device assembly, and reciprocating at least a portion of the tissue modification device assembly by alternately pulling on proximal and distal portions of the tissue modification device assembly to draw the at least one tissue modification element across the ligament to cut the ligament.

In some embodiments, the method may further include the step of confirming proper placement with a nerve stimulator.

In some embodiments, the method may further include the step of attaching a nerve stimulator to a tissue modification device assembly.

In some embodiments, the method may further include the step of coupling a distal handle to the distal end of the tissue modification device assembly, exterior to the patient.

Also described herein are systems for cutting a ligament of a patient. In general, the systems may include a probe configured to be advanced into a patient and a tissue modification device. The tissue modification device may include a proximal handle, at least one tissue modification element configured cut ligament, and a sharp distal tip, wherein the sharp distal tip is configured to be advanced anterior to a ligament of a patient and posteriorly through the skin of the patient such that it exits the patient. In some embodiments, the system may further include a sheath configured to limit the exposure of the tissue modification element of tissue modification device, wherein the tissue modification device is configured for placement within the sheath such that tissue modification element is locally exposed by the sheath.

In some embodiments, the system may further include a nerve stimulator configured to couple to the tissue modification device to confirm correct placement of the tissue modification device. In some embodiments, the system may further include a distal handle configured to couple to the sharp distal tip of the tissue modification device.

In some embodiments, the probe is a cannulated probe and the tissue modification device is configured to be deployed through the cannulated probe.

Also described herein are devices for cutting ligament of a patient. In general, the device may include a proximal handle, at least one tissue modification element configured cut ligament, a sharp distal tip, wherein the sharp distal tip is configured to be advanced anterior to a ligament of a patient and posteriorly through the skin of the patient such that it exits the patient, and a sheath configured to limit the exposure of the tissue modification element, wherein the tissue modification element is configured for placement within the sheath such that tissue modification element is locally exposed by the sheath.

In some embodiments, the device may further include a distal handle configured to couple to the sharp distal tip.

Also described herein are systems for cutting a ligament of a patient. In general, the systems may include a probe configured to be advanced into a patient and a tissue modification device. The tissue modification device may include a proximal handle, an abrasive surface configured cut ligament, a sharp distal tip, wherein the sharp distal tip is configured to be advanced anterior to a ligament of a patient and posteriorly through the skin of the patient such that it exits the patient. The systems may also include a protective cover disposed about the tissue modification device configured to limit the exposure of the abrasive surface.

In some embodiments, the system may further include a nerve stimulator configured to couple to the tissue modification device to confirm correct placement of the tissue modification device.

In some embodiments, the system may further include a distal handle configured to couple to the sharp distal tip of the tissue modification device.

In some embodiments, the probe is a cannulated probe and the tissue modification device is configured to be deployed through the cannulated probe.

Also described herein are methods of performing a minimally invasive carpal tunnel release procedure to cut a target transverse carpal ligament. In general, the methods may include the steps of advancing a probe percutaneously though a patient's skin from a first location, advancing a tissue modification device from the first location and between the target ligament and non-target tissue so that a proximal handle on the tissue modification device extends from the patient at the first location, wherein the tissue modification device includes a flexible distal region having uni-directional blades, attaching a distal handle in communication with the distal end of the tissue modification device, wherein the distal handle extends from the patient at a second location, and reciprocating the tissue modification device using the proximal handle and distal handles to incise the transverse carpal ligament with the unidirectional blades.

In some embodiments, the tissue modification device includes an atraumatic cover forming an aperture through which the blades may engage the target ligament.

In some embodiments, reciprocating further includes tensioning the tissue modification device to urge the blades towards the target ligament.

In some embodiments, the methods further include the step of verifying correct device placement with a nerve stimulator. In some embodiments, the methods further include the step of attaching a nerve stimulator to a tissue modification device assembly.

Also described herein are methods of performing a minimally invasive carpal tunnel release procedure to cut a target transverse carpal ligament. In general the methods may include the steps of advancing a tissue modification device through a small incision at a first location on a subject's skin and between the target ligament and non-target tissue so that a proximal handle on the tissue modification device extends from the patient at the first location, wherein the tissue modification device includes a flexible distal region having uni-directional blades, attaching a distal handle in communication with the distal end of the tissue modification device, wherein the distal handle extends from the patient at a second location, and reciprocating the tissue modification device using the proximal handle and distal handles to incise the transverse carpal ligament with the uni-directional blades.

In some embodiments, the tissue modification device comprises an atraumatic cover forming an aperture through which the blades may engage the target ligament.

In some embodiments, reciprocating further comprises tensioning the tissue modification device to urge the blades towards the target ligament.

In some embodiments, the methods further include verifying correct device placement with a nerve stimulator. In some embodiments, the methods further include attaching a nerve stimulator to a tissue modification device assembly.

Also described herein are systems for performing a minimally invasive carpal tunnel release procedure to cut a target transverse carpal ligament. In general the systems may include a probe configured to be advanced percutaneously though a patient's skin from a first location, a tissue modification device comprising a proximal handle and a flexible distal region having uni-directional blades, and a distal handle configured to connect to the distal end of the tissue modification device, wherein the tissue modification device is configured to be reciprocated using the proximal handle and distal handles to incise the transverse carpal ligament with the uni-directional blades.

In some embodiments, the system may further include a nerve stimulator configured to couple to the tissue modification device and verify correct placement of the tissue modification device.

In some embodiments, the probe is a cannulated probe and the tissue modification device assembly is configured to be deployed through the cannulated probe.

Also described herein are devices for performing a minimally invasive carpal tunnel release procedure to cut a target transverse carpal ligament. In general the device may include a tissue modification device comprising a proximal handle and a flexible distal region having uni-directional blades, a distal handle configured to connect to the distal end of the tissue modification device, wherein the tissue modification device is configured to be reciprocated using the proximal handle and distal handles to incise the transverse carpal ligament with the unidirectional blades.

Also described herein are methods for modifying a transverse carpal ligament in a patient. In general the methods may include the steps of advancing a distal portion of an elongate tissue modification device into the patient's body and along a path between target and non-target tissues, such that a distal end of the distal portion exits the patient's body, applying a first force to a distal portion of the tissue modification device outside the patient, applying a second force to a proximal portion of the tissue modification device, the first and second forces urging one or more tissue modifying members of the tissue modification device against the target tissue, reciprocating at least a portion of the tissue modification device back and forth to cause the one or more tissue modifying members to modify the target tissue.

In some embodiments, the target tissue is the transverse carpal ligament.

In some embodiments, reciprocating at least a portion of the tissue modification device back and forth causes the one or more tissue modifying members incise the transverse carpal ligament.

In some embodiments, the method may further include coupling a first handle with the distal portion of the tissue modification device outside the patient and applying the first force to the distal handle.

These and other aspects and embodiments are described more fully below in the Detailed Description, with reference to the attached Drawings.

BRIEF DESCRIPTION OF THE DRAWINGS

FIG. 24 is a side view of a tissue modification device with vertically oriented blades, according to one embodiment of the present invention;

FIG. 25 is a perspective view of a flexible portion of a tissue modification device with vertically oriented blades, according to one embodiment of the present invention;

FIG. 69A is a cross-sectional view of a portion of a patient's spine and back, with apparatus for modifying tissue in position for modifying spinal tissue and with a distal portion of the apparatus anchored outside the patient according to one embodiment of the present invention.

DETAILED DESCRIPTION OF THE INVENTION

Various embodiments of tissue modification devices and systems, as well as methods for making and using same, are provided. Although much of the following description and accompanying drawing figures generally focuses on surgical procedures in spine, in alternative embodiments, devices, systems and methods of the present invention may be used in any of a number of other anatomical locations in a patient's body. For example, in some embodiments, flexible tissue modification devices of the present invention may be used in minimally invasive procedures in the shoulder, elbow, wrist, hand, hip, knee, foot, ankle, other joints, or other anatomical locations in the body. Similarly, although some embodiments may be used to remove or otherwise modify ligamentum flavum and/or bone in a spine to treat spinal stenosis, in alternative embodiments, any of a number of other tissues may be modified to treat any of a number of other conditions. For example, in various embodiments, treated tissues may include but are not limited to ligament, tendon, bone, tumor, cyst, cartilage, scar, osteophyte, inflammatory tissue and the like. Non-target tissues may include neural tissue and/or neurovascular tissue in some embodiments or any of a number of other tissues and/or structures in other embodiments. In one alternative embodiment, for example, a flexible tissue modification device may be used to incise a transverse carpal ligament in a wrist white inhibiting damage to the median nerve, to perform a minimally invasive carpal tunnel release procedure. Thus, various embodiments described herein may be used to modify any of a number of different tissues, in any of a number of anatomical locations in the body, to treat any of a number of different conditions. For example, a device may be used to release of the lacinate ligament of the tarsal tunnel of the foot and/or decompress the posterior tibial nerve, while inhibiting damage of the tibial nerve or its associated branches to perform a minimally invasive tarsal tunnel release procedure.

Figure 1:
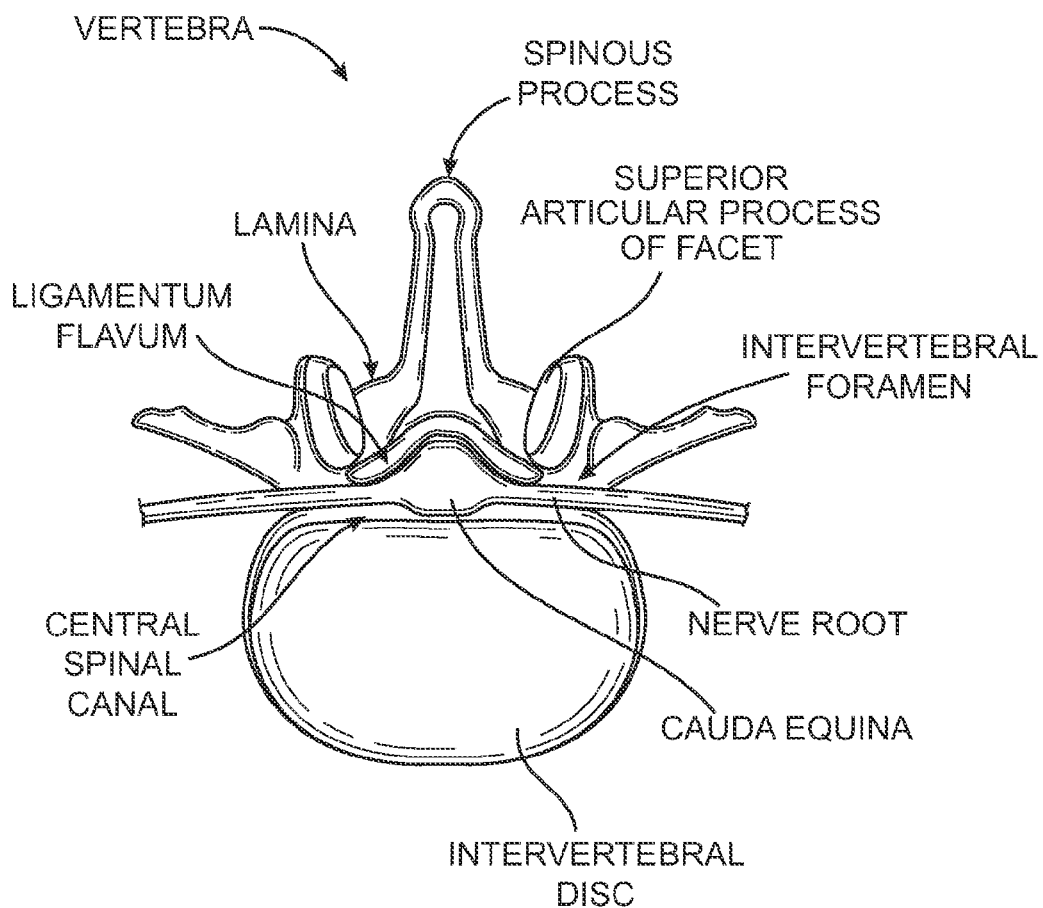
FIG. 1 is a top view of a vertebra with the cauda equina shown in cross section and two nerve roots branching from the cauda equina to exit the central spinal canal and extend through intervertebral foramina on either side of the vertebra.
Figure 2A:
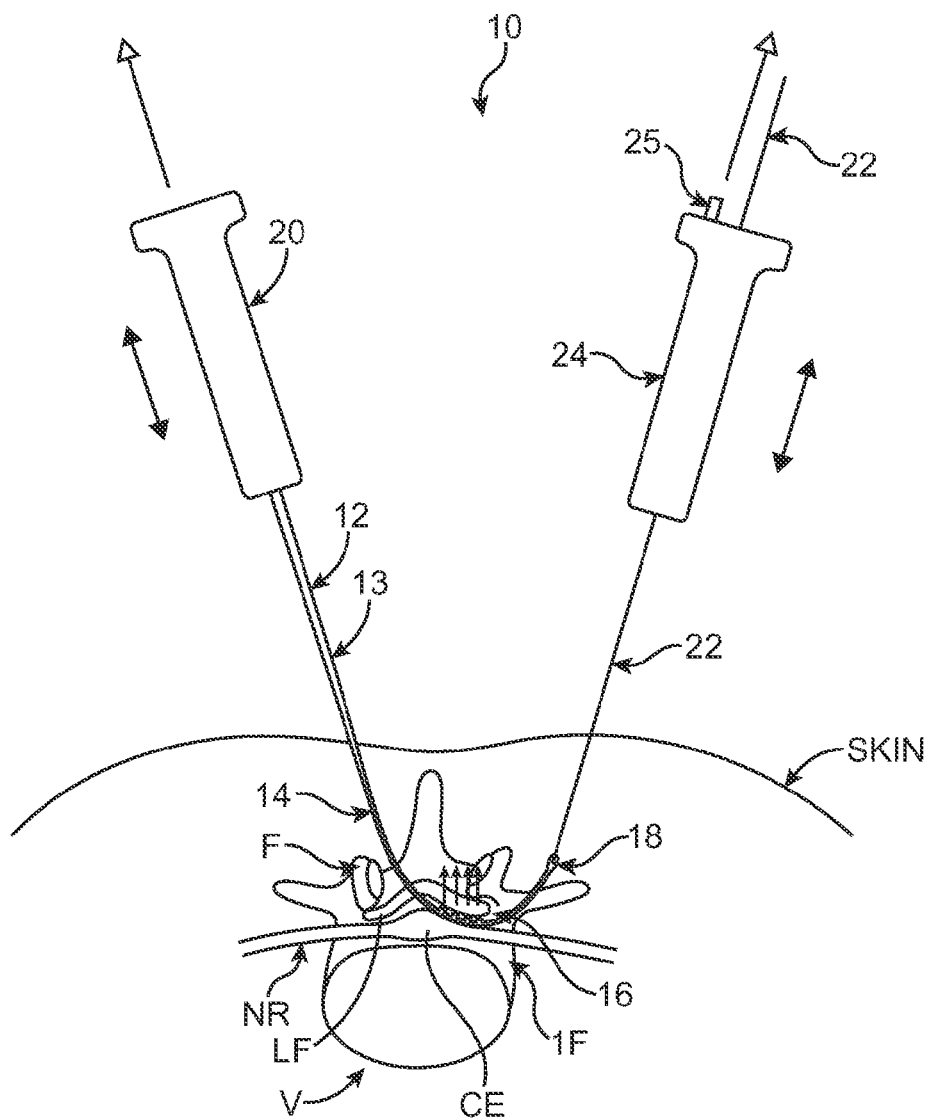
FIG. 2A is a cross-sectional view of a patient's back and a side view of a flexible tissue modification device in position in a spine, according to one embodiment of the present invention.

With reference now to FIG. 2A, a tissue modification device 10 according to one embodiment may suitably include a proximal handle 20 coupled with a shaft 12 having a proximal, rigid portion 13 and a distal, flexible portion 14 on which one or more tissue modifying members 16 may be disposed. A guidewire coupler 18 may be formed in (or attached to) flexible portion 14 at or near its distal end, for coupling with a guidewire 22, which in turn may be coupled with a guidewire handle 24 (or "distal handle"), which may include a tightening lever 25 for tightening handle 24 around guidewire 22.

Device 10 is shown percutaneously placed in position for performing a tissue modification procedure in a patient's spine, with various anatomical structures shown including a vertebra V, cauda equina CE, ligamentum flavum LF, nerve root NR, facet F, and intervertebral foramen IF. Various embodiments of device 10 may be used in the spine to remove ligamentum flavum LF, facet bone F, bony growths, or some combination thereof, to help decompress cauda equina CE and/or nerve root NR tissue and thus help treat spinal stenosis and/or neural or neurovascular impingement. Although this use of device 10 will not be continuously repeated for every embodiment below, any of the described embodiments may be used to remove ligamentum flavum alone, bone alone, or a combination of ligament and bone in the spine to treat neural impingement, neurovascular impingement and/or spinal stenosis.

In one embodiment of a method for modifying tissue using device 10, a distal end of 22 guidewire may be placed into the patient, along a curved path between target and non-target tissue, and out of the patient. A distal portion of guidewire 22 may then be coupled with guidewire handle 24, such as by passing guidewire 22 through a central bore in handle 24 and tightening handle 24 around guidewire 22 via tightening lever 25 or other tightening means. A proximal end of guidewire 22 may then be coupled with coupling member 18 and used to pull distal shaft portion 14 between target and non-target tissues. In some embodiments, device 10 may be advanced into the patient percutaneously, while in alternative embodiments, device 10 may be advanced through a small incision or larger incision. Once advanced into the patient, flexible distal shaft portion 14 may be advanced along a curved path between the target and non-target tissues, and in some instances may be pulled at least partway into an intervertebral foramen IF of the spine.

Proximal handle 20 and guidewire handle 24 may be pulled (or "tensioned"—solid/single-tipped arrows) to urge tissue modifying members 16 against the target tissue (in this case, ligamentum flavum LF). Generally, tissue modifying members 16 may be fixedly attached to (or formed in) on one side or surface of distal portion 14, while an opposite side or portion of distal portion 14 faces non-target tissue, such as cauda equina CE and/or nerve root NR. The opposite side of distal portion 14 will generally be atraumatic and/or include an atraumatic cover, coating, shield, barrier, tissue capture member or the like. With tensioning force applied to device 10, handles 20, 24 may be used to reciprocate device 10 back and forth (solid/double-tipped arrows) to cause tissue modifying members 16 to cut, remove, shred or otherwise modify the target tissue. In various embodiments, for example, target tissue may include only ligamentum flavum LF, only bone, or a combination of both.

Reciprocation and tensioning may be continued until a desired amount of tissue is removed. Removed target tissue, in some embodiments, may be collected, captured or trapped between tissue modifying members 16 and/or in one or more tissue capture members or chambers (not shown). When a desired amount of target tissue has been removed, which may be determined, for example, by tactile feedback provided to the surgeon by device 10, by radiographic imaging, and/or by direct visualization (such as in an open surgical case), guidewire 22 may be released from distal handle 24, and device 10 may be removed from the patient's back. If desired, device 10 may be passed into the patient's spine again for additional tissue modification, and/or other devices may be passed into the spine.

Additional details of various methods for inserting and using device 10 are provided below. For further explanation of guidewire systems and methods for inserting devices to remove or otherwise modify tissue, reference may also be made to U.S. patent application Ser. Nos. 11/468,247 and 11/468,252, both titled "Tissue Access Guidewire System and Method," and both filed Aug. 29, 2006, the full disclosures of which are hereby incorporated by reference.

Figure 2B:
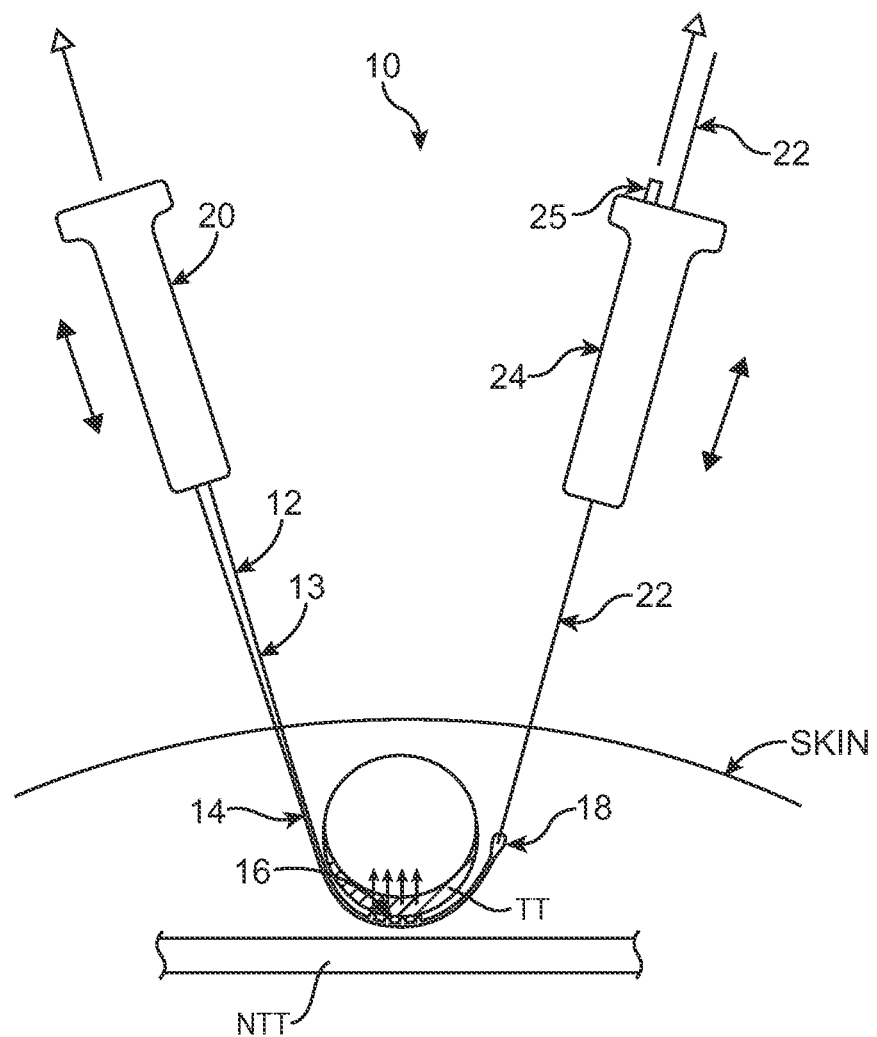
FIG. 2B is a diagrammatic view of a generic portion of a patient's body, showing target and non-target tissue, with the device of FIG. 2A in position to modify target tissue, according to one embodiment of the present invention.

Referring now to FIG. 2B, in various embodiments, device 10 may be used in parts of the body other than spine to remove target tissue TT while avoiding harm to non-target tissue NTT. For example, target tissue TT may include soft tissue adhering to bone, such as ligament and/or cartilage, and/or may include bone. Non-target tissue NTT may include any nervous tissue, vascular tissue, an organ, or any other tissue that a surgeon may desire to leave unharmed by a surgical procedure. In one embodiment, for example, device 10 may be used to perform a minimally invasive carpal tunnel release procedure by releasing the transverse carpal ligament without damaging the median nerve. In some embodiments, such a procedure may be performed percutaneously with or without an endoscope. In other embodiments, device 10 may be used to remove cartilage and/or ligament from a knee or shoulder in a minimally invasive procedure. In yet another embodiment, device 10 may be used to perform a minimally invasive bunionectomy. Therefore, although the following discussion focuses primarily on various uses of alternative embodiments of device 10 in spine, any of a number of other anatomical structures may be operated upon in different embodiments. For example, a device may be used to release of the lacinate ligament of the tarsal tunnel of the foot and/or decompress the posterior tibial nerve, white inhibiting damage of the tibial nerve or its associated branches to perform a minimally invasive tarsal tunnel release procedure.

Figure 2C:
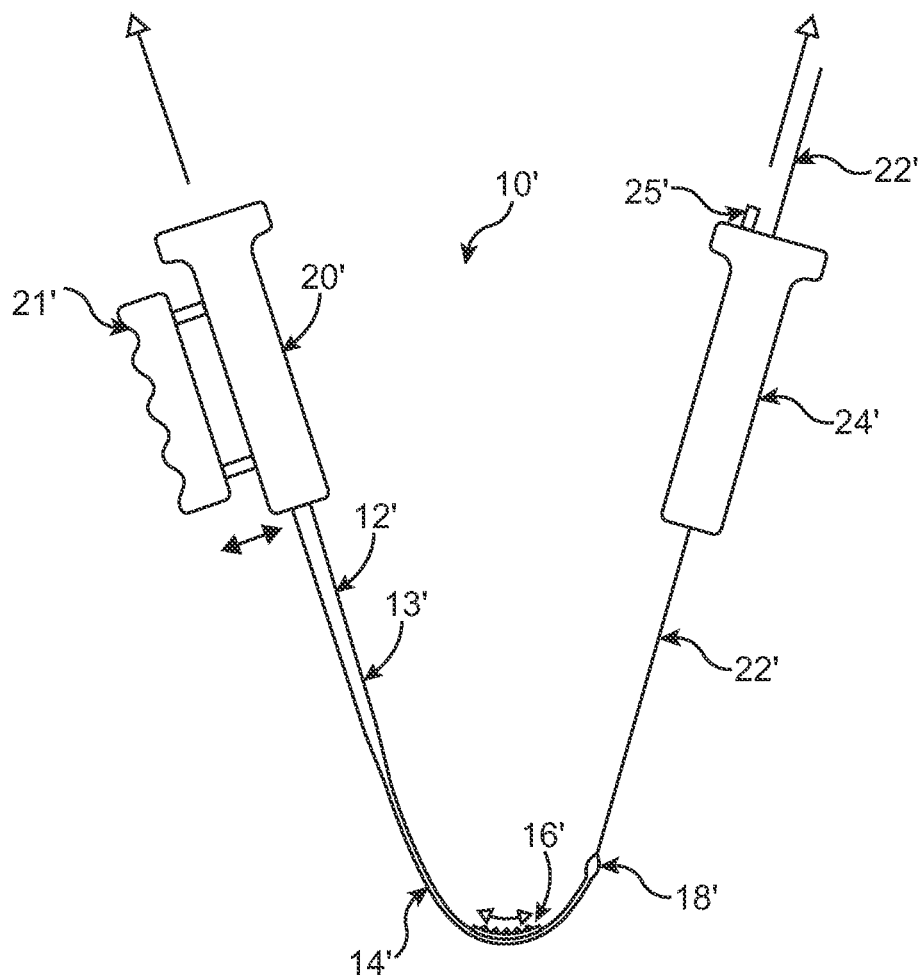
FIG. 2C is a side view of a tissue modification device, according to an alternative embodiment of the present invention.

Referring now to FIG. 2C, in an alternative embodiment, a tissue modification device 10' may suitably include a proximal handle 20', including a squeeze actuator 21' and coupled with a shaft 12' having a proximal, rigid portion 13' and a distal, flexible portion 14'. One or more tissue modifying members 16' may be moveably coupled with one side of flexible portion 14', and a guidewire coupler 18' may be formed in (or attached to) flexible portion 14' at or near its distal end, for coupling with a guidewire 22' and thus a distal handle 24' with a tightening lever 25'.

In this alternative embodiment, squeeze actuator 21' may be coupled with moveable tissue modifying members 16' by any suitable means, such that actuating actuator 21' (double-headed, solid-tipped arrow) causes tissue modifying members 16' to reciprocate back and forth (double-headed, hollow-tipped arrow). In use, therefore, device 10' as a whole may be held relatively stationary, while tissue modifying members 16' are reciprocated. Proximal handle 20' and rigid proximal shaft portion 13' may be used to steer device 10' relative to target tissue, and of course device 10' may be moved in and out of the patient and/or the target tissue, but it may also be possible to hold device 10' relatively stationary while reciprocating tissue modifying members 16'. In various embodiments, squeeze actuator 21' may be replaced with any suitable mechanical actuator, such as a trigger, lever or the like.

Figure 2D:
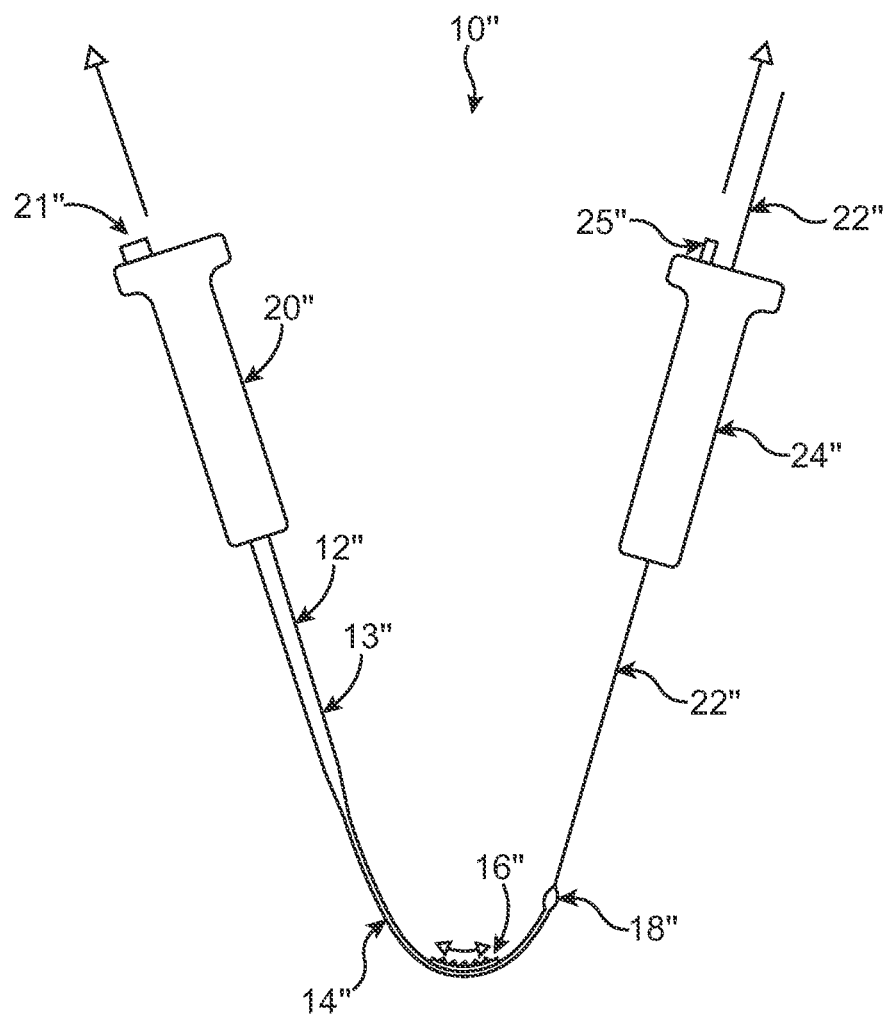
FIG. 2D is a side view of a tissue modification device, according to another alternative embodiment of the present invention.

With reference now to FIG. 2D, in another alternative embodiment, a tissue modification device 10" may be similar to the previous embodiment but may include, instead of squeeze actuator 21', a button actuator 21" and a powered drive mechanism within handle 20". Pressing button actuator 21" may activate tissue modifying members 16" to reciprocate back and forth to modify tissue. In various alternative embodiments, button 21" may be replaced with any suitable actuator, such as a trigger, switch, dial or the like.

Figure 3A:
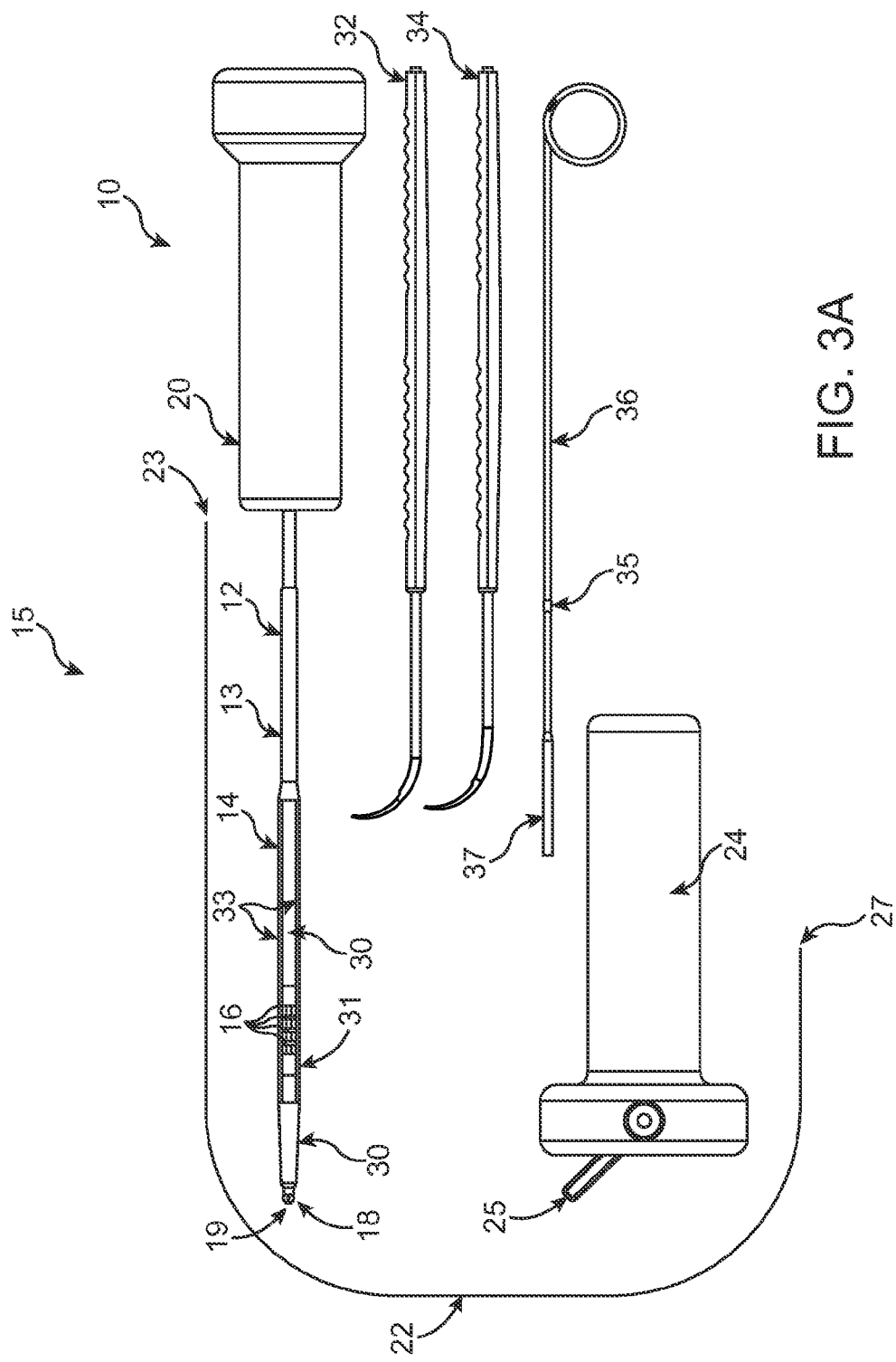
FIG. 3A is a view of a kit or system for modifying tissue, according to one embodiment of the present invention.

With reference now to FIG. 3A, in some embodiments tissue modification device 10 may be provided as a system (or "kit"), including the various components described above in reference to FIGS. 2A and 2B. In some embodiments, a tissue modification system 15 or kit may suitably include device 10 of FIGS. 2A and 2B, as well as one or more additional devices or components. For example, multiple guidewires 22 may be provided as part of system 15. In some embodiments, system 15 may also include one or more guidewire passage probes 32, 34 and a curved, flexible guide member 36. In one embodiment, for example, an ipsilateral access probe 32 and a contralateral access probe 34 may be provided. Curved guide member 36 is generally configured to pass through a lumen in each of probes 32, 34 and includes an inner lumen through which guidewire 22 may be passed. Guide member 36 may further include one or more depth marks 35 to indicate to a surgeon when guide member 36 has been passed a certain distance into probe 32, 34 and a stop 37 to limit passage of guide member 36 farther into probe 32, 34. In an alternative embodiment (not shown), such as might be used in a completely percutaneous procedure, probes 32, 34 may be replaced with an introducer needle, such as but not limited to a 14 gauge Touhy epidural needle or other size or type of epidural needle. In such an embodiment, guide member 36 may be designed to pass through the bore of the needle. For further description of various probe and guide member devices, reference may be made to U.S. patent application Ser. Nos. 11/468,247 and 11/468,252. Further reference may be made to U.S. patent application Ser. Nos. 11/457,416, titled "Spinal Access and Neural Localization," and filed Jul. 13, 2006; and 60/823,594, titled "Surgical Probe and Method of Making," and filed Aug. 25, 2006, the full disclosures of which are hereby incorporated by reference.

Guidewire 22 may be made of any suitable material, such as nitinol or stainless steel, and may include a sharp distal tip 23, to facilitate passage of guidewire 22 through tissue, and a proximal shaped end 27 for coupling with guidewire coupler 18. Further details of various guidewire 22 embodiments and distal handle 24 are provided, for example, in U.S. patent application Ser. Nos. 11/468,247 and 11/468,252, which were previously incorporated by reference.

Figure 3B:
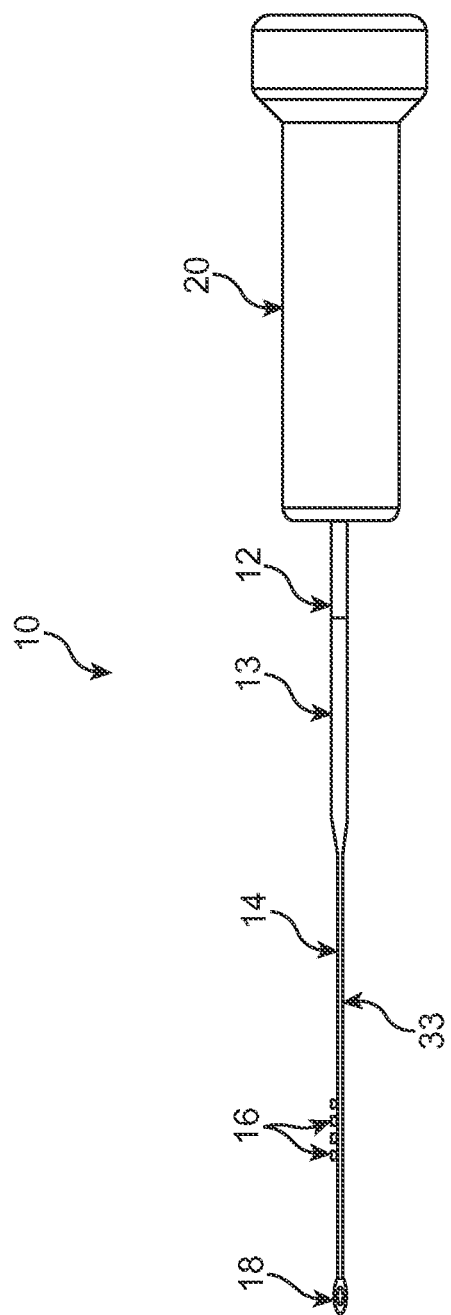
FIG. 3B is a side view of a portion of the kit of FIG. 3B.

FIGS. 3A and 3B show proximal handle 20 and shaft 12 in greater detail than in previous figures. In the embodiment shown, four tissue modifying members 16 are fixedly attached to one side of flexible distal shaft portion 14, each comprising grooved blades with bi-directional cutting edges. In various alternative embodiments, any number of tissue modifying members 16 may be included, such as from one to twenty tissue modifying members 16. Furthermore, tissue modifying members 16 may have any of a number of different configurations, some of which are described below, such unidirectional blades, bi-directional blades, teeth, hooks, barbs, hooks, pieces of Gigli saw (or other wire saw), wires, meshes, woven material, knitted material, braided material, planes, graters, raised bumps, other abrasive surfaces, other abrasive materials, deliverable substances and/or the like.

In various embodiments, proximal shaft portion 13, distal shaft portion 14, tissue modifying members 16 and guidewire coupler 18 may be made of any suitable material (or materials), and may be made from one piece of material as a single extrusion or from separate pieces attached together. For example, in many embodiments, all of shaft 12 and guidewire coupler 18 may be made from one piece of material, and tissue modifying members 16 may be attached to distal shaft portion 14, such as by welding. In alternative embodiments, however, guidewire coupler 18 may be a separate piece attached to distal shaft portion 14 and/or tissue modifying members 16 may be formed in (rather than attached to) distal shaft portion 14. In yet another embodiment, distal shaft portion 14 may comprise a flat piece of material coupled with rigid proximal shaft portion 13, such as by welding. In some embodiments, shaft 12 may be formed from one piece of material, and distal shaft portion 14 may be flattened to derive its shape and flexibility. In some embodiments, one or more slits may be formed in distal shaft portion 14, to enhance its flexibility. In some embodiments, proximal shaft portion 13 may have a cylindrical shape. In some embodiments proximal shaft portion 13, distal shaft portion 14, or both may be hollow. Alternatively, any portion of shaft 12 may be solid in some embodiments, such as to give proximal shaft portion 13 added rigidity.

In one embodiment, guidewire coupler 18 may include a slot 19, shaped to receive and hold guidewire proximal shaped end 27. In various embodiments, slot 19 may be located on the top surface of distal shaft portion 14, as shown, or on the bottom surface. For further description of various embodiments of guidewire couplers, reference may be made to U.S. patent application Ser. Nos. 11/468,247 and 11/468, 252. In some embodiments, an atraumatic cover 30 may be disposed over part of distal shaft portion 14, forming atraumatic edges 33 and an aperture 31 through which tissue modifying members 16 protrude. Cover 30 may be made of any suitable atraumatic material, such as any of a number of different polymers. In some embodiments, cover 30 may also serve to collect cut tissue.

FIG. 3B is a side view of device 10. Tissue modifying members 16 may be seen extending above atraumatic edges 33 of cover 30 and having cutting edges facing both proximally and distally. In alternative embodiments, tissue modifying members 16 may have only uni-directional cutting edges, such as facing only proximally or only distally. In the embodiment shown, guidewire coupler 18 is formed as a loop at the distal end of distal shaft portion 14. Guidewire shaped end 27 may generally fit into slot 19 (not visible in FIG. 3B) to reside within the loop of guidewire coupler 18 during use. In other embodiments, guidewire coupler 18 may comprise a separate piece attached to the top side or bottom side of distal shaft portion 14. Examples of such embodiments are described further in U.S. patent application Ser. Nos. 11/468, 247 and 11/468,252.

The various components of device 10, including proximal handle 20, shaft 12, tissue modifying members 16, guidewire coupler 18, and cover 30, may be fabricated from any suitable material or combination of materials. Suitable materials include, for example, metals, polymers, ceramics, or composites thereof. Suitable metals may include, but are not limited to, stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Suitable polymers include, but are not limited to, nylon, polyester, Dacron®, polyethylene, acetal, Delrin® (DuPont, Wilmington, Del.), polycarbonate, nylon, polyetheretherketone (PEEK), and polyetherketoneketone (PEKK). Ceramics may include, but are not limited to, aluminas, zirconias, and carbides. In some embodiments, one or more portions of shaft 12, for example, may be reinforced with carbon fiber, fiberglass or the like.

Referring now to FIGS. 4A-4E, one embodiment of a method for modifying tissue using flexible tissue modification device 10 is demonstrated in greater detail. In these figures, a patient's skin, target tissue TT and non-target tissue NTT are shown diagrammatically, rather than as specific structures. In one embodiment, the method of FIGS. 4A-4E may be employed in the spine, to remove ligamentum flavum, bone or both, with device 10 passing through an intervertebral foramen between two vertebrae, as shown in FIG. 2A. In other embodiments, other tissue in other areas of the body may be removed.

Figure 4A:
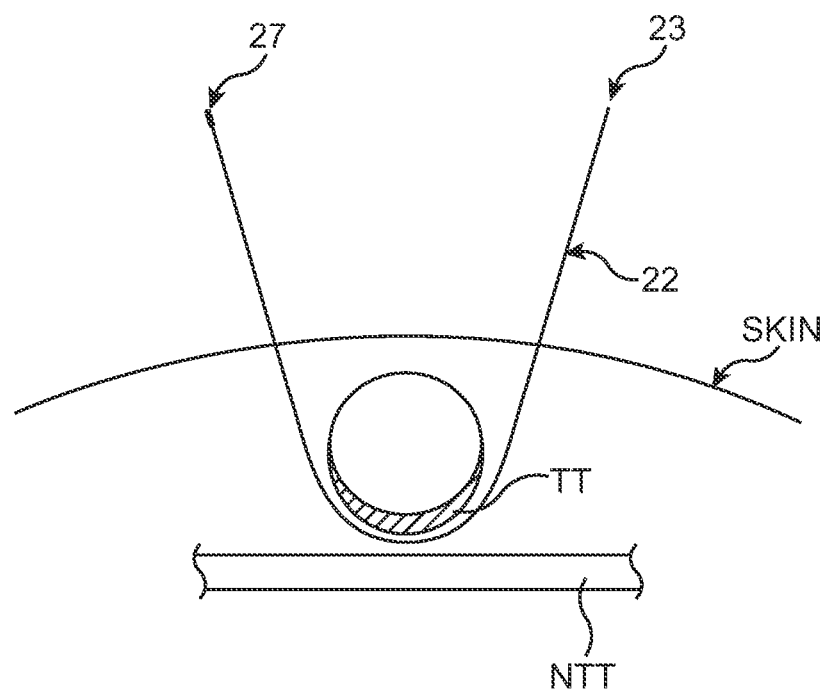
FIGS. 4A-4E demonstrate a method for inserting and using a flexible tissue modification device to modify tissue while inhibiting damage to non-target tissue, according to one embodiment of the present invention.

As shown in FIG. 4A, guidewire 22 with sharp tip 23 and shaped end 27 may be passed into the skin, between target and non-target tissue, and out of the skin. Methods for passing guidewire 22 are described further, for example, in U.S. patent application Ser. Nos. 11/457,416, 11/468,247 and 11/468,252, which were previously incorporated by reference. As described in those references, in various embodiments, guidewire 22 may be placed using a percutaneous method, such as with a needle, or using an open method, such as with a probe. In some embodiments, localization of neural tissue, such as with nerve stimulation on a guidewire passing probe or guidewire passing guide member may be used, to confirm that guidewire 22 is passed between target and non-target tissue.

In some embodiments where the method is performed in the spine, one or more substances or devices may be placed into the epidural space of the spine before or after placing guidewire 22, to create additional space between target tissues, such as ligamentum flavum, and non-target tissues, such as cauda equina and nerve root. Substances may include, for example, any of a number of fluids or gels, such as radiographic contrast medium. Devices may include, for example, a barrier or shield device. Injection of substances into the epidural space to create a safety zone is described in U.S. patent application Ser. No. 11/193,557 (Pub. No. 2006/0036211), titled "Spinal Ligament Modification Kit," assigned to X-Sten, Inc., and filed Jul. 29, 2005, the full disclosure of which is hereby incorporated by reference. Various barrier devices for placement in the spine are described, for example, in U.S. patent application Ser. No. 11/405,859, titled "Tissue Modification Barrier Devices and Methods," and filed Apr. 17, 2005, the full disclosure of which is hereby incorporated by reference.

Figure 4B:
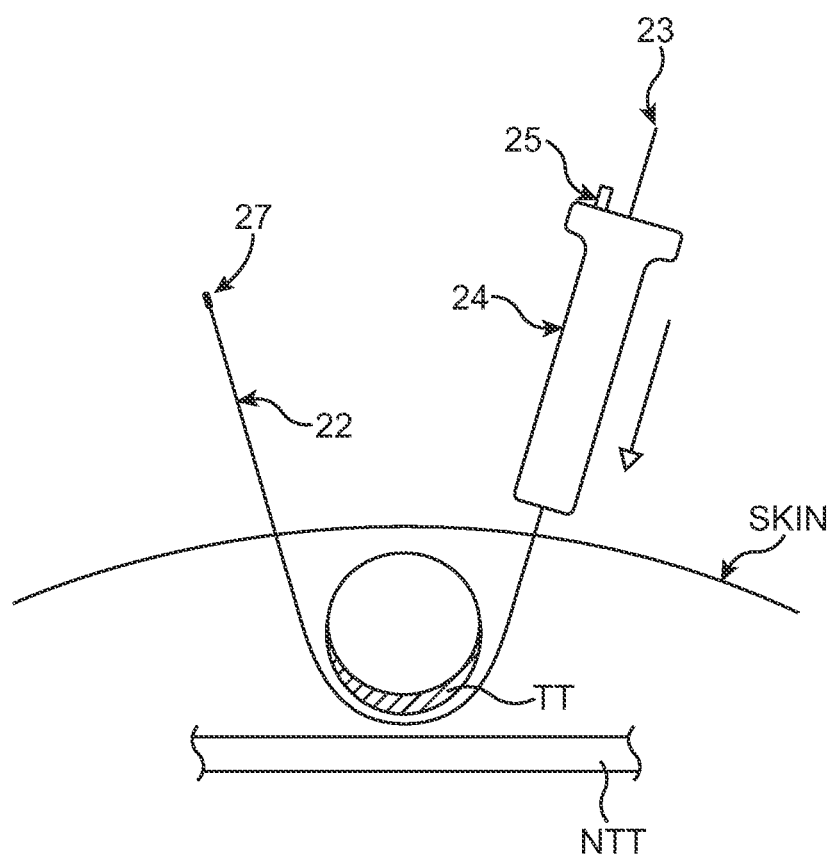

Referring to FIG. 4B, distal handle 24 may be passed over sharp tip 23 and tightened around guidewire 22, such as by moving tightening lever 25. Distal handle 24 may be coupled with guidewire 22 at this point in the process or at a later point, according to various embodiments.

Figure 4C:
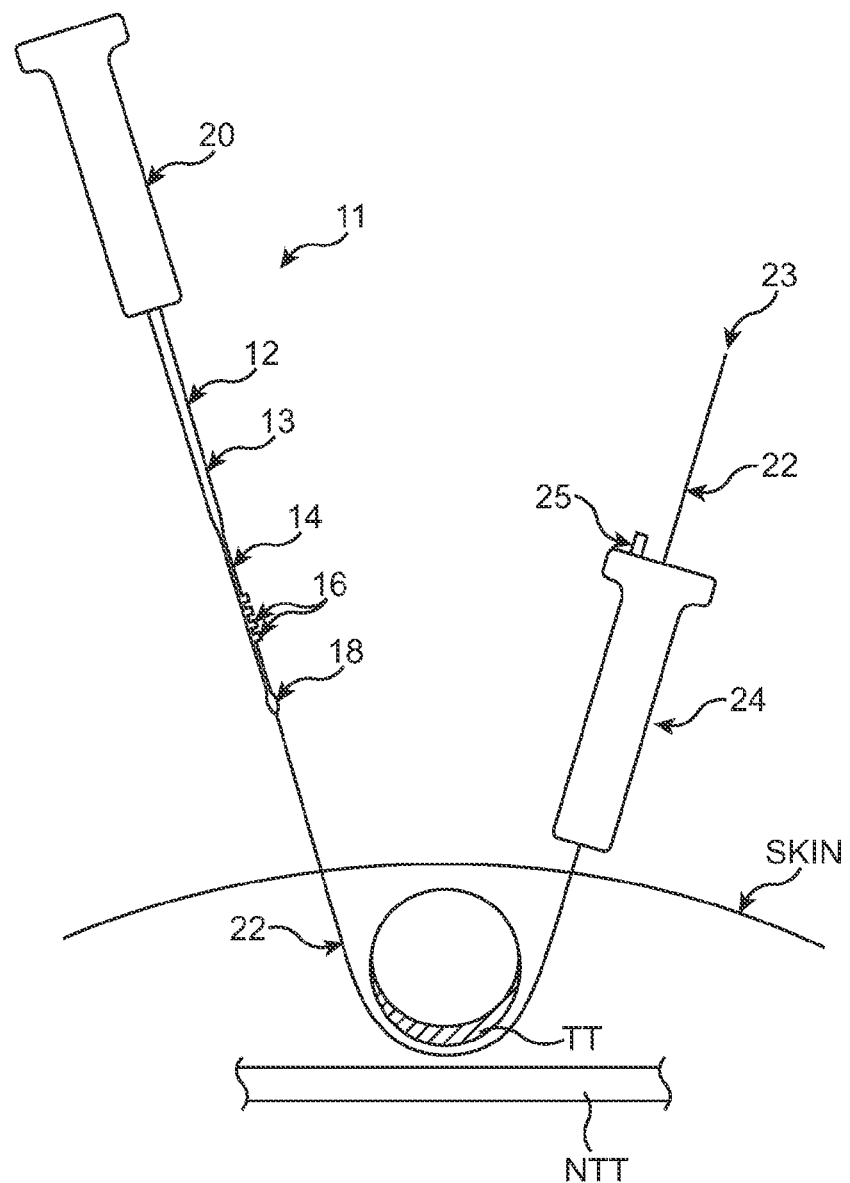

As shown in FIG. 4C, guidewire 22 may next be coupled with proximal device portion 11, by coupling shaped guidewire end 27 (not visible) with guidewire coupler 18. In the embodiment shown, for example, guidewire shaped end 27 may be placed into coupling member 18 (hollow-tipped arrow).

Figure 4D:
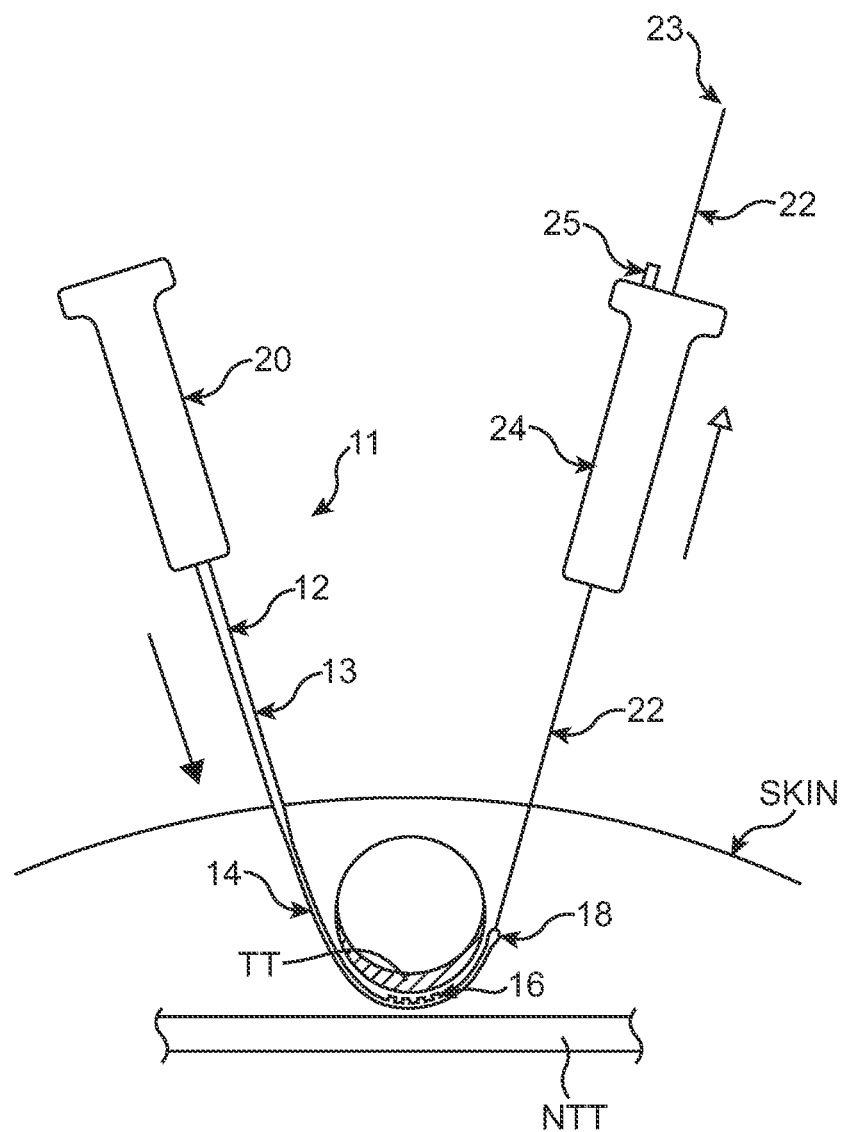

Referring to FIG. 4D, distal handle 24 may then be pulled (hollow-tipped arrow) to pull device 10 into the patient and to thus position tissue modifying members 16 in contact with target tissue TT. In some embodiments, such as when device 10 is used in a spinal procedure and passes through an intervertebral foramen, a surgeon or other physician user may use tactile feedback of device 10 passing into the foramen, such as when coupling member 18 and/or tissue modifying members 16 pass into the foramen, to determine when tissue modifying members 16 are positioned in a desired location relative to target tissue TT. Alternatively or additionally, a surgeon may confirm that a desired placement has been achieved by using radiographic imaging, such as fluoroscopy, direct visualization, such as in an open surgical case, or a combination of multiple methods.

In some embodiments in which device 10 is used in the spine to treat spinal stenosis and/or neural or neurovascular impingement, device 10 may be passed into the patient and to a position for modifying tissue without removing any vertebral bone. More specifically, in some embodiments, device 10 may be advanced into the patient, through an intervertebral foramen, and out of the patient without removing bone. This is contrary to the majority of current surgical methods for treating spinal stenosis, which typically include removal of at least some vertebral bone, such as performing a laminotomy or laminectomy, and which often remove significant amounts of vertebral lamina, spinous process, facet and/or pedicle bony tissue, simply to access the surgical site. In one embodiment, for example, device 10 may be advanced percutaneously into the patient, used to remove ligamentum flavum only, and withdrawn from the patient, without removing any vertebral bone.

Figure 4E:
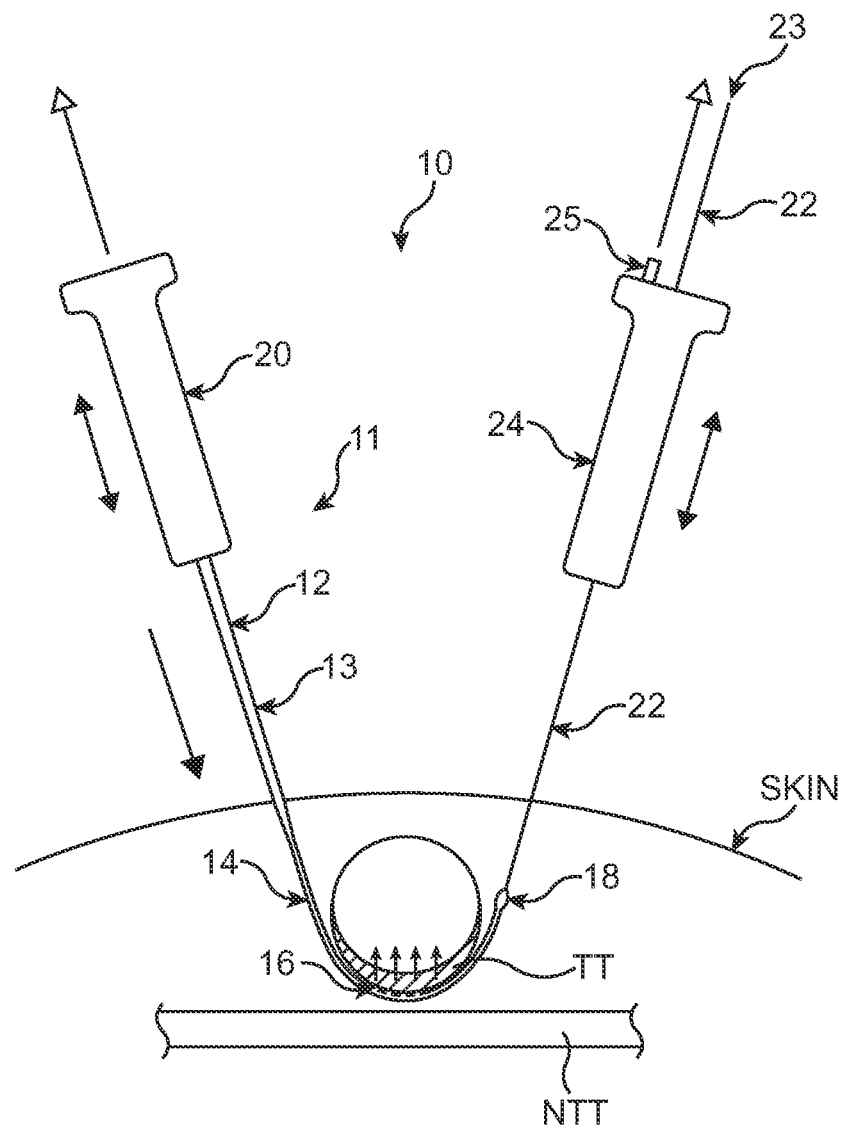

As shown in FIG. 4E, once tissue modifying members 16 are positioned as desired, relative to target tissue TT, proximal handle 20 and guidewire handle 24 may be pulled (hollow-tipped arrows) to urge tissue modifying members 16 against target tissue TT (solid-tipped arrows). While maintaining pulling/tensioning force, handles 20, 24 may be used to reciprocate device 10 back and forth (solid-tipped, double-headed arrows) to remove target tissue TT. During a procedure, rigid proximal shaft portion 13 may be used to help steer device 10, or more specifically flexible distal shaft portion 14, relative to the target TT. For example, rigid shaft portion 13 may be used to move flexible portion 14 laterally or to pivot shaft 12 about an axis located along flexible portion 14. In one embodiment, for example, rigid portion 13 may be used to manipulate flexible portion 14 within an intervertebral foramen, such as by pivoting shaft 12 or moving flexible portion 14 laterally in a caudal and/or cephalad direction, relative to the patient. The rigidity of rigid proximal shaft portion 13 may generally facilitate such steering, as compared to a completely flexible device.

When a desired amount of tissue is removed, device 10 may be removed from the patient, such as by detaching guidewire handle 24 from guidewire 22 and pulling proximal handle 20 to withdraw device 10 and guidewire 22 out of the patient. In some embodiments, device 10 or an additional device may be reinserted into the patient and used in a second location to remove additional tissue. For example, in a spinal stenosis treatment procedure, device 10 may be used to remove tissue from (and thus decompress) a first intervertebral foramen and then may be removed and reinserted to remove tissue from a second foramen. This process may be repeated to remove tissue from any number of foramina. In one embodiment, device 10 may include a guidewire lumen, so that a guidewire may be placed into a second foramen while device 10 is in the epidural space of the patient. Device 10 may then be removed along with the first guidewire 22, attached to the second guidewire, and reinserted into the second foramen to remove tissue. In some embodiments, tissue may be removed from device 10 before reinserting device 10 into the patient to remove more tissue.

Figure 5A:
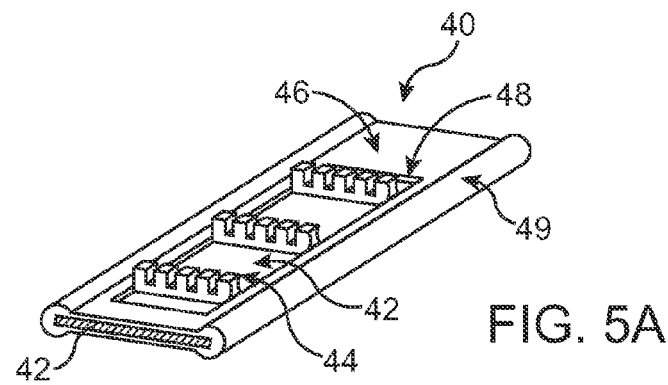
FIG. 5A is a perspective view of a flexible portion of a tissue modification device, according to one embodiment of the present invention.
Figure 5B:
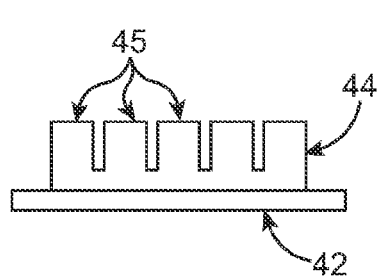
FIGS. 5B and 5C are end-on and side views of blade and substrate portions of the portion of the device of FIG. 5A.
Figure 5C:
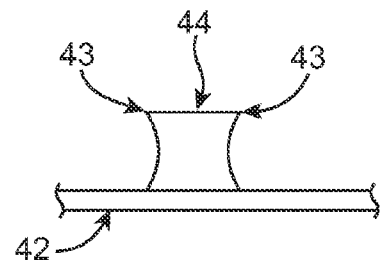

Referring now to FIGS. 5A-5C, a flexible distal portion 40 of a flexible tissue modification device is shown, in various views. In FIGS. 5A-5C and 6-25, various alternative embodiments of a flexible distal portion of a tissue modification device are shown in a generally straight configuration. However, all embodiments shown are flexible and thus may assume a curved configuration. The embodiments are shown in straight configuration for ease of illustration only.

In one embodiment, flexible distal portion 40 may include a substrate 42 (or "flexible, distal shaft portion"), multiple tissue modifying members 44 coupled with substrate 42, and an atraumatic cover 46 disposed over substrate 42 and forming an aperture 48 and atraumatic bumpers 49. FIG. 5B is an end-on view of substrate 42 and one of cutting members 44, which includes multiple teeth 45. FIG. 5C is a side view of substrate 42 and one of cutting members 44, showing that each cutting member 44 has two cutting edges 43 in this embodiment.

The embodiment of FIG. 5A includes three cutting members 44 comprising blades with multiple teeth 45 with grooves between them. Cutting members 44 in this and other embodiments may include any suitable material, such as the materials listed previously above. Any number of cutting members 44 may be used, such as from one to twenty cutting members in various embodiments. Cutting members 44 may have any suitable height and my be spaced apart from one another at any suitable distances. In one embodiment, for example, cutting members 44 may have a height designed to protrude just slightly above the height of bumpers 49, so that cutting members 44 can cut tissue but do not protrude so high as to inhibit advancement or positioning of device in the patient. In some embodiments, cutting members 44 may be constructed as separate pieces and attached to substrate 42, such as by welding or gluing with adhesive. In some embodiments, cutting members 44 may be built by stacking layers of material to one another and attaching the stacks to form one piece. Cover 46 may be coupled with substrate using any known or later invented manufacturing technique, such as thermoforming, injection molding, or the like.

in various alternative embodiments of distal portion 40 of FIGS. 5A-5C, as well as in all embodiments described below and alternatives thereto, any number of cutting members 44 may be used, cutting members 44 may be made of any suitable material, and cutting members may be disposed along substrate 42 in any configuration, pattern or the like. Therefore, various alternative materials, numbers, patterns and the like of cutting members 44 will not be listed repeatedly for each alternative embodiment.

Figure 6:
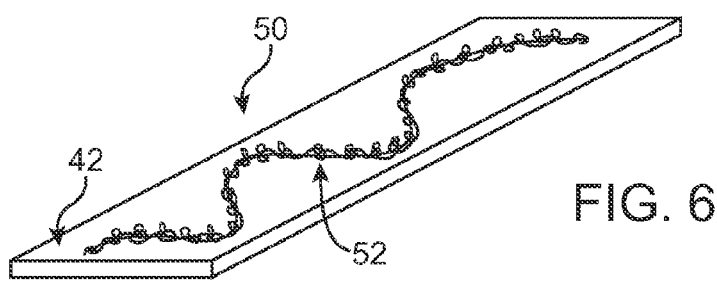
FIG. 6 is a perspective view of a portion of a flexible substrate and a wire saw tissue modifying member of a tissue modification device, according to one embodiment of the present invention.

Referring now to FIG. 6, in another embodiment, a distal portion of a flexible tissue modification device 50 may include substrate 42 and a wire saw 52 coupled with substrate 42, such as by welding. In FIG. 6, as well as in subsequent FIGS. 7-18, only a portion of each device embodiment including substrate 42 and one or more cutting members is shown, to simplify the drawing figures and description. Any of these embodiments may also include an atraumatic cover and/or other features, but for simplicity's sake, these features are not shown. Referring to the embodiment of FIG. 6, wire saw 52 may comprise any wire saw currently known or later invented, such as a Gigli saw, and may be attached to substrate 42 in any suitable pattern or configuration, such as in an S-shape pattern, as shown, or a zig-zag, straight-line or other pattern.

Figure 7:
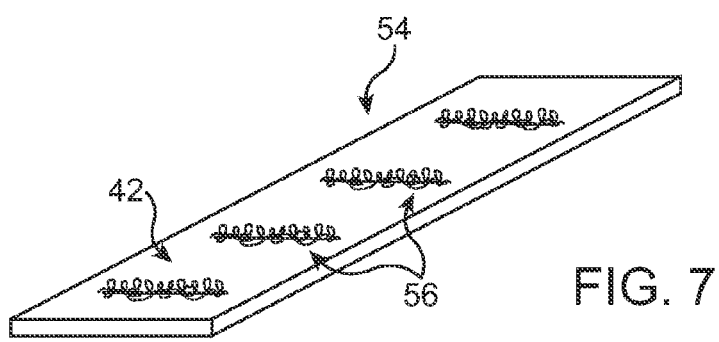
FIG. 7 is a perspective view of a portion of a flexible substrate and multiple wire saw tissue modifying members of a tissue modification device, according to an alternative embodiment of the present invention.

With reference to FIG. 7, in an alternative embodiment, a distal portion of a flexible tissue modification device 54 may include multiple pieces of wire saw 56 coupled with substrate 42. Again, these pieces of saw 56 may be attached in any pattern and by any means, such as by welding, and may comprise Gigli saw or other types of wire saw.

Figure 8:
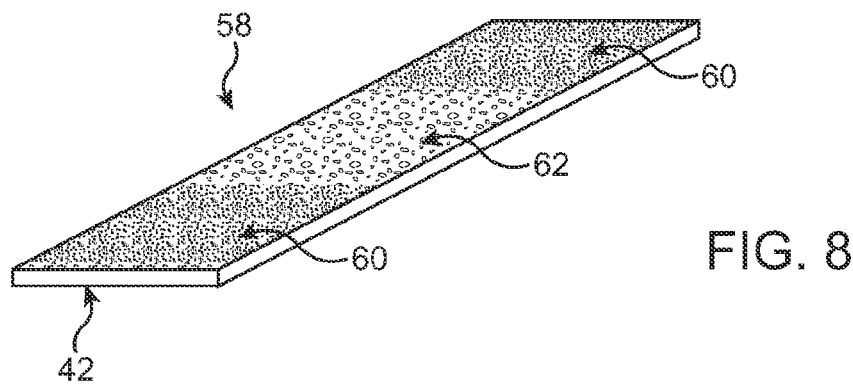
FIG. 8 is a perspective view of a portion of a flexible substrate and an abrasive surface tissue modifying member of a tissue modification device, according to an alternative embodiment of the present invention.

FIG. 8 shows a portion of another alternative embodiment of a flexible tissue modification device 58, in which abrasive materials 60, 62 are adhered to a surface of substrate. In some embodiments, only one type and/or grain of abrasive material 60 or 62 may be used, while other embodiments may include multiple types of material, multiple grains of material, or both. For example, in the embodiment shown, a finer grain of material 60 may be disposed at either end of a portion of coarser grain material 62. Such a variation in grains may provide varying degrees of tissue modification and/or the ability to remove greater amounts of tissue with a coarser grain 62 and provide a smoother finished surface to the tissue with the finer grain 60. In various embodiments, any abrasive materials 60, 62 may be used, and the materials may be adhered to substrate 42 via any method, such as adhering with adhesive or the like. One embodiment, for example, may include abrasive materials such as those described in U.S. patent application Ser. No. 10/277,776 (Pub. No. 2003/0225412), titled "Surgical Ribbon File," and filed Oct. 21, 2002, the full disclosure of which is hereby incorporated by reference. In another embodiment, substrate 42 may be treated in such a way as to have an abrasive surface, such as by sand blasting.

Figure 9:
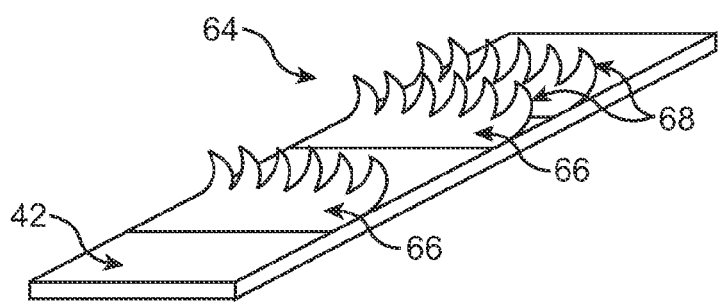
FIG. 9 is a perspective view of a portion of a flexible substrate and multiple tooth-like tissue modifying members of a tissue modification device, according to an alternative embodiment of the present invention.

Referring to FIG. 9, in another alternative embodiment, a flexible tissue modification device 64 may include multiple tissue modifying members 66, each including multiple, curved teeth 68. Cutting members 66 may be made of stainless steel or other material(s). In some embodiments, cutting members 66 may be configured to primarily cut and/or shred ligamentous tissue, such as ligamentum flavum.

Figure 10:
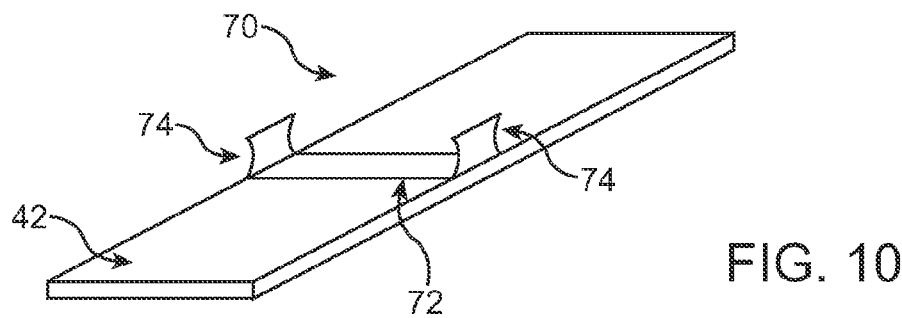
FIG. 10 is a perspective view of a portion of a flexible substrate and a two-blade tissue modifying member of a tissue modification device, according to an alternative embodiment of the present invention.

Referring to FIG. 10, in another alternative embodiment, a flexible tissue modification device 70 may include one tissue modifying member 72 with vertically oriented blades 74 at opposite ends. Blades 74 may be designed, in one embodiment, specifically for cutting or slicing ligamentous tissue, such as ligamentum flavum.

Figure 11:
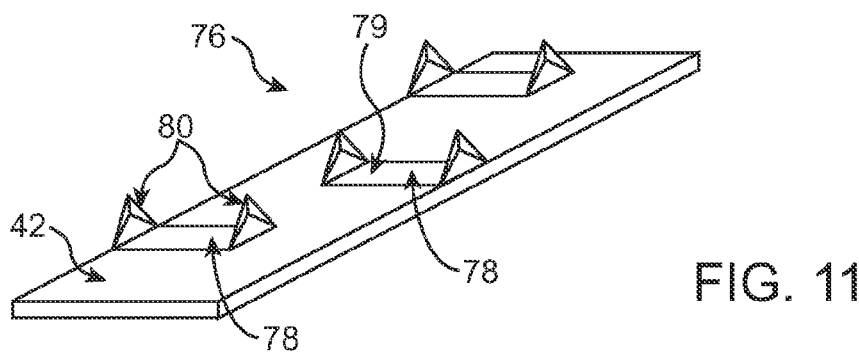
FIG. 11 is a perspective view of a portion of a flexible substrate and multiple shark-tooth-shaped tissue modifying members of a tissue modification device, according to an alternative embodiment of the present invention.

Referring to FIG. 11, in another alternative embodiment, a flexible tissue modification device 76 may include multiple tissue modifying members 78, each with vertically oriented blades 80 at opposite ends. Blades 80 may each have a sharktooth shape, with sharp edges on opposite sides. In one embodiment, blades 80 may be designed specifically for cutting or slicing ligamentous tissue, such as ligamentum flavum. Alternatively, or additionally, blades 80 may be configured to cut bone. In one embodiment, each blade 80 may have a height approximately equal to or greater than a thickness of a ligamentum flavum. Such a blade 80 may be positioned in the spine to extend through ligamentum flavum and contact bone. When reciprocated, such a blade 80 may cut ligamentum flavum alone or may cut ligamentum flavum tissue and then, when it is removed, may also cut bone. Such a blade height and configuration may facilitate lateral steering of device 76.

Figure 12:
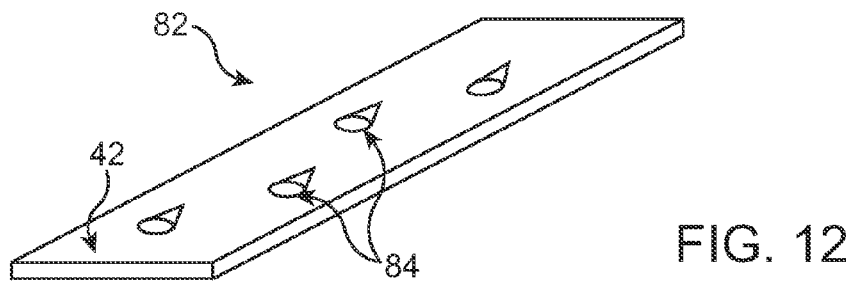
FIG. 12 is a perspective view of a portion of a flexible substrate and multiple cheese-grater-shaped tissue modifying members of a tissue modification device, according to an alternative embodiment of the present invention.

Referring to FIG. 12, in another alternative embodiment, a flexible tissue modification device 82 may include multiple tissue modifying members 84 formed as holes in substrate 42 with raised edges, such as are found on a cheese grater. The raised edges of cutting members 84 may be sharp, to provide cutting. Any number of tissue modifying members 84 my be included, they may have any desired size, and they may be formed on substrate in any pattern. In some embodiments, cut tissue may pass through the holes of cutting members 84 and thus through substrate 42. In some embodiments, a tissue capture device or member may be coupled with the back side of substrate 42 to collect cut tissue that passes through cutting members 84.

Figure 13:
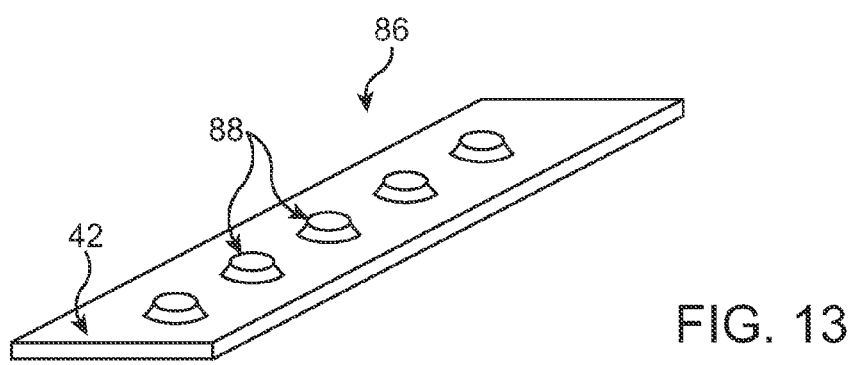
FIG. 13 is a perspective view of a portion of a flexible substrate and multiple raised tissue modifying members of a tissue modification device, according to an alternative embodiment of the present invention.

Referring to FIG. 13, in another alternative embodiment, a flexible tissue modification device 86 may include multiple tissue modifying members 88 formed as upward-facing holes in substrate 42. The raised edges of cutting members 88 may be sharpened, to provide cutting. Any number of tissue modifying members 88 may be included. In some embodiments, cut tissue may pass through the holes of cutting members 88 and thus through substrate 42. In some embodiments, a tissue capture device or member may be coupled with the back side of substrate to collect cut tissue that passes through cutting members 88.

Figure 14:
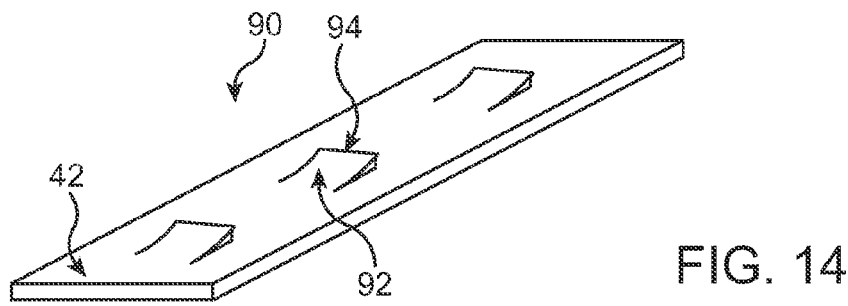
FIG. 14 is a perspective view of a portion of a flexible substrate and multiple raised-flap tissue modifying members of a tissue modification device, according to an alternative embodiment of the present invention.

Referring to FIG. 14, in another alternative embodiment, a flexible tissue modification device 90 may include multiple tissue modifying members 92 formed as raised flaps in substrate 42, with each flap 92 including a sharpened cutting edge 94. Any number of tissue modifying members 92 may be included. In some embodiments, cut tissue may pass underneath the flap-like cutting members 92 and thus through substrate 42. In some embodiments, a tissue capture device or member may be coupled with the back side of substrate to collect cut tissue that passes through cutting members 92.

Figure 15:
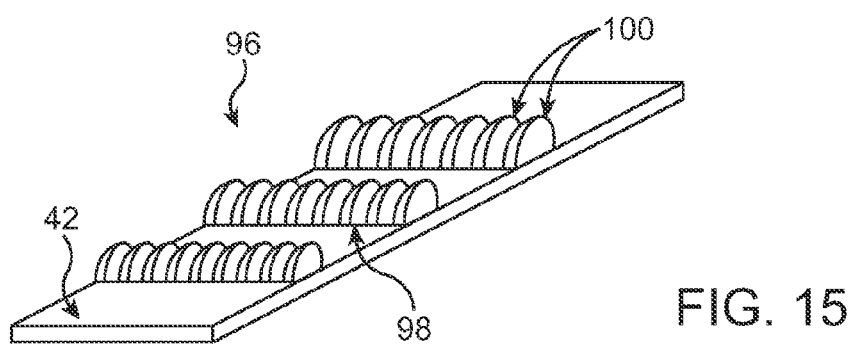
FIG. 15 is a perspective view of a portion of a flexible substrate and multiple rounded tissue modifying members of a tissue modification device, according to an alternative embodiment of the present invention.

Referring to FIG. 15, in another alternative embodiment, a flexible tissue modification device 96 may include multiple tissue modifying members 98 formed as rounded cutting devices coupled with substrate 42. In one embodiment, each cutting member 98 may include multiple ridges, divided by grooves. In one embodiment, cutting members 98 may have a spiral or screw-like configuration.

Figure 16:
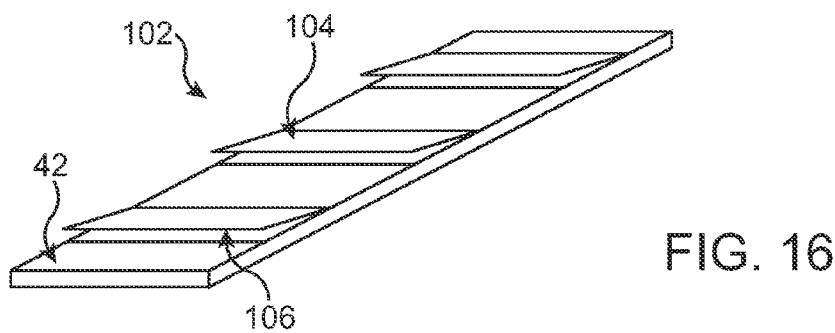
FIG. 16 is a perspective view of a portion of a flexible substrate and multiple raised-flap tissue modifying members of a tissue modification device, according to an alternative embodiment of the present invention.

Referring to FIG. 16, in another alternative embodiment, a flexible tissue modification device 102 may include multiple tissue modifying members 104 comprising thin, flap-like blades coupled with substrate 42, each cutting member 104 including a sharp blade edge 106. Any number, size and configuration of blades may be used.

Figure 17:
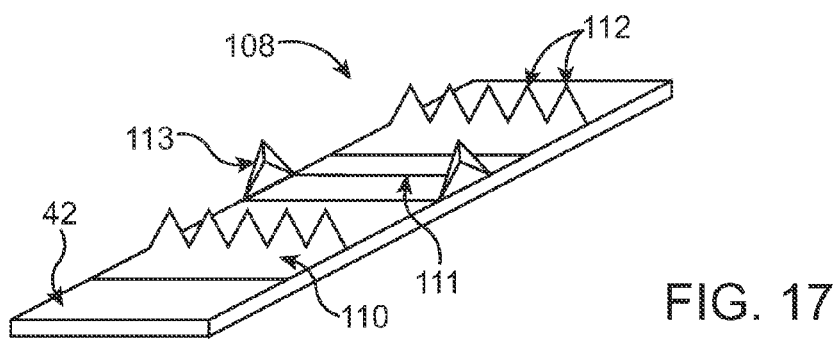
FIG. 17 is a perspective view of a portion of a flexible substrate and multiple, differently shaped tissue modifying members of a tissue modification device, according to an alternative embodiment of the present invention.

Referring to FIG. 17, in another alternative embodiment, a flexible tissue modification device 108 may include multiple different types of tissue modifying members 110, 111. For example, one embodiment may include one or more jagged tissue cutters 110 each having multiple, triangular, raised teeth 1112, and one or more bladed tissue cutters 111, each having multiple blades 113. Teeth 112 and/or blades 113 may be configured specifically to cut ligamentum flavum tissue, bone, or both, in various embodiments.

Figure 18:
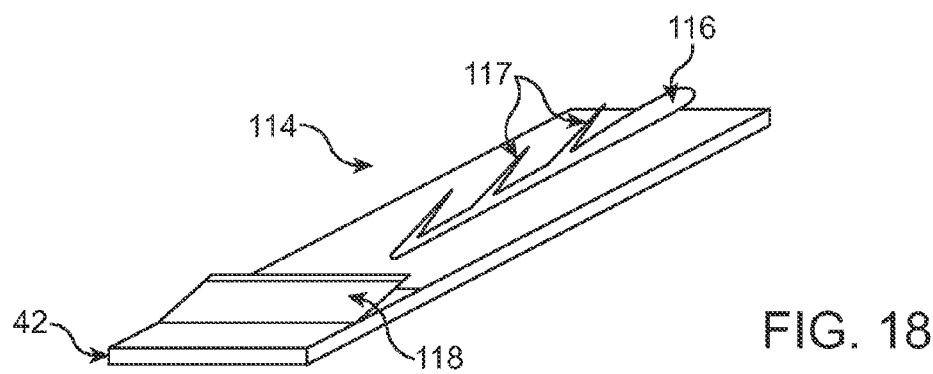
FIG. 18 is a perspective view of a portion of a flexible substrate and barbed-hook and raised-flap tissue modifying members of a tissue modification device, according to an alternative embodiment of the present invention.

Referring to FIG. 18, in another alternative embodiment, a flexible tissue modification device 114 may include substrate 42, a tissue engaging member 116 including multiple barbs 117 for hooks, needles or the like), and one or more tissue cutting members 118, such as a raised blade. In various embodiments, tissue engaging member 116 may be configured to hook, snag, grab or otherwise engage soft tissue, such as ligamentum flavum, and pull or stretch such tissue as it is pulled or pushed across the tissue. Tissue cutting member 118 may follow behind tissue engaging member 116 and cut the stretched/pulled tissue. Such stretching or pulling of tissue before cutting may facilitate or enhance tissue cutting.

Figure 19:
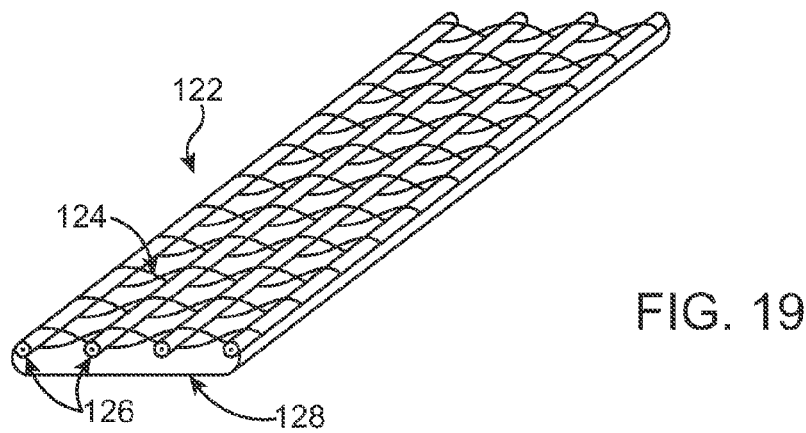
FIG. 19 is a perspective view of a portion of a wire mesh flexible tissue modification device, according to an alternative embodiment of the present invention.

Referring to FIG. 19, in another alternative embodiment, a flexible tissue modification device 122 may include a wire mesh 124 coupled with multiple supporting structures 126 and an atraumatic material 128 on one side. All components may be made of any suitable material, such as those listed previously.

Figure 20:
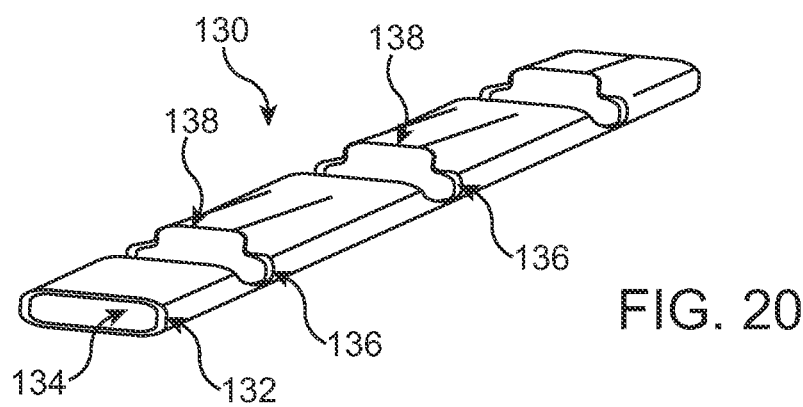
FIG. 20 is a perspective view of a portion of a flattened, hollow, flexible tissue modification device, according to an alternative embodiment of the present invention.

Referring to FIG. 20, in another alternative embodiment, a flexible tissue modification device 130 may comprise a hollow, flattened shaft 132, having central chamber or lumen 134, into which multiple grooves 136 may be cut. An edge of each groove 136 may be raised and sharpened to form a blade edge 138, thus forming a multiple, bladed tissue modifying members. Tissue cut by blades 138 may pass under blades 138 to collect within lumen 134 and may thus be transported out of the patient.

Figure 21:
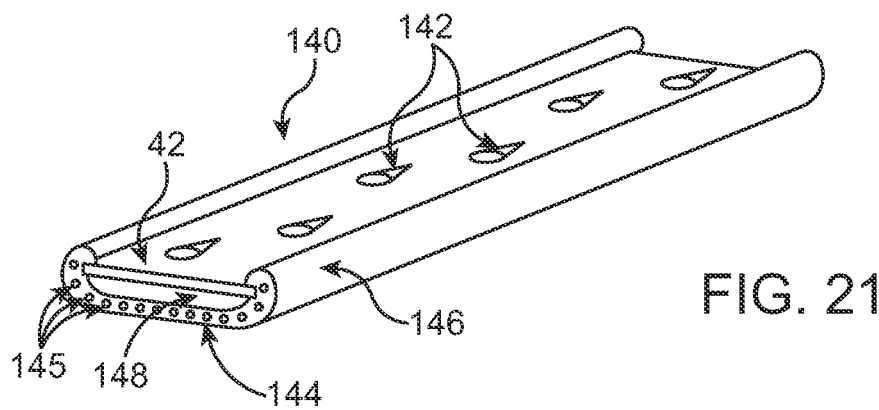
FIG. 21 is a perspective view of a portion of a flexible substrate and cheese-grater-shaped tissue modifying members coupled with a tissue capture member of a tissue modification device, according to an alternative embodiment of the present invention.

Referring to FIG. 21, in another alternative embodiment, a flexible tissue modification device 140 may include multiple tissue modifying members 142 formed as holes in substrate 42 with raised edges, such as are found on a cheese grater. The raised edges of cutting members 142 may be sharpened, to provide cutting. Any number of tissue modifying members 142 may be included. In some embodiments, cut tissue may pass through the holes of cutting members 142 and thus through substrate 42. In some embodiments, a tissue collection member 144, forming a tissue collection chamber 148, may be coupled with the back side of substrate 42 to collect cut tissue that passes through cutting members 142. Tissue collection member 144 may also serve as an atraumatic tissue protection member and may include, for example, side bumpers 146 to avoid damaging non-target tissue with sharp edges of device 140. In some embodiments, tissue collection member 144 may be strengthened by multiple fibers 145, such as wires or carbon fibers.

Figure 22:
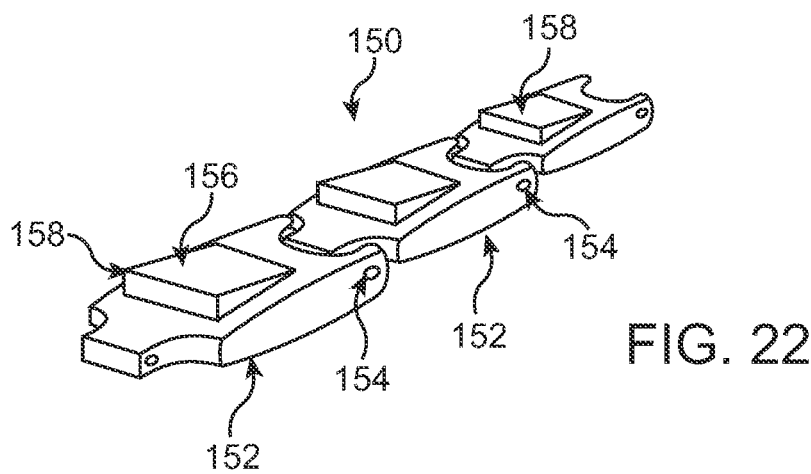
FIG. 22 is a perspective view of a portion of a moveable-link flexible tissue modification device, according to an alternative embodiment of the present invention.

Referring to FIG. 22, in another alternative embodiment, a flexible tissue modification device 150 may include multiple sections 152 linked together via linkages 154 to form a flexible device configuration analogous to that of some watch bands. A tissue modifying member 156 having a cutting edge 158 may be disposed on one side of each section 152 to cut tissue.

In various embodiments, any given flexible tissue modification device may act on tissue in a number of different ways, such as by cutting, ablating, dissecting, repairing, reducing blood flow in, shrinking, shaving, burring, biting, remodeling, biopsying, debriding, lysing debulking, sanding, filing, planing, heating, cooling, vaporizing, delivering a drug to, and/or retracting target tissue. For example, many of the devices described above may also optionally be loaded with a drug, bone wax, gel foam, or the like, which may be deposited during a tissue modification procedure. Any suitable drug may be delivered via the devices in various embodiments, such as but not limited to thrombin, NSAID, local anesthetic or opioid. In some embodiments, devices may also deliver an implant, such as a stent-like implant for maintaining patency of decompressed intervertebral foramen, a rivet, staple or similar device for retracting ligamentum flavum tissue, a tissue dressing, or the like. In some embodiments, devices may cool or freeze tissue for analgesia or to change the tissue's modulus of elasticity to facilitate tissue modification. Some embodiments of devices may also include a visualization and/or diagnostic component, such as an ultrasound, MRI, reflectance spectroscopy, fiber optic, endoscope, charge-coupled device (CCD), complementary metal-oxide semiconductor (CMOS) or other device.

Any of the devices described herein may also optionally include one or more components for neural identification and/or localization. For example, in some embodiments, a flexible tissue modification device may include one or more nerve stimulation electrodes on a backside or underside of the device (i.e., a side designed to be atraumatic and face non-target tissue). The electrode(s) may be used to confirm that the atraumatic side of the device is in contact with non-target neural tissue, thus also confirming that the tissue modification members of the &vice are facing target tissue. In some embodiments, the devices may also include one or more electrodes on an upper surface, at or near the tissue modification members, to further confirm a desired placement of the device. For further description of such neural localization devices and methods, reference may be made to U.S. patent application Ser. No. 11/457,416, which was previously incorporated by reference.

Figure 23:
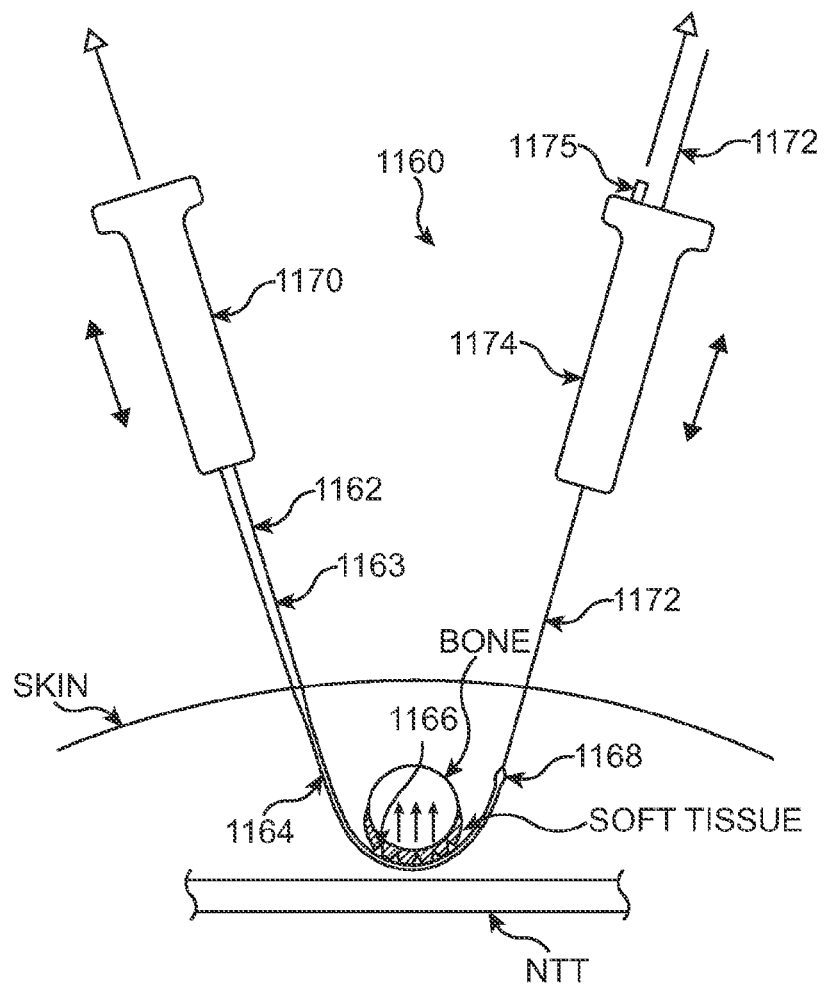
FIG. 23 is a side view of a tissue modification device in a position for performing a tissue modification procedure, showing a generic bone, soft tissue and non-target tissue, according to one embodiment of the present invention.

With reference now to FIG. 23, in another alternative embodiment, a tissue modification device 1160 may suitably include a proximal handle 1170 coupled with an elongate body 1162 (or "shaft") having a proximal, rigid shaft portion 1163 and a distal, flexible portion 1164 from which multiple blades 1166 may extend. A guidewire coupler 1168 may be formed in (or attached to) flexible portion 1164 at or near its distal end for coupling with a guidewire 1172, which in turn may be coupled with a guidewire handle 1174 (or "distal handle"). Distal handle 1174 may include a tightening lever 1175 for tightening handle 1174 around guidewire 1172. In one embodiment, device 1160 may have many of the characteristics and be used in much the same way as embodiments described above.

In FIG. 23, device 1160 is shown passing into a patient, along a curved path between a generic soft tissue/bone combination and nearby non-target tissue NTT, and back out of the patient. In one embodiment, device 1160 may be passed into a patient, through an intervertebral space of the patient's spine (between ligamentum flavum and neural/neurovascular tissue), and back out of the patient, as described in detail above with reference to alternative embodiments. Once device 1160 is in place for modifying a target tissue, such as soft tissue and/or bone, handles 1170, 1174 may be pulled (hollow-tipped arrows) to apply force and thus urge blades 1166 into soft tissue (single-headed, solid-tipped arrows). Device 1160 may then be reciprocated (double-headed, solid-tipped arrows), while maintaining some or all of the pulling force, to remove or otherwise modify the target soft tissue and/or bone. As mentioned previously, before reciprocating device 1160 to remove tissue, in some embodiments the device may be used to stimulate nearby nerve tissue, such as with an electrode coupled with the back and/or front side(s) of flexible portion 1164. Such nerve stimulation may help confirm that device 1160 has been placed in a desired location for treatment and may be monitored using electromyography (EMG), visual observation of muscle twitch and/or the like.

Referring to FIG. 24, in one embodiment a tissue modification device 1180 may include a proximal handle 1189 coupled with one end of an elongate body 1182, which includes a proximal rigid shaft portion 1183 and a distal flexible portion 1184. Multiple blades 1186, 1186' extend from a first side of flexible portion 1184, while a second side approximately opposite the first side is substantially atraumatic to inhibit damage to non-target tissues during a tissue modification procedure. Flexible portion 1184 may also include a guidewire coupler 1188 at its distal end. In various embodiments, a suitable combination of blades 1186, 1186' may be included on a given tissue modification device. For example, device 1180 includes four pointed-tip blades 1186 and two flat-top blades 1186'. Various blades may be configured to perform one or more of a number of functions. For example, pointed-tip blades 1186 may be ideal for eating through soft tissue and bone, while flat-top blades 1186' may be best for cutting through soft tissue and riding along a bone surface to help steer or guide device 1180. In some embodiments, all blades on a device may be configured for optimal soft tissue cutting, such as cutting of ligamentum flavum tissue in the spine, while in other embodiments all blades may be configured for optimal bone cutting, such as vertebral bone. Other alternative embodiments may include a combination of blade shapes and configurations to provide multiple different types of cutting. Further discussion of blades combinations and configurations are included in application Ser. No 11/687,558, filed Mar. 16, 2007, and entitled "Flexible Tissue Removal Devices and Methods", the full disclosure of which is incorporated herein by reference.

With reference now to FIG. 25, a perspective view of a portion of an alternative embodiment of a tissue modification device 1190 shows a rigid shaft portion 1193 extending to a flexible portion 1194 with pointed-tip blades 196, flat-top blades 1196', and a guidewire coupler 1198. In the embodiment shown, and as is described in further detail below in relation to another embodiment, some or all blades 1196' may be angled, relative to a longitudinal axis of the elongate body and flexible portion 1194 of device 1190. Angling blades 1196' may cause or facilitate lateral movement of device 1190 along a target tissue as device 1190 is reciprocated back and forth to modify the tissue, thus providing for wider or more complete tissue modification/removal.

Figure 26A:
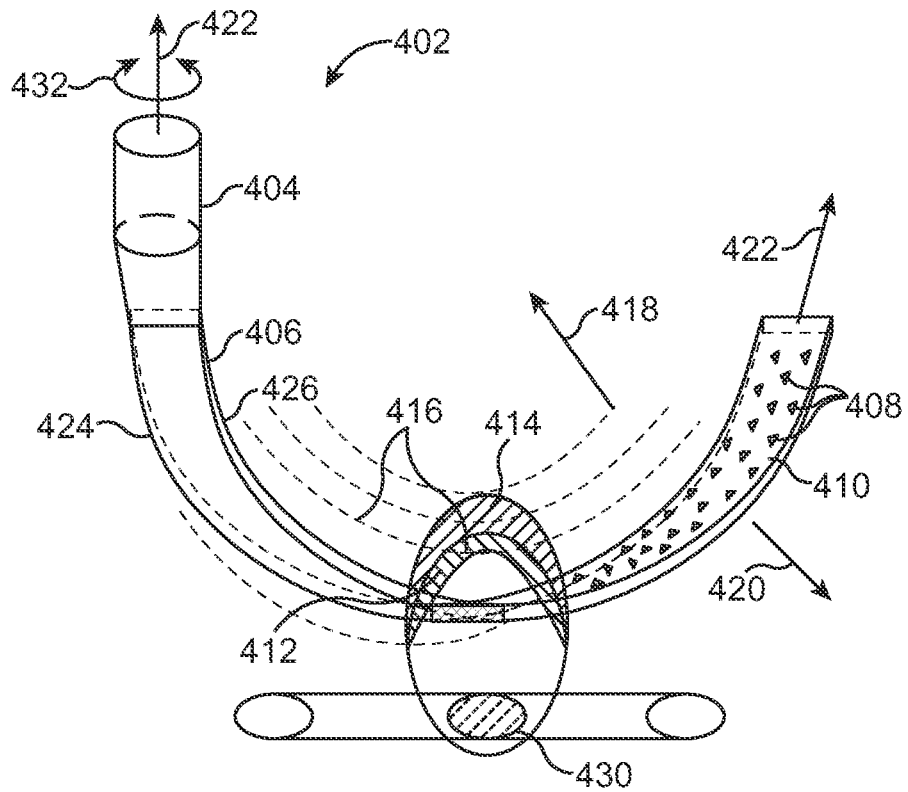
FIGS. 26A and 26B illustrate how tension in a flexible portion of a tissue modification device bent over a target tissue can urge blades or other tissue modification devices into the target tissue, and how torque to the rigid portion of the tissue modification device can maintain or alter an orientation of the flexible member and inhibit flipping of the flexible member.
Figure 26B:
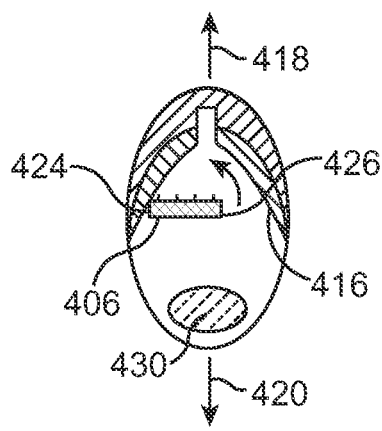
Figure 40:
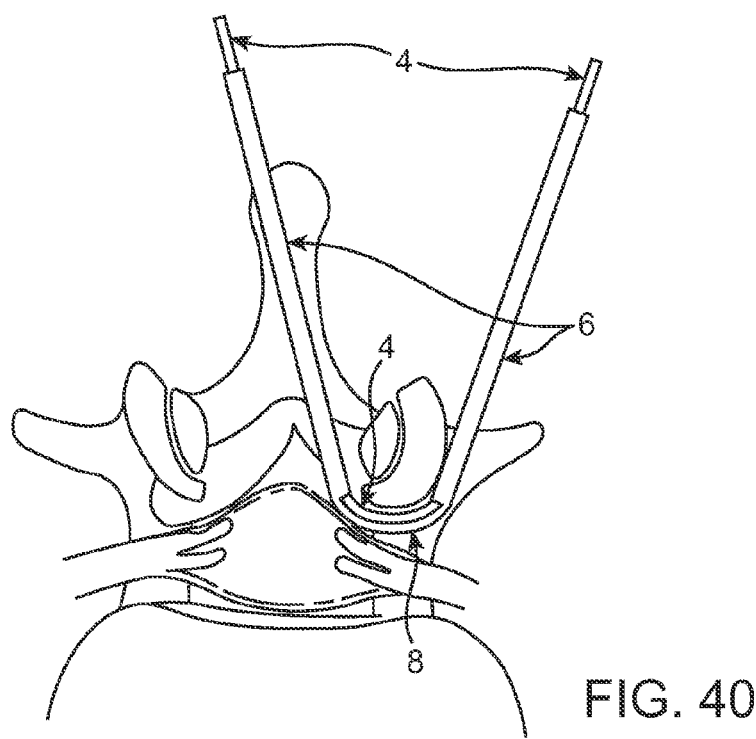
Figure 41:
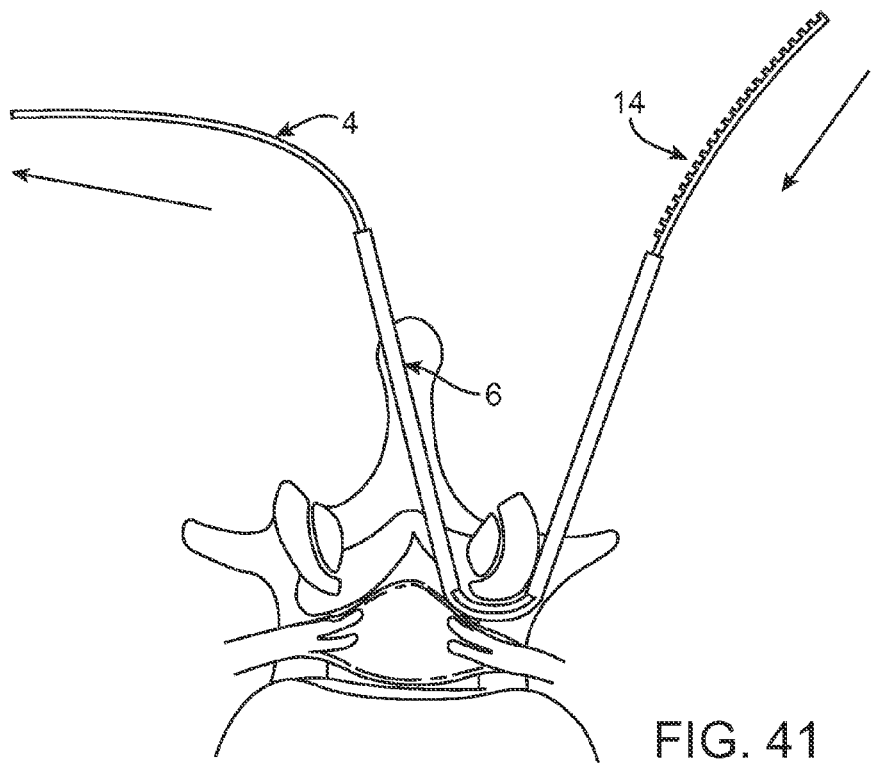
Figure 42:
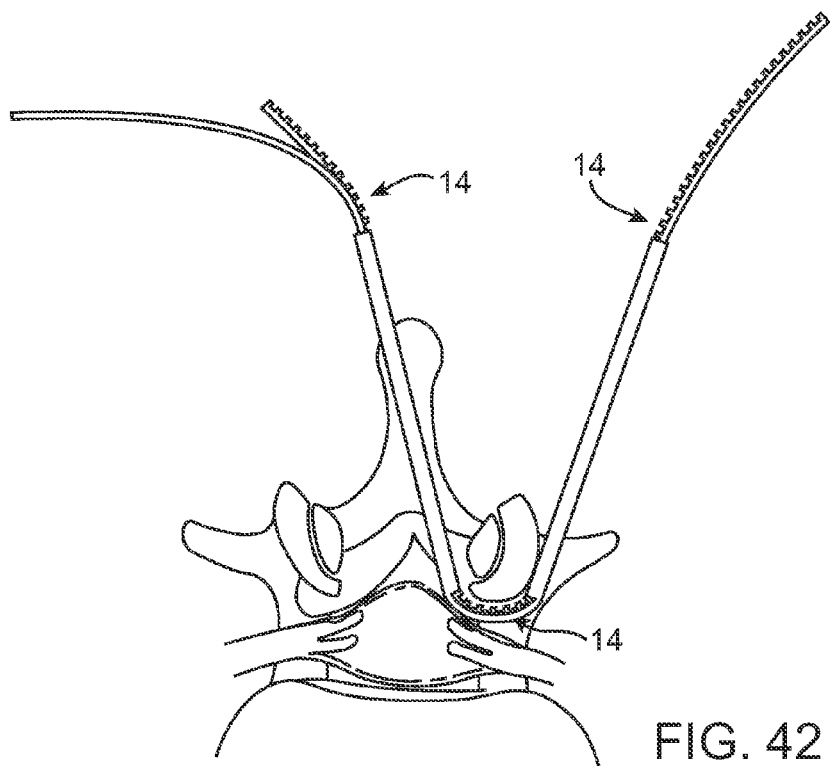

Referring now to FIGS. 26A and 26B, a tissue modification device 402 has a rigid proximal shaft portion 404 from which a flexible portion 406 extends axially. A plurality of tissue modification elements in the form of blades 408 extend from a first surface 410 of flexible portion 406, as described above. Flexible portion 406 is advanced into a patient body so that first surface 410 is bent over a target tissue, with the target tissue here comprising both ligament 412 and bone 414. First surface 410 of flexible portion 406 is wrapped over an at least partially convex surface 416, with the convexity of the surface defining an inward orientation 418 and an outward orientation 420 (see FIG. 40B). Hence, axial tension 422 on the flexible portion 406 causes the first surface 410 to move inwardly toward the target tissue 412, 414.

Referring still to FIGS. 26A and 26B, the surface 416 of the target tissue need not, and often will not, be substantially cylindrical, but will often instead have portions that are more inward 418, and other portions that are more outward 420. For example, a first portion or region of the surface 416 adjacent a first edge 424 of flexible portion 406 may be significantly more outward 420 than a region of the surface that is adjacent an opposed edge 426 and engagement between the flexible portion and tissue surface. As a result of the axial tension 422 in the flexible portion 406, this difference can cause the flexible portion to rotate about its central axis. Continued reciprocation of the flexible portion when its rotational orientation is not adequately controlled could cause an edge 426 of the flexible portion to cut laterally into target tissues as illustrated in FIG. 26B, or even inadvertent flipping of the flexible portion which might expose non-target tissue 430 to damage from the cutting blades along first surface 410, rather than effecting controlled volumetric removal of the target tissue.

To inhibit uncontrolled rotation of the flexible portion 406, the rigid shaft of proximal portion 404 significantly improves the control over both the orientation and position of the flexible portion, in part by transmitting torque 432 from the proximal handle to the treatment site within the patient. By rotating (or restraining) the proximal handle about the axis of the shaft, torque is transmitted down the shaft and to the flexible portion adjacent the target tissue. The torque can be transmitted so as to inhibit roiling or flipping of the flexible portion, and can also be used to intentionally alter an orientation of the flexible portion and tissue modifying members. The proximal handle and/or proximal portion may have an asymmetric shape or some asymmetric indicia that identifies the orientation of the tissue modifying members to enhance the physician's control over the orientation of tissue being modified and/or removed.

Figure 27A:
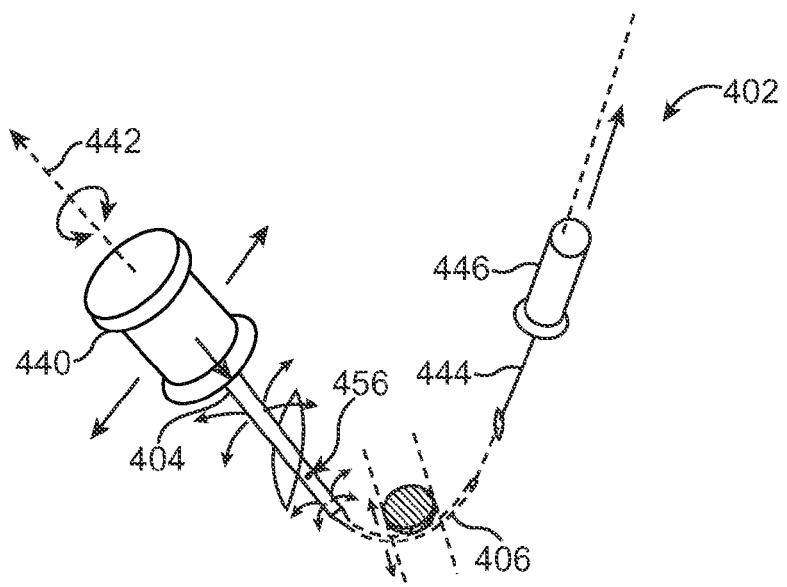
FIG. 27A is a perspective view schematically illustrating shifting of the flexible member laterally along a target tissue by laterally translating the proximal rigid portion, and/or by pivoting the rigid portion about tissues along the site of insertion.
Figure 27B:
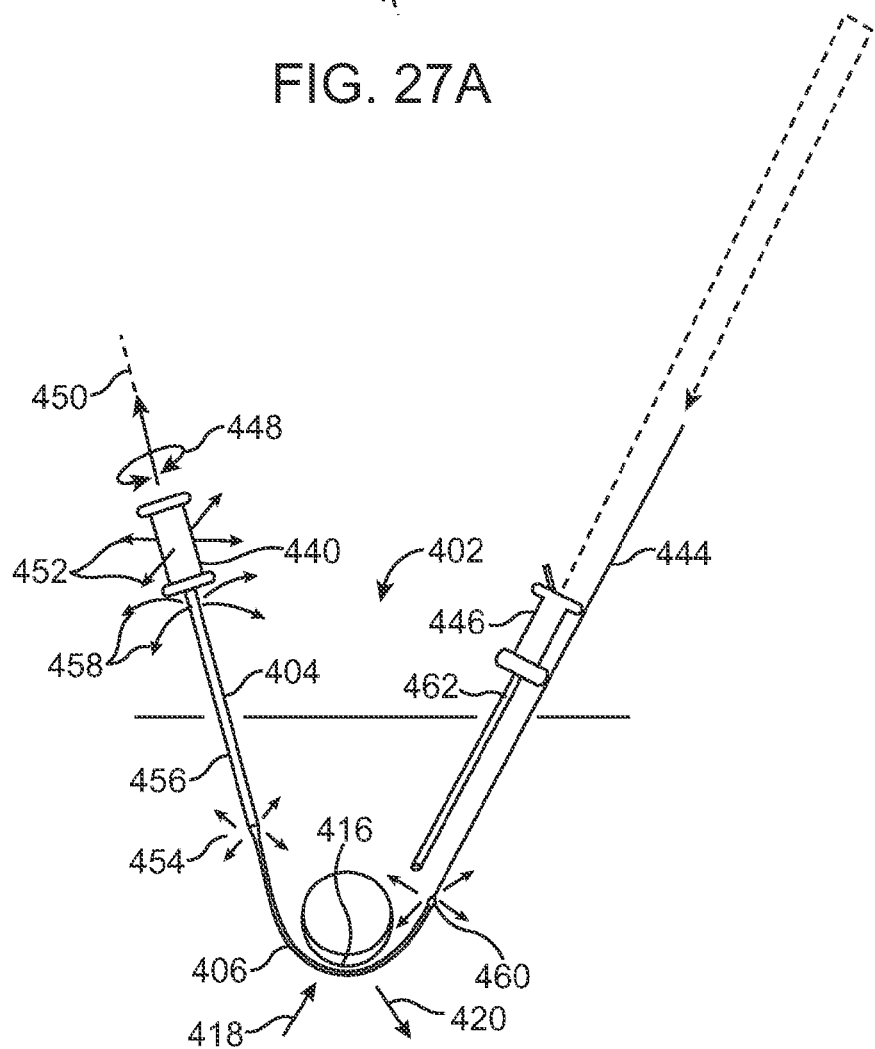
FIG. 27B schematically illustrates lateral translation and pivoting of the rigid portion to effect shifting of the flexible portion relative to the target tissue, and also schematically illustrates an optional rigid tubular shaft coupled to a distal handle to similarly allow shifting of the distal end of the flexible portion and provide enhanced control over target tissue remodeling and/or removal.

Referring now to FIGS. 27A and 27B, additional aspects of the structure and use of rigid shaft proximal portion 404 to control the location and orientation of distal flexible portion 406 can be understood. As generally described above, tissue modification tool 402 is generally positioned for use with rigid portion 404 extending a proximal handle 440 through an open or minimally invasive surgical axis site to flexible portion 406, with the flexible portion often extending distally from an axis 442 of the proximal portion. The distal flexible portion 406 also has a central axis which extends around a target tissue to a distal end that is coupled to a guidewire 444 extending out of the patient, with a distal handle 446 being axially affixable to the guidewire so that tension can be applied to the flexible portion 406 by pulling upward on the proximal and distal handles 440, 446.

As described above, torqueing the shaft of rigid portion 404 about ifs axis using handle 440 (as schematically illustrated by arrows 448) can help to orient the tissue treatment member(s) along the first surface 410 of flexible portion 406 toward a target region of the target tissue. Additionally, it will often be desirable to shift flexible portion 406 laterally relative to its central axis, that is, into and/or out of the illustration of FIG. 27B. Handle 440 can be used to help move flexible portion 406 using one or both of two techniques. First, handle 440 can be pushed laterally relative to the axis 450 of the rigid proximal shaft portion 404 as illustrated by arrows 452. Where handle 440 laterally translates the shaft without rotating of the shaft, end 454 of rigid portion 404 may also translate laterally, thereby laterally shifting the flexible portion 406. Alternatively, handle 440 may be used to pivot the rigid portion 404 about an effective pivot point 456 (as schematically illustrated by curving arrows 458), similarly effecting lateral movement of the end 454 of the rigid portion within the patient. Some combination of lateral movement of the overall rigid portion 404 will often be combined with some pivoting of the rigid portion. The pivot point 456 is not necessarily at a fixed location in space, and may move somewhat as the tissues adjacent the tissue modification tool 402 are displaced and/or compressed.

As described above, guidewire 444 advantageously allows tension to be applied to a distal end 460 of flexible portion 406, optionally allowing the flexible portion to be shifted and/or positioned along its curving access for treatment of a target tissue, as well as allowing distraction of target tissues, reciprocation of the tissue modification elements and flexible portion against a target tissue, and the like. To enhance lateral and rotational control over the flexible portion 406, and particularly the length of the flexible portion close to its distal end 460, a second rigid shaft 462 may be affixed to distal handle 446. The second shaft 462 may have a central lumen that receives guidewire 444 therethrough. Second shaft 462 may then be manipulated as described above regarding the rigid portion 404, allowing the distal end 460 of the flexible portion to be shifted in coordination with the shifting effected by the rigid portion 404. This may enhance overall control over the lateral movement of flexible portion, optionally using the pivoting and/or lateral movement techniques described above. The second rigid shaft 462 will often have a distal end with a profile suitable for advancing distally over guidewire 44 toward the target tissue, and may also torquably engage the distal end of flexible portion 406 so as to allow the distal end to be torqued about the longitudinal axis of the flexible portion and guidewire (such as by providing a slot in the inserted end of second shaft 462 to torquably receive the distal end of the flexible portion).

Referring now to FIGS. 28A-28E, it will often be desirable to remove target tissue from a tissue region 1259 which is wider than an adjacent tissue modification device 1260. Additionally, it may be desirable to reorient the tissue modification members carried by a flexible portion of a tissue modification device 1260 so as to treat portions of the target tissue that are at different angles. As described above, tensioning of tissue modification device 1260 using the proximal and distal handles can urge the tissue modifying members toward a first region of the target tissue, such as the region being engaged by blades 1262, 1262' in FIG. 28B. As this tissue is removed, the tension will tend to keep the tissue modification device 1260 at the removed tissue location. Optionally, the orientation of the tissue modification device 1260 may be rotated about a central axis of the flexible portion of the tissue modification device by rotation of rigid portion 404 (see FIGS. 26A, 27A), resulting in lateral rotation of the flexible portion and tissue modification elements carried thereby in a counterclockwise direction (see FIG. 28C) wherein a clockwise direction (see FIG. 28D). Additionally, lateral translation and/or pivoting of the rigid portion 404 about pivot point 456 may be used to laterally shift or translate the tissue treatment device 1260.

Lateral shifting of the flexible portion may be facilitated (for example) by including tissue modification devices or blades having sufficient length to extend through ligament target tissue such as the ligamentum flavum, and by including tips on at least some of the tissue modification devices or blades that are large enough to avoid penetrating into underlying bone. This may allow the flexible substrate to ride over the tough ligament, facilitating lateral movement of the outermost blades into target ligament tissues. Lateral shifting of the flexible portion may also be facilitated by a flexible substrate structure which is relatively stiff in one lateral orientation (specifically, along the major surfaces) and more flexible in another lateral orientation (transverse to the major surfaces, so as to allow the flexible member to bend over the target tissue with a major surface oriented toward the target tissue). Advantageously, such selective lateral flexibility and lateral stiffness can be readily provided by a thin, flat substrate having a cross-section that includes a much larger moment in one orientation (for example, bending in the plane of the major surfaces) than another (for example, bending in the plane of the smaller edges).

Still with reference now to FIGS. 28A-28E, a method according to one additional embodiment can be understood for removing tissue using a tissue modification device 1260.

Figure 28A:
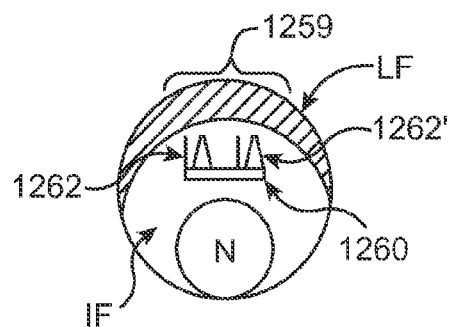
FIGS. 28A-28E are end-on views of a flexible portion of a tissue modification device with vertically oriented blades, demonstrating a method for shifting the device back and forth laterally in an intervertebral foramen, according to one embodiment of the present invention.

FIG. 28A is an end-on, diagrammatic representation of an intervertebral foramen IF, showing vertebral bone, ligamentum flavum LF and nerve root N, with device 1260 passing through the foramen IF between nerve root N and ligamentum flavum LF. Device 1260 may have some blades 1262 oriented at approximately a 0 degree angle relative to the longitudinal axis of device 1260, while other blades 1262' may be angled, relative to the longitudinal axis.

Figure 28B:
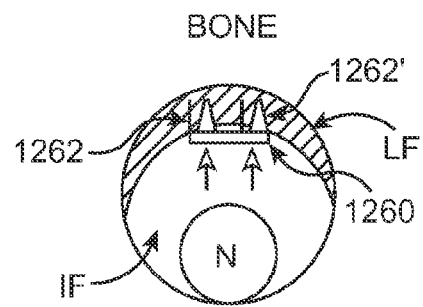

In FIG. 28B, device 1260 has been pulled upward (hollow-tipped arrows) to urge blades 1262, 1262' into ligamentum flavum LF so that at least one of blades 1262, 1262' contacts vertebral bone. In some embodiments, some or all of blades 1262, 1262' may have a height approximating a thickness of an average ligamentum flavum LF.

Figure 28C:
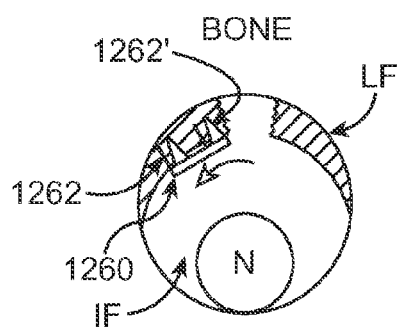

Referring to FIG. 28C, when device 1260 is reciprocated back and forth along its long axis, ligamentum flavum LF tissue is removed in one area of the intervertebral foramen IF. As device 1260 is reciprocated, angled blades 1262' may steer or guide device 1260 laterally in the intervertebral foramen IF (hollow-tipped arrow). In some embodiments, for example, device 1260 may steer to one side when the device is pulled in one direction and steer to the other side when the device is pulled in the opposite direction.

Figure 28D:
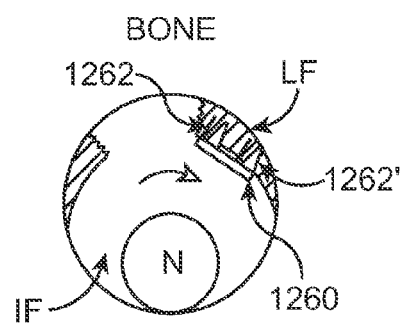

In FIG. 28D, device 1260 has moved toward the opposite lateral side of the intervertebral foramen IF (hollow-tipped arrow) to remove additional ligamentum flavum LF tissue. In some embodiments, any or all blades 1262, 1262' of device 1260 may have flat tops, which may help blades 1262, 1262' to slide or "skate" across the surface of bone as device 1260 is reciprocated to cut through soft tissue. This sliding or skating motion may also help device 1260 move from side to side within the intervertebral foramen IF.

Figure 28E:
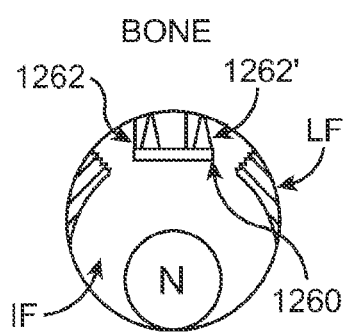
Figure 29:
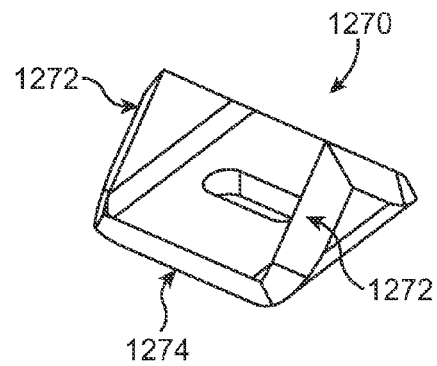
FIG. 29 is a perspective view of a double-blade member of the tissue modification device portion of FIG. 31 for attachment to a flexible portion of a tissue modification device, according to one embodiment of the present invention.

In FIG. 28E, much of the ligamentum flavum LF has been removed, and blades 1262, 1262' are in a position to treat bone. In some cases, a physician may choose to continue using device 1260 to remove bone, while in other cases a physician may wish to remove mostly or exclusively ligamentum flavum LF tissue. In various embodiments, the physician may determine when a desired amount of soft tissue and/or bone is removed by using tactile feedback from device 1260, by removing device 1260 to examine tissue trapped in device 1260, by radiographic visualization such as fluoroscopy, by use of one or more sizing probes or other instruments to gauge the size of the intervertebral foramen IF, or any combination of such methods.

When a desired amount of tissue has been removed, device 1260 may be removed from the patient to complete the procedure. As mentioned, in some embodiments, device 1260 may be used to remove only ligamentum flavum LF tissue and then removed from the patient to end the procedure. In alternative embodiments, device 1260 (or a differently configured device) may be used to remove both soft tissue and bone. In yet another alternative embodiment, a first device (for example, device 1260) may be used to remove ligamentum flavum LF tissue, the first device may be removed from the patient, and a second device may be inserted and used to remove bone. Thus, in some embodiments, two different devices may be used in one procedure, with one device optimized for soft tissue removal and another device optimized for bone removal.

With reference now to FIGS. 29-32, various embodiments of blade structures are shown. For example, in an embodiment as in FIG. 29, a blade structure 1270 may include two blades 1272 extending substantially vertically from abuse 1274. Base 1274 may provide a surface for attaching blades 1272 to one side of a tissue modification device. Blades 1272 may have beveled cutting edges and pointed tips, as shown.

Figure 30:
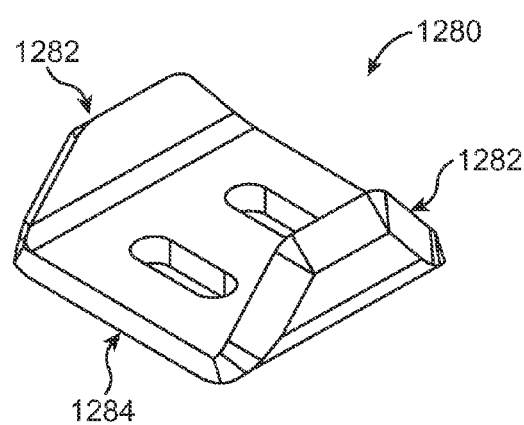
FIG. 30 is a perspective view of a double-blade member of the tissue modification device portion of FIG. 32 for attachment to a flexible portion of a tissue modification device, according to an alternative embodiment of the present invention.

In an alternative embodiment, as in FIG. 30, a blade structure 1280 may again include two blades 1282 extending vertically from a base 1284. In this embodiment, blades 1282 have beveled edges and a flat, beveled top.

Figure 31:
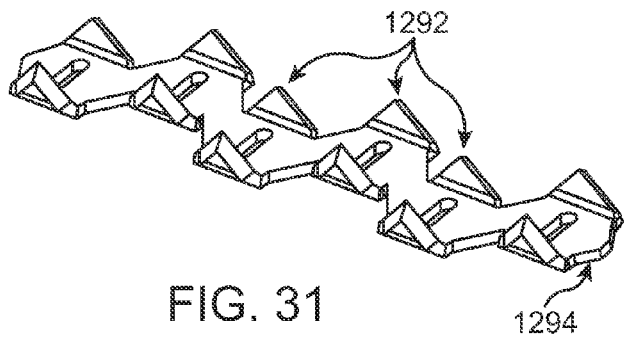

In another alternative embodiment, as in FIG. 31, a blade structure 1290 may include any number of blades 1292 coupled with a base 1294. In this embodiment, twelve blades 1292 are coupled with base 1294, and base 1294 has aback-and-forth or zig-zag configuration.

Figure 32:
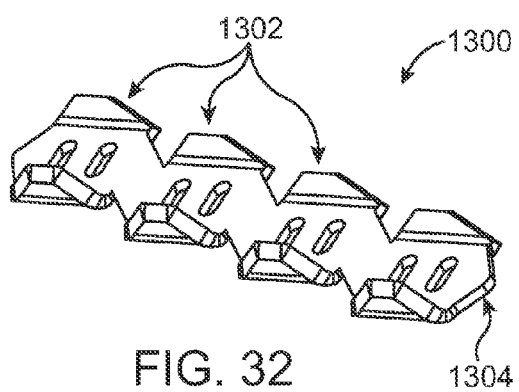

In another alternative embodiment, as in FIG. 32, a blade structure 1300 may include eight, flat-top blades 1302 (or any other suitable number) coupled with a base 1304 having a diagonal configuration. When base 1304 is attached to a surface of a tissue modification device, blades 1302 will typically be angled due to the diagonal configuration of base 1304.

In various alternative embodiments, any of the tissue modification devices and method described above may be used in combination with one or more vertebral distraction devices. In one embodiment, for example, an interspinous implant such as the X STOP® implant (offered by St. Francis Medical Technologies, Inc., Alameda, Calif., www.sfmt.com) may be inserted between adjacent vertebrae, and then access devices and/or tissue removal devices described herein may be used to remove or otherwise modify spinal tissue. Such an implant may be inserted and left place after a procedure, white in alternative embodiments a distraction device may be used only during a tissue removal procedure. Various embodiments and aspects of such distraction/tissue removal combinations are described in greater detail in U.S. Provisional Patent Application Ser. No. 60/884,371, titled "Spinal Stenosis Treatment Methods and Apparatus," filed Jan. 10, 2007, the full disclosure of which is hereby incorporated by reference.

The method of modifying the spinal anatomy can include confirming proper placement of the surgical apparatus. Confirming proper placement can include confirming proper placement with a nerve stimulator. Confirming proper placement with a nerve stimulator further comprises confirming proper placement with stimulation leads placed on a tissue remodeling side of the surgical apparatus. The method of modifying the spinal anatomy can include confirming proper placement of the surgical apparatus or barrier with a nerve stimulator having stimulation leads placed on a tissue remodeling side of the barrier or on a back side of the barrier.

The apparatus can be configured for use with a visualization element. The visualization element can be chosen from the group consisting of an epidural endoscope, a fluoroscope, ultrasound, XRay, MRI and combinations thereof. The apparatus can have a nerve stimulator to facilitate proper placement of the barrier. A conductive element can be included on a tissue modification side of the barrier or on a backside of the barrier to facilitate nerve localization. A working surface of the tissue remodeling device can have neurostimulation capabilities, thereby allowing for a positive and negative control in localizing neural tissue prior to tissue removal.

The method can include confirming proper placement of the tissue abrasion device. Confirming proper placement of the device can include confirming proper placement with a nerve stimulator. Confirming proper placement with a nerve stimulator can include confirming proper placement with a nerve stimulator having stimulation leads placed at a location chosen from the group consisting of a non-abrasive side of the tissue abrasion device, a back side of a protective sleeve or cover placed over the tissue abrasion device, an abrasive side of the tissue abrasion device, a working side of the tissue abrasion device, and combinations thereof. Confirming proper placement can include confirming placement via a modality chosen from the group consisting of fluoroscopic, MRI, CT, infrared, ultrasound imaging, surgical triangulation, and combinations thereof.

The apparatus can have a protective cover disposed about the tissue abrasion device, where the protective cover is configured to limit exposure of an abrasive surface of the device to areas where tissue removal is desired. The apparatus can have a nerve stimulator in communication with the tissue abrasion device to facilitate proper placement of the device.

Figure 33A:
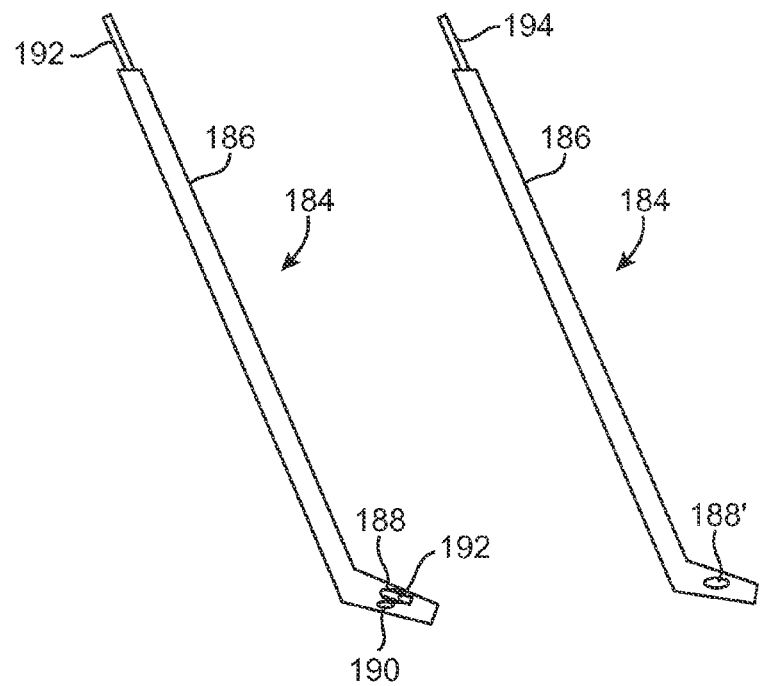
FIG. 33A is a schematic view of apparatus of the present invention for obtaining open surgical access.

As discussed previously, variations of the present invention preferably provide for access, neural protection and/or decompression for treatment of spinal stenosis. With reference to FIGS. 33 and 34, methods and apparatus for obtaining access to the neural foramen utilizing open surgical variations of the present invention are described. FIG. 33A illustrates two variations of access element 184. In the first variation (33A-1), access element 184 comprises cannulated probe 186, illustratively an elevator probe having first and second lumens 188 and 190. Visualization element 192, such as an epidural endoscope, may be advanced through or coupled to lumen 188 to provide visualization at the distal tip of probe 186.

The method can include, prior to selective removal of the impinging tissue, confirming proper placement of the neural protection element and the tissue removal device. Confirming proper placement can include localizing the nerve root with a stimulation waveform.

The neural protection element can be an element configured for delivery via the access element. The neural protection element can be configured for transforaminal placement between impinging tissue and a nerve root. The access element can be configured for transforaminal placement. The neural protection element can have a sheath having a window. The tissue removal device can be configured for placement within the sheath such that tissue removal elements disposed on a tissue removal surface of the device are locally exposed within the window. The window can be configured for transforaminal placement.

In the second variation (FIG. 33A-2), probe 186 of access element 184 comprises single lumen 188'. Visualization element 192, as well as cannula 194 or curved guide wire 4 described hereinafter, may be advanced through the unitary lumen—either in parallel or in sequence. Alternatively, the visualization element may be omitted or may be attached directly to the probe. As will be apparent, access element 184 may comprise any desired number of lumens.

Figure 33B:
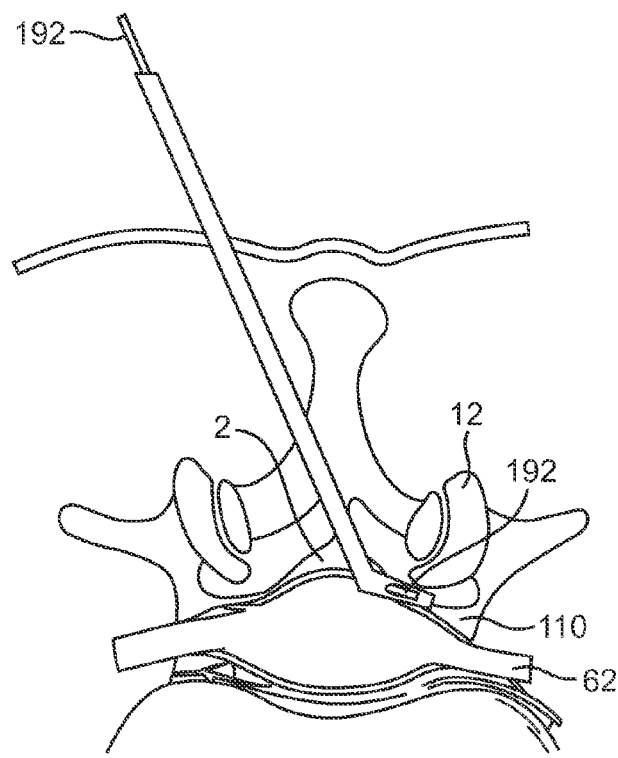
FIGS. 33B-33E are cross-sectional views through a patient's spine, illustrating open surgical methods of using the apparatus of FIG. 33A to obtain access.

In FIG. 33B, the dual lumen variation of access element 184 has been placed through a surgical incision or cut-down in proximity to neural foramen 110 while under optional visualization from element 192. Visualization may facilitate access via a minimally invasive or keyhole surgical cut-down, as opposed to a fully open approach. Direct visualization alternatively or additionally may be utilized.

Figure 33C:
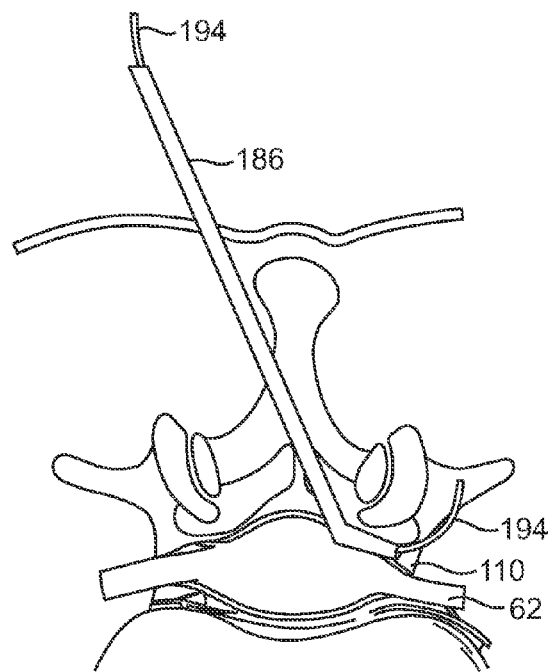
Figure 33D:
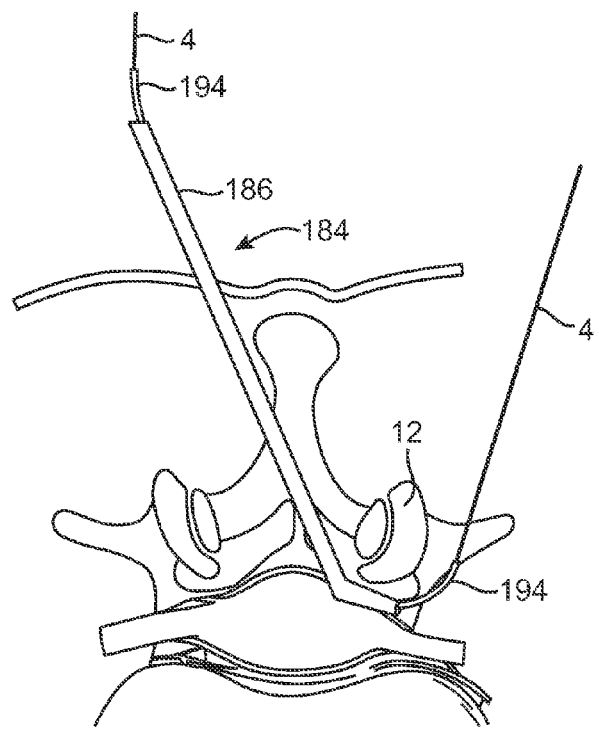
Figure 33E:
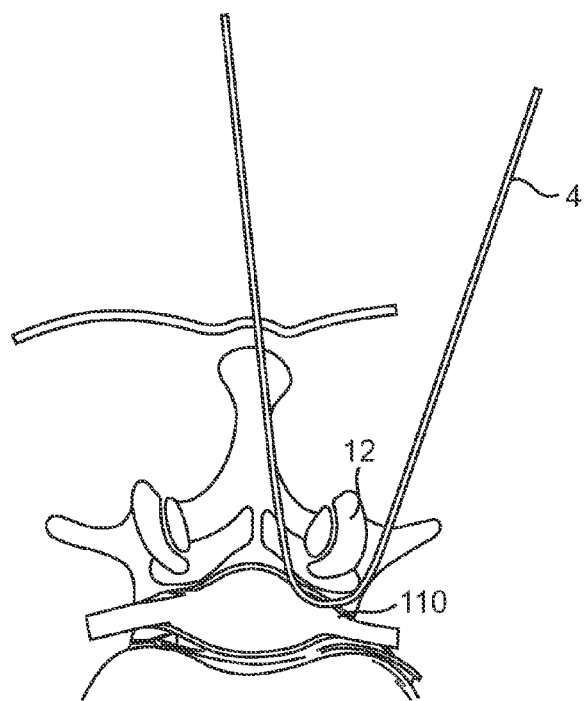

As seen in FIG. 33C, with probe 186 properly positioned, atraumatic curved tube, introducer or cannula 194 may be advanced through lumen 188' of the probe and driven laterally to cannulate the neural foramen 110. Cannula 194 optionally may be configured to deliver a stimulation waveform at or near its distal tip for monitoring proximity to the nerve root during cannulation of the foramina with the cannula. A preferably straight, flexible guide wire 4 or needle, which optionally comprises sharpened tip, then may be advanced through cannula 194 and driven posteriorly through the skin of the patient's back, as in FIG. 33D. Alternatively, a second surgical incision and or cut-down may be formed at or near the exit of the neural foramen for grasping the guide wire and pulling it through. With access guide wire 4 positioned through and across the neural foramen, probe 186 may be removed, as in FIG. 33E. This leaves the guide Wire 4 in place to provide access for, e.g., neural protection and tissue removal apparatus, as described hereinbelow.

Figure 34A:
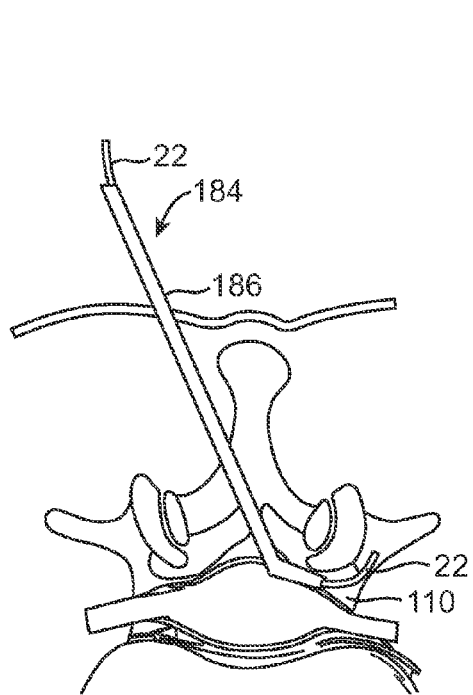
FIGS. 34A and 34B are cross-sectional views through a patient's spine, illustrating a variation of the methods and apparatus of FIG. 33.
Figure 34B:
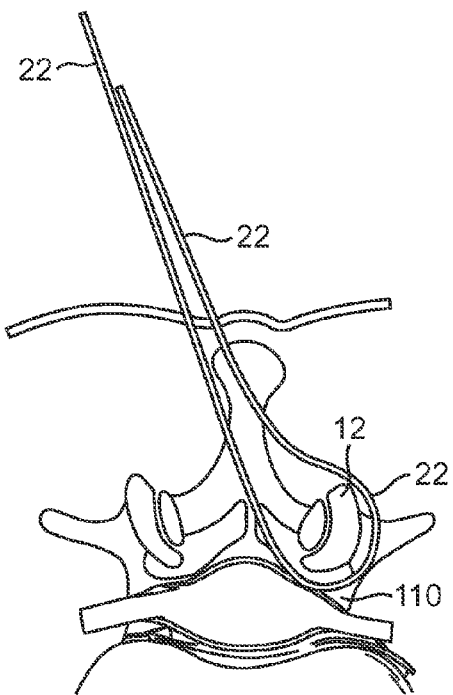

With reference to FIG. 34, an alternative method for obtaining open access is described. As seen in FIG. 34A, curved guide wire 22 may be advanced through lumen 188' of probe 186, such that the guide wire 22 passes through the neural foramen 110, encircles the facet 12 and reemerges in the surgical field. Guide wire 22 optionally may be configured to deliver a stimulation waveform at or near its distal tip for monitoring proximity to the nerve root during passage of the wire through the foramen 110. The needle may, for example, be insulated at regions other than the distal tip. With the wire encircling the facet 12, probe 186 then may be removed, as seen in FIG. 34B, leaving access guide wire 22 in place to provide access for selective removal of impinging tissue.

Access also may be achieved in a percutaneous fashion. For example, access may be achieved via an access element comprising an epidural needle or probe, or via an epidural endoscope having a working channel, that is positioned within the epidural space. In one variation, a curved atraumatic needle or cannula may be advanced through the percutaneous access element and driven laterally to cannulate the neural foramen. A preferably straight, flexible guide wire or needle then may be advanced through the curved needle and driven posteriorly through the skin of the patient's back. In an alternative variation, a curved guide wire may be advanced through the percutaneous access element and passed transforaminally. Percutaneous access optionally may be aided by the use of image guidance, an epidural endoscope or any other visualization technique.

Figure 35:
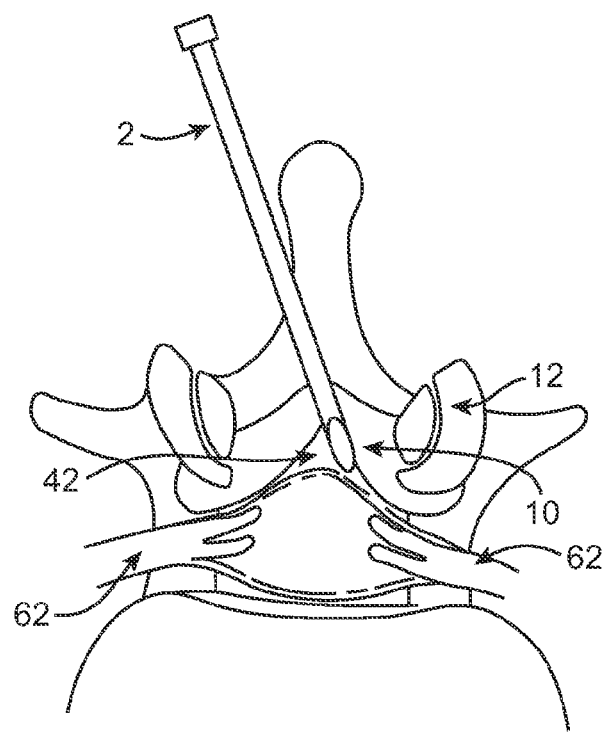
FIGS. 35-42 are cross-sectional views through a patient's spine, illustrating a method and apparatus for selective surgical removal of tissue.

FIG. 35 shows a percutaneous method and apparatus for obtaining access for selective surgical removal of tissue. Access element is disposed within epidural space 42. Access element may comprise, for example, epidural needle 2, an epidural trocar, an epidural endoscope, etc. The needle tip is anterior to the ligamentum flavum 10, but still posterior to the dura 46 in the posterior epidural space 42.

Figure 36:
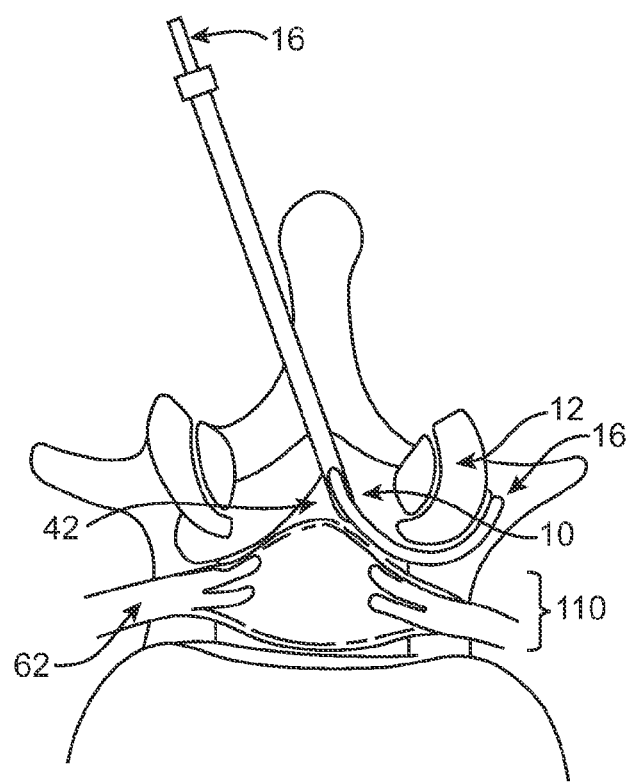

FIG. 36 illustrates a preferred method of cannulating the neural foramina, where an atraumatic curved tube or cannula 16 (e.g., blunt, curved needle composed of memory material) is passed through the straight epidural needle 2 (alternatively, a stiff epidural catheter, or steerable guidewire may be inserted through the needle for this step) to cannulate the neural foramen NF. The curved needle 16 is flexible enough to be passed through the straight epidural needle 2, but is made of a memory material that returns it to its curved configuration upon when it is passed into tissue. The second needle 16 (alternatively, a steerable, stiff catheter or guidewire), is advanced through the epidural space 42, possibly passing through a portion of the ligamentum flavum 10, towards and then through the ipsilateral or contralateral neural foramen 110. The surgeon may use any combination of tactile feel, image guidance, direct visualization, and/or fiberoptic visualization to ensure that the curved element 16 is driven through the neural foramen, anterior to the facet (zygapophysial) joint complex 12, but posterior to the nerve root 62 or ganglion. As discussed previously, the cannulas may be configured to stimulate and monitor response of the nerve root as a safety precaution during cannulation of the foramen.

Figure 37:
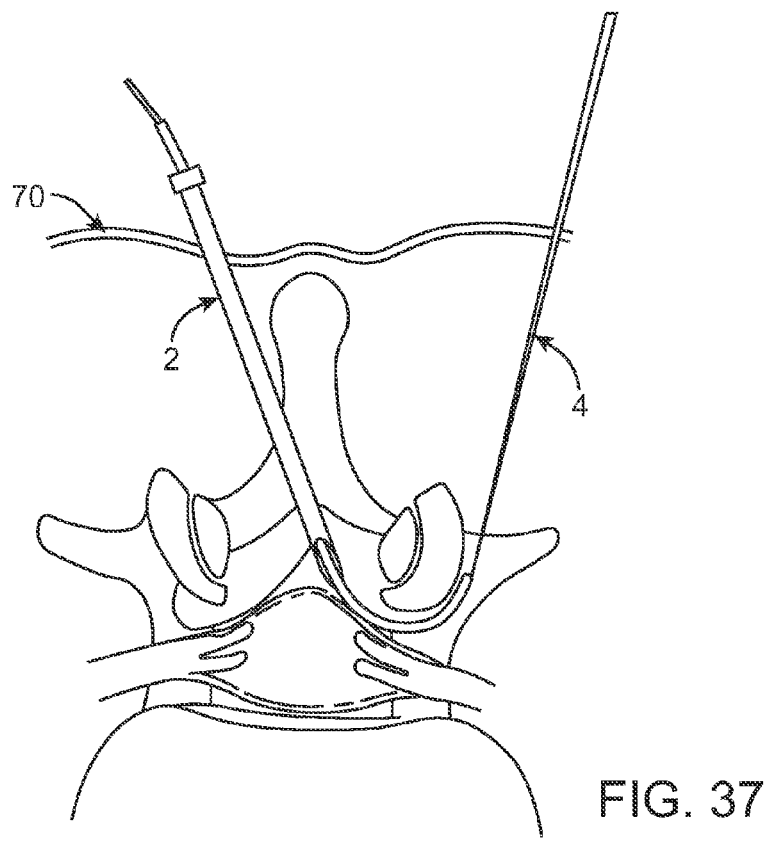
Figure 38:
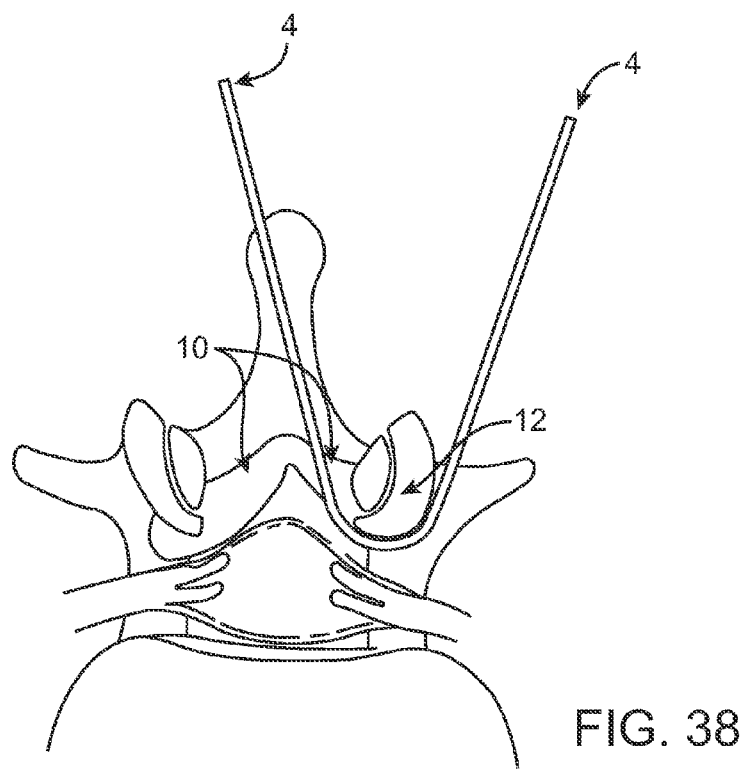
Figure 39:
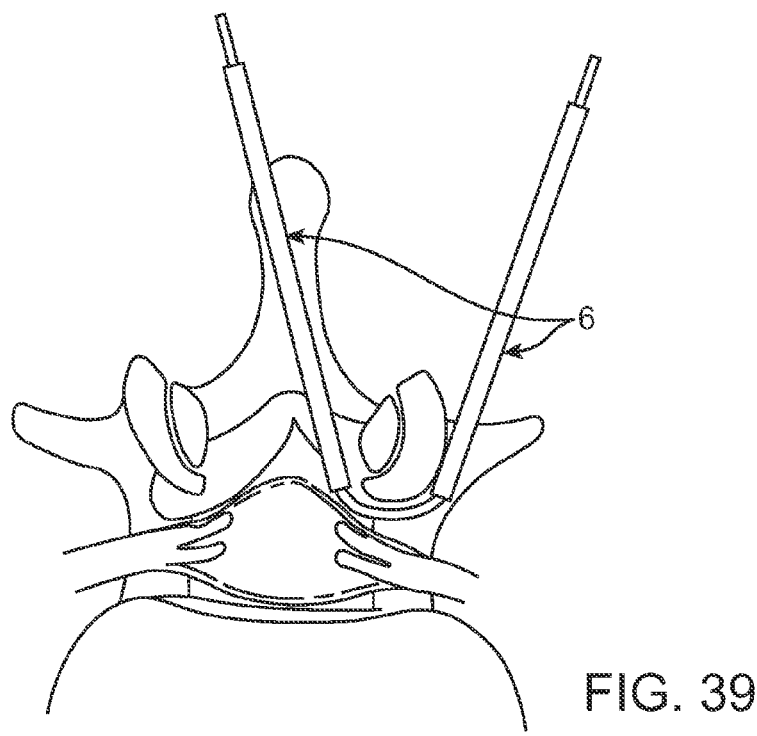

Once the curved element is in position through the neural foramen, the surgeon subsequently passes a smaller gauge straight and sharp flexible guidewire 4 (or needle), as in FIG. 37 through the lumen of the larger curved needle that is in position through the neural foramen 110, until it exits into the tissue lateral to the neural foramen (FIG. 37). This straight wire 4 or straight needle exits the curved element with its tip facing in a posterior or posterior-lateral direction. It is advanced further in this direction, passing to, and then through the skin of the patient's back 70, as in FIG. 37. Access element 2 and cannula 16 then may be removed, as in FIG. 38, leaving access guide wire 4 in place transforaminally to provide access to the lateral recess and neural foramen.

As an alternative to deploying cannula 16 through access element 2, the cannula 16 may be delivered over the access element. As yet another alternative, upon placement of the access element in the epidural space, a stiff rod may be advanced through the lumen of the access element, and the access element may be removed. Cannula 16 then may be deployed over the stiff rod, which then may be removed from the lumen of the cannula and replaced with guide wire 4.

In some alternative embodiments, a steerable needle or wire 18 is placed through the neural foramina 110 from the lateral towards the medial side of the foramen 110. This lateral to medial neuroforaminal approach may begin with a curved, blunt wire through a straight needle (as described in the previous technique), or using a curved needle technique, a steerable guidewire technique, a needle-through-a-needle technique, or common variations thereof. While a loss of resistance technique is not as helpful with this transforaminal approach to the epidural space 42, as it was in the previously described posterior approach to the epidural space 42, the method is, in many other aspects, otherwise similar to the method illustrated in FIGS. 35-42.

Figure 43:
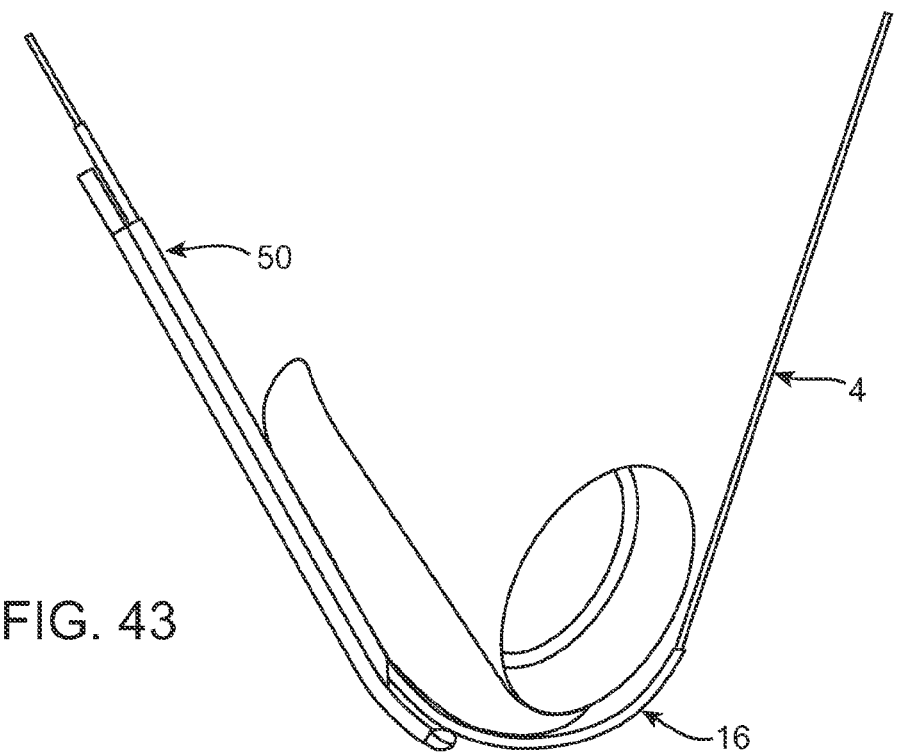
FIGS. 43-48 are partial cross-sectional views through a patient's spine, illustrating a double barrel system used with additional methods and apparatus for placement of an abrasion apparatus through the neural foramina for selective surgical removal of tissue.
Figure 44:
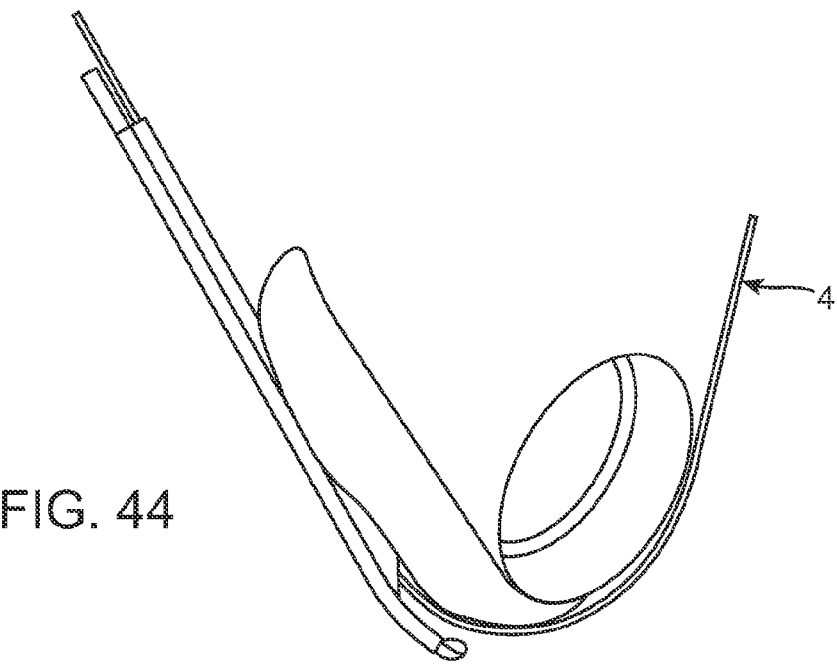
Figure 45:
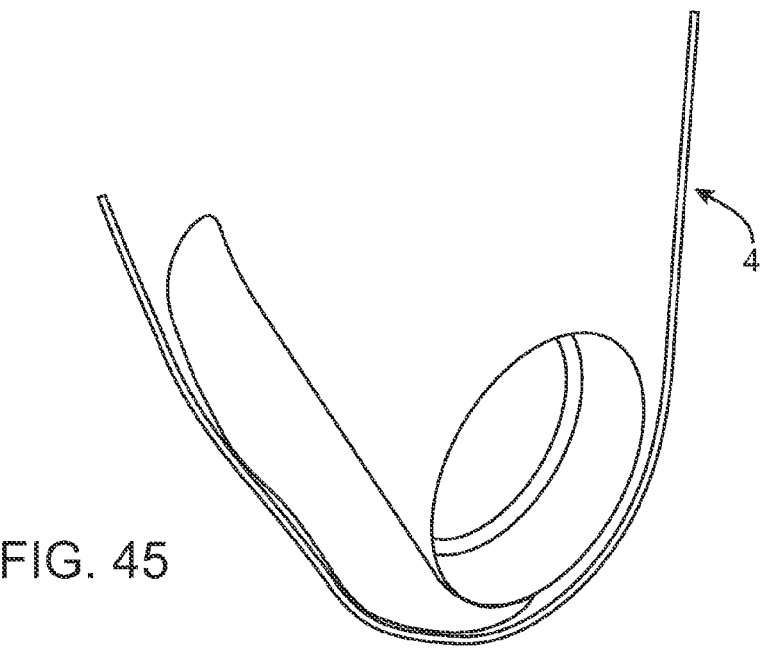
Figure 46:
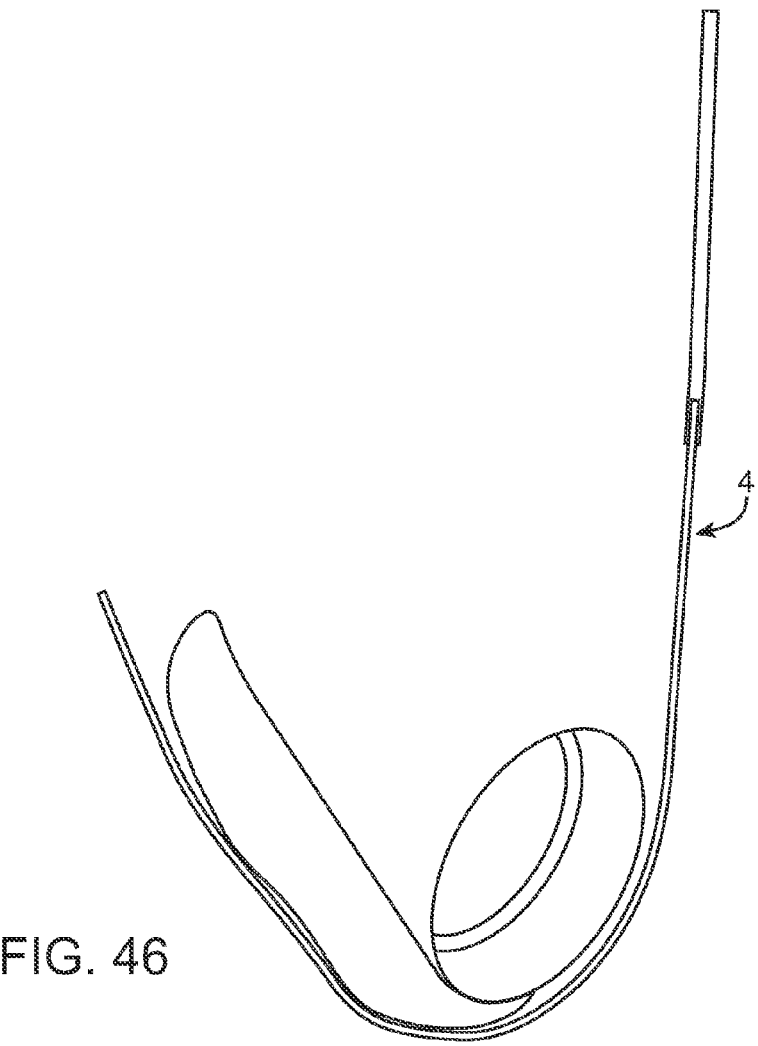
Figure 47:
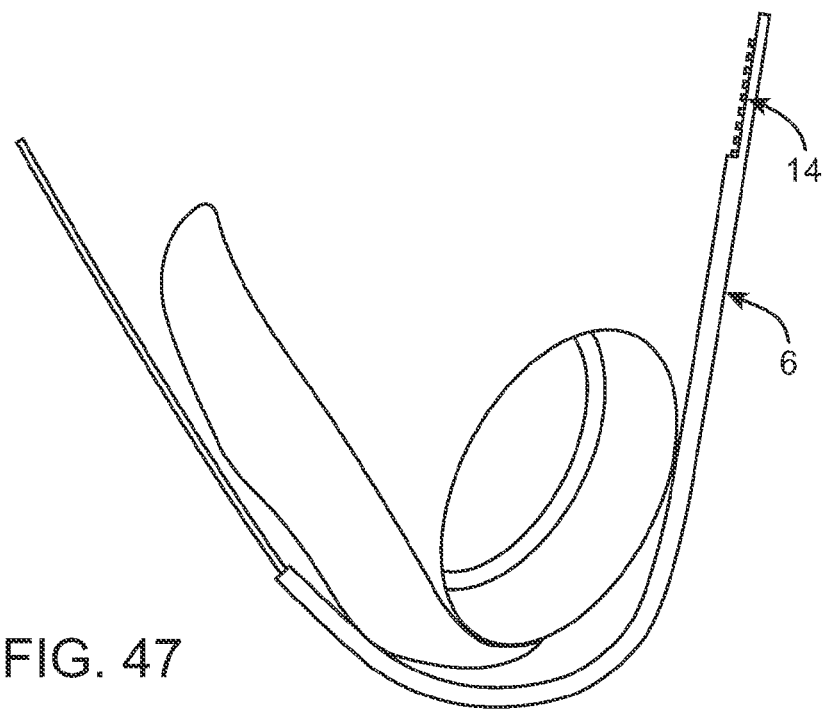
Figure 48:
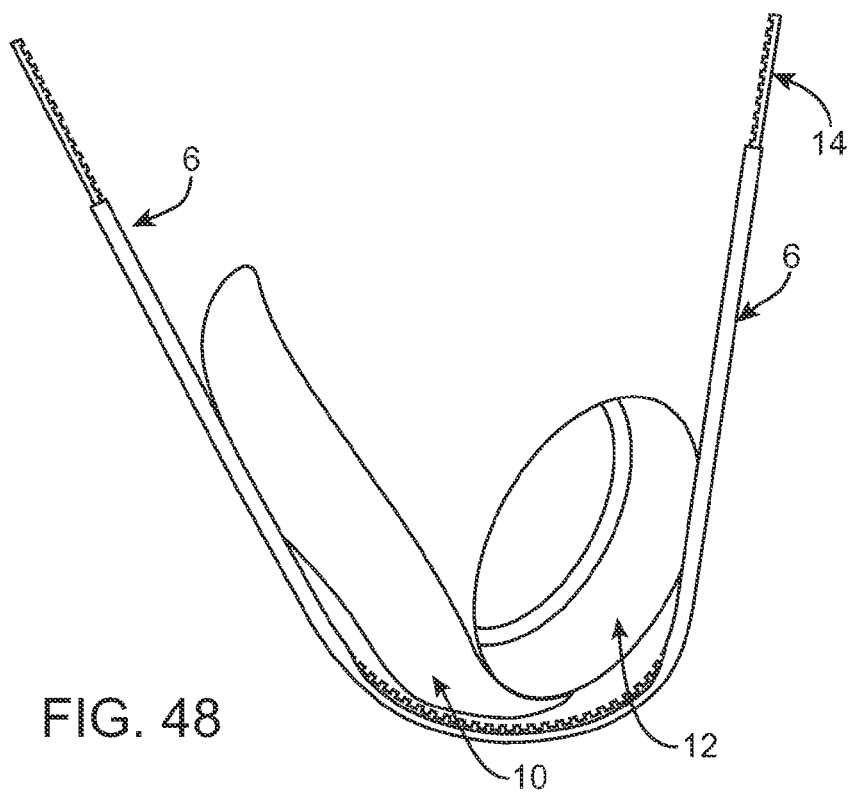

In FIG. 43, straight wire or needle 4 is driven through curved needle 16 disposed in working channel 50 of double barrel epidural needle. This straight wire or needle 4 is advanced until it has penetrated through the skin and out of the patient's body. The straight wire preferably has a sharp tip. In FIG. 44, curved needle 16 is withdrawn from working channel 50, leaving straight wire or needle 4 in place. Then, as seen in FIG. 45, the epidural needle and working channel may be withdrawn from the patient, or, in an alternative embodiment, when using a detachable working channel 50, the working channel alone may be withdrawn from the patient, leaving straight wire 4 in place. In FIG. 46, straight wire 4 is hooked to abrasion device 14 and/or the abrasion device's protective sleeve 6. In FIG. 47, the abrasion device 14 and/or the device's protective sleeve are pulled into position by wire 4 as the wire is removed. In FIG. 48, wire 4 has been completely removed, and the abrasion device 14 and its protective sleeve 6 are property positioned for tissue resection, anterior to the facet 12 and ligamentum flavum 10.

In an open surgical variation, the abrasive element 14 and its cover 6 may be placed through the surgical incision, from an interlaminar, translaminar, or neuroforaminal approach. Visualization and placement may be aided via partial or complete laminectomy, facetectomy, or ligamentectomy. Methods for threading the neural foramina include, but are not limited to the use of a wire, blunt needle, probe, endoscope, or suture. After spinal neuroforaminal placement, the abrasion device 14 is used to selectively remove tissues that impinge on the neurovascular structures within the lateral recess 108 and neural foramen 110, on the anterior side of the facet joint 12. In an open approach, as with a percutaneous approach, the device may be inserted through a needle, optionally under image guidance or with the aid of an epidural endoscope. Once placed through the neural foramina 110 of the spine, around the anterior border of the facet joint 12, and anterior to the ligamentum flavum 10, the medical practitioner may enlarge the lateral recess and neural foramina via frictional abrasion, i.e., by sliding the abrasive surface across the tissue to be resected (e.g., far lateral ligamentum flavum, anterior and medial facet, osteophytes). The abrasion device alternatively or additionally may be placed through the neural foramen 110 anterior to the facet joint 12, but through or posterior to the ligamentum flavum 10. The medical practitioner controls the force and speed of the abrasive surface against the tissue to be removed, while optional protective covers, tubes or sleeves 6 help limit the area exposed to the abrasive element for treatment.

In FIG. 43, straight wire or needle 4 is driven through curved needle 16 disposed in working channel 50 of double barrel epidural needle. This straight wire or needle 4 is advanced until it has penetrated through the skin and out of the patient's body. The straight wire preferably has a sharp tip. In FIG. 44, curved needle 16 is withdrawn from working channel 50, leaving straight wire or needle 4 in place. Then, as seen in FIG. 45, the epidural needle and working channel may be withdrawn from the patient, or, in an alternative embodiment, when using a detachable working channel 50, the working channel alone may be withdrawn from the patient, leaving straight wire 4 in place. In FIG. 46, straight wire 4 is hooked to abrasion device 14 and/or the abrasion device's protective sleeve 6. In FIG. 47, the abrasion device 14 and/or the device's protective sleeve are pulled into position by wire 4 as the wire is removed. In FIG. 48, wire 4 has been completely removed, and the abrasion device 14 and its protective sleeve 6 are property positioned for tissue resection, anterior to the facet 12 and ligamentum flavum 10.

In an open surgical variation, the abrasive element 14 and its cover 6 may be placed through the surgical incision, from a interlaminar, translaminar, or neuroforaminal approach. Visualization and placement may be aided via partial or complete laminectomy, facetectomy, or ligamentectomy. Methods for threading the neural foramina include, but are not limited to the use of a wire, blunt needle, probe, endoscope, or suture. After spinal neuroforaminal placement, the abrasion device 14 is used to selectively remove tissues that impinge on the neurovascular structures within the lateral recess 108 and neural foramen 110, on the anterior side of the facet joint 12. In an open approach, as with a percutaneous approach, the device may be inserted through a needle, optionally under image guidance or with the aid of an epidural endoscope. Once placed through the neural foramina 110 of the spine, around the anterior border of the facet joint 12, and anterior to the ligamentum flavum 10, the medical practitioner may enlarge the lateral recess and neural foramina via frictional abrasion, i.e., by sliding the abrasive surface across the tissue to be resected (e.g., far lateral ligamentum flavum, anterior and medial facet, osteophytes). The abrasion device alternatively or additionally may be placed through the neural foramen 110 anterior to the facet joint 12, but through or posterior to the ligamentum flavum 10. The medical practitioner controls the force and speed of the abrasive surface against the tissue to be removed, while optional protective covers, tubes or sleeves 6 help limit the area exposed to the abrasive element for treatment.

Referring now to FIGS. 45-48, an additional method and apparatus for placement of a tissue abrasion apparatus for selective surgical removal or remodeling of tissue is described. The double lumen epidural needle apparatus 84 is positioned for advancement into the epidural space 42. The covered and blunt tip of the epidural needle 2, double lumen epidural needle 84, or the blunt end of the epidural endoscope 38, may be advanced into the ipsilateral or contralateral lateral recess 108, towards the neural foramen 110, in a direction parallel to both the adjacent ligamentum flavum 10 and the dura 46. A fiberoptic element 38 has been placed within epidural needle 2, providing both a means for fiberoptic visualization of the epidural space 42 and a means to blunt the needle and thereby protect the tip of the needle from damaging the dura 46 or neural or vascular structures. The endoscope has been advanced along ligamentum flavum 10 (visually a "yellow ligament") to the lateral recess 108. "Safe zone" 44 designates the area in which a medical practitioner may resect, ablate, or otherwise modify tissue safely, directly visualizing the area of tissue modification through the fiberoptic element. The second lumen 50 of the two lumen needle 84 or endoscope may be used as a working channel, or to dispense the abrasive element 14 and/or its protective sleeve 6 (FIGS. 43-48), or the working barrier 134 described in the primary patent referenced herein. After the neural foramen 110 has been cannulated with a non-sharp curved needle 22 or catheter (FIG. 43), and after the flexible, sharp, straight needle or wire 2 has been passed through the curved needle 22 until its tip is advanced through the skin in the patient's back (FIG. 43), the abrasion apparatus 14 and/or its sleeve or cover 36 are pulled through the neural foramen 110, as illustrated in FIGS. 45-48. The curved needle 22 or tube may, for example, be fabricated from spring steel, Nitinol, or other memory material that will allow it to be inserted through a straight needle, but to return to a fixed curve upon exiting the straight epidural needle 2 or working channel 50. The curved needle 16 optionally may be steerable. Preferably, the curved needle tip is not sharp, but is rounded or designed in other fashions less likely to cut tissue, in order to reduce a risk of neural or vascular damage.

Figure 49:
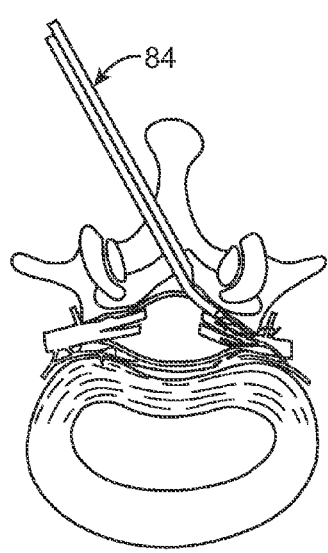
FIGS. 49-61 are cross-sectional views through a patient's spine, illustrating a variation of the methods and apparatus of FIGS. 43-48.

The present invention also describes methods and apparatus that may be used as a compression dressing, after tissue resection or ablation. One variation of the compression dressing is placed in a position where it is firmly wrapped around the facet and ligamentum flavum through the neural foramina, as illustrated in FIG. 49. By tightly pressing against treated tissue surfaces, such a device serves to promote desired tissue remodeling; to prevent edema from leading to impingement on neural or vascular tissue during early healing, to contain debris; to promote postoperative hemostasis; to block scar formation between the raw tissue surfaces and the adjacent neural and vascular structures; to avoid inflammation or irritation to neural and vascular structures from contact with adjacent resected tissue surfaces; and as a mechanism for sustained drug delivery post-operatively (e.g. steroids, procoagulants, adhesion barriers).

Figure 50:
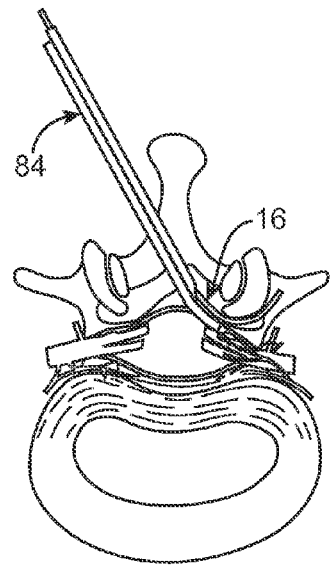
Figure 51:
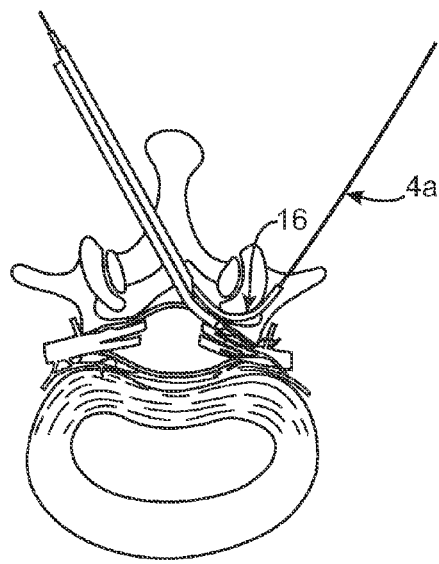
Figure 52:
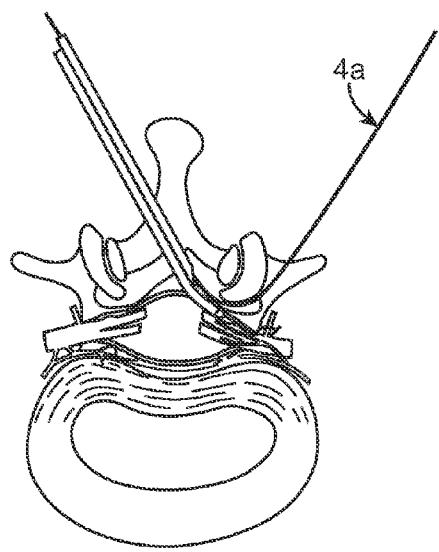
Figure 53:
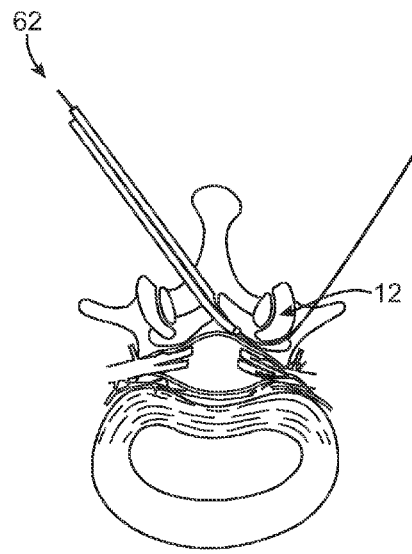
Figure 54:
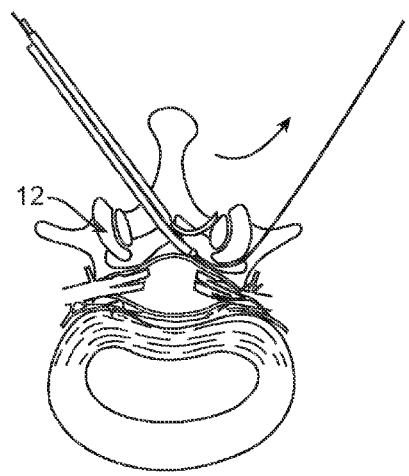
Figure 55:
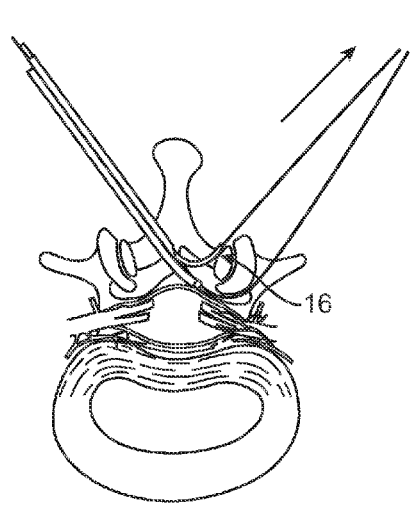
Figure 56:
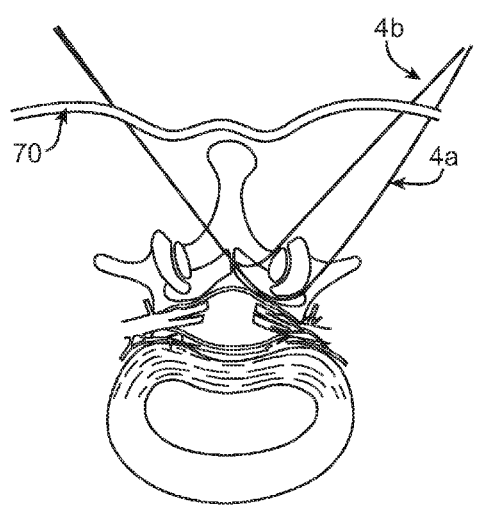

Referring now to FIGS. 49-63, a variation of the method and apparatus of FIGS. 43-48 is described, comprising another preferred approach for placement of the abrasion device. This series begins with FIG. 49, in which a double lumen, blunt tipped, epidural device 84, has already been advanced to the lateral recess 108. Next, FIG. 50 shows a curved flexible needle 16, preferably with an atraumatic tip, that has been advanced, via the working channel 50, through the neural foramina 110. FIG. 51 illustrates threading of the straight, flexible, sharp tipped wire 4a through the curved needle 22, and advanced posteriorly until it exits the skin of the back. In FIG. 52, the curved needle has been withdrawn, leaving the straight wire 4a in place. In FIG. 53, the double lumen epidural apparatus 84 is slightly withdrawn, from the patient, so that the working channel 50 is directed towards the medial side of the face complex. FIG. 54 shows the curved needle 16 advanced through the working channel again, adjacent to the first wire 4a, this time advancing the same or a different curved, flexible needle 16, towards the opposite side of the facet complex 12. FIG. 55 shows where a second straight flexible wire 4b is advanced through the second placement of a curved needle 16, this time on the medial side of the facet joint. The second sharp, flexible, straight wire 4b is threaded through this second curved needle, and subsequently, advanced posteriorly, until the sharp tip of the wire 4b exits the skin 70. FIG. 56 next shows both the curved needles and the double lumen apparatus removed, leaving the wires 4a and 4b in place.

Figures 57, 58:
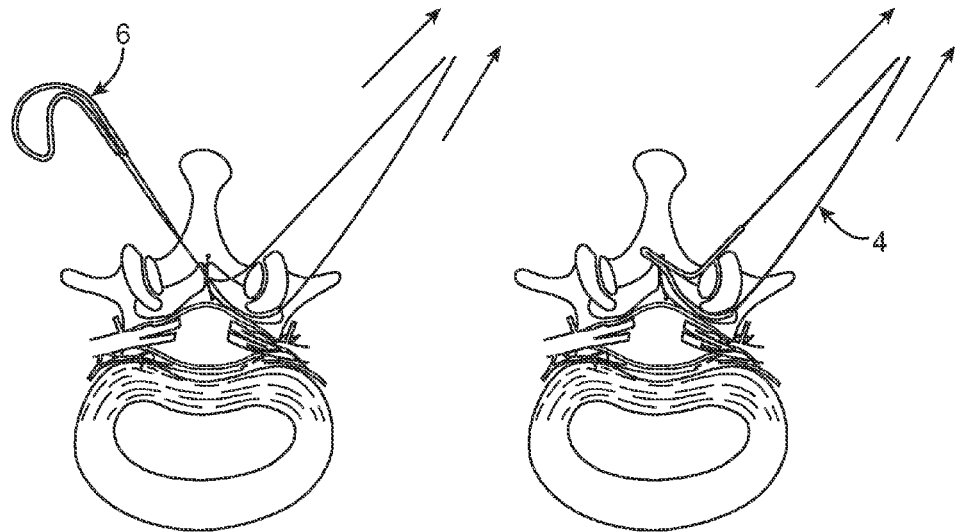

FIG. 57 shows that both wires have been attached to the two ends of the abrasive element 14 and/or the cover 6 of the abrasive element. With access established, via either a percutaneous or an open approach (or a combination thereof), neural protection and/or tissue removal elements may be introduced via the access for safe, selective removal of tissue. It should be understood that the methods and apparatus described hereinafter are equally applicable to both open and percutaneous approaches. For the purpose of clarity, they may be illustrated utilizing only a percutaneous or open access, but this should in no way be construed as limiting.

In order to reduce a risk of neurological damage during selective tissue removal, variations of the present invention optionally may provide neural protection during tissue removal. In one variation, a neural protection element, such as a sheath, shield or backstop, is positioned such that the neural protection element separates impinging tissue in the neural foramen from the underlying nerve root. Tissue removal then may proceed by advancing a tissue removal device into position between the foramen and the neural protection element. When access to the stenosed region is via an open surgical procedure, it may be possible for the medical practitioner to manually place the neural protection element Alternatively, when using either an open or a percutaneous access, the neural protection element may by advanced over, or pulled into place by, an access guide wire placed as described previously.

Neural protection element 6 illustratively comprises a sheath having opening or window that is placed across the foramen at the position of desired selective tissue removal. The end regions of neural protection element 6 disposed outside the patient optionally may be attached or clipped together to stabilize the element and free up the medical practitioner's hands.

Figures 59, 60:
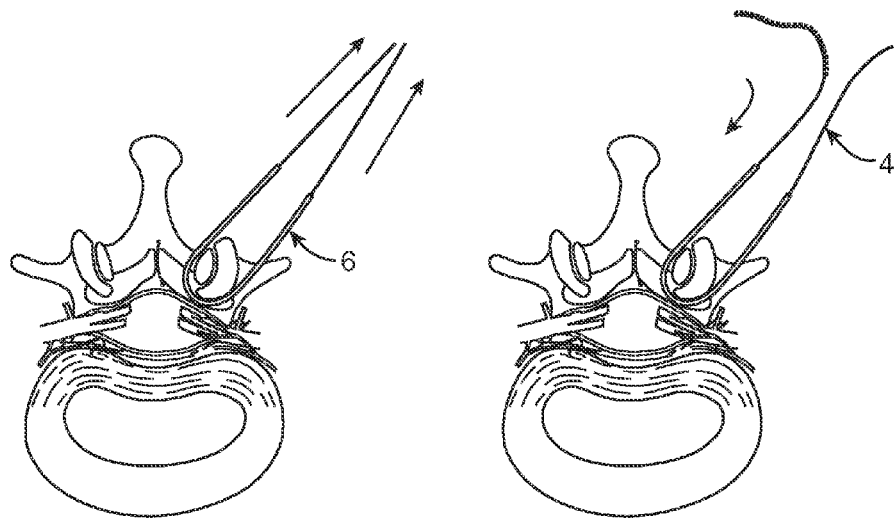
Figures 61, 62:
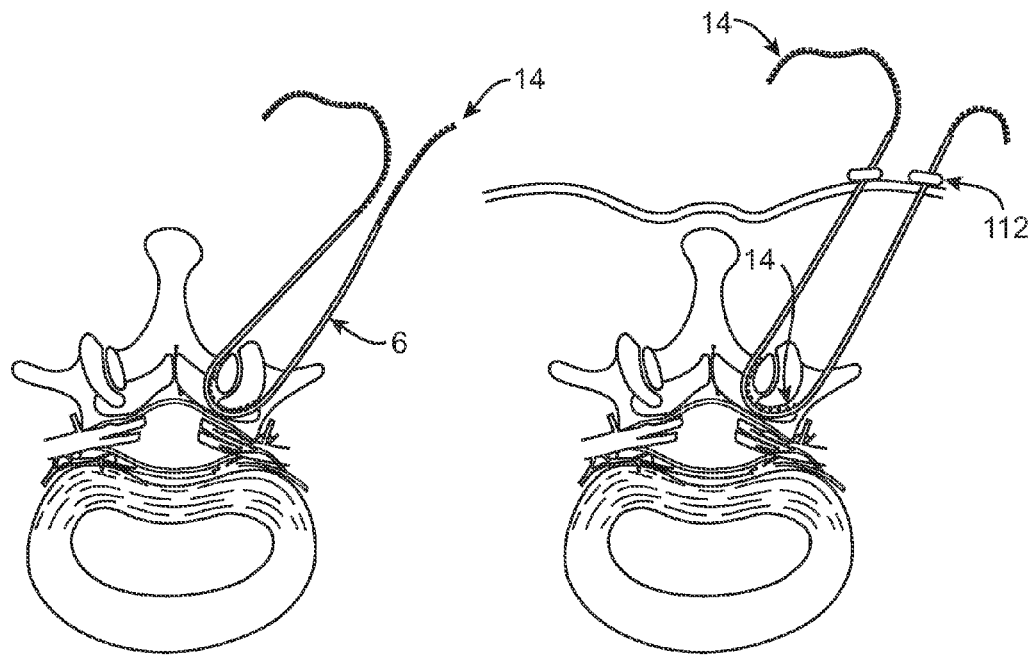
FIG. 62 is a cross-sectional view through a patients spine, illustrating a methods and apparatus that, under tension, anchors and suspends the working sheath or protective sleeve that covers the neuroforaminal abrasion device.

As illustrated in FIGS. 57-63, a tissue removal device may be positioned between impinging tissue and the neural protection element for safe, selective removal of the impinging tissue. For example, tissue removal device 14 may be delivered through, along or in conjunction with neural protection element 6 to position the tissue removal device across the foramen between the impinging tissue and the neural protection element with tissue removal surface of device locally exposed to the impinging tissue within window of neural protection element 6. In FIG. 60, tissue removal device 14 is coupled to access guide wire 4. In FIG. 61, the tissue removal device is pulled into position by partially or completely removing the guide wire. Tissue removal device 14 alternatively may be positioned across the neural foramen in conjunction with, or at the same time as, neural protection element 6, which optionally may be coupled to guide wire 4 and pulled into position. Furthermore, neural protection element 6 and tissue removal device 14 may be integrated into a single device. As yet another alternative, tissue removal device may be advanced over guide wire 4.

Figure 63:
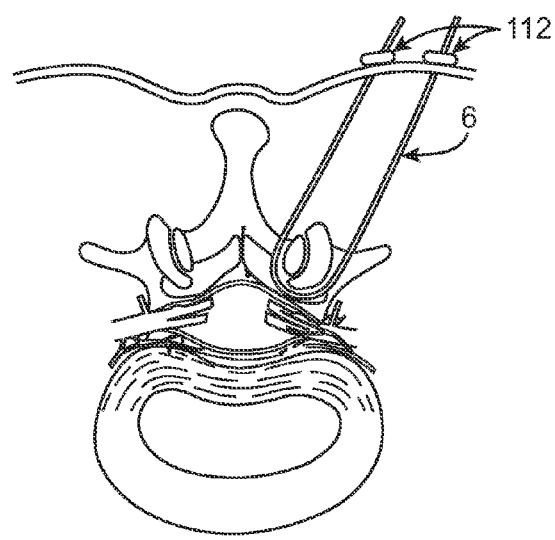
FIG. 63 is a cross-sectional view through a patient's spine, illustrating a method and apparatus that, under tension, provides a percutaneous compression dressing over the abraded area. In this illustration, the compression dressing is the same working sheath or protective sleeve that had covered the neuroforaminal abrasion device.

In FIGS. 62 and 63, temporary stops 112 have been attached to neural protection element 6 to maintain the position of the element and free up the medical practitioner's hands, for example, for manipulation of tissue removal device 14. The stops may hold window of sheath 6 of element 14 under tension against the impinging tissue. Stops 112 may be placed or expanded, or removed or collapsed, etc., at any time as desired; for example, the stops may be placed prior to positioning of tissue removal device 14 transforaminally. Stops 112 may comprise any element that temporarily maintains the position of the access element/guide wire, the neural protection element and/or the tissue removal device during a selective tissue removal procedure. As mentioned previously, the end regions of neural protection element 6 alternatively or additionally may be attached or clipped to one another to stabilize the element and free up the medical practitioner's hands.

As an added safety precaution, variations of the present invention optionally may comprise neural localization elements to ensure proper positioning of the access element or guide wire, the neural protection element, and/or the tissue removal device. The neural localization elements may comprise separate elements or may be integrated with the access element, the neural protection element and/or the tissue removal device.

Alternatively, the two wires 4a and 4b may be opposite ends of the same continuous wire, with the cover 6 for the abrasive element 14 already placed over the mid-portion of the wire 4. Alternatively, the abrasive element 14 may already have been placed inside said cover 6, and attached at each end to the wires 4a and 4b. FIGS. 58 and 59 show the two wires 4a and 4b pulled and bringing the abrasive element cover, possibly with the abrasive element 14 already placed inside said cover 6, into position through the neural foramina. FIG. 60 illustrates the step that follows placement of the abrasion element cover 6 alone. In FIG. 60, with the wire 4 in place inside the abrasion element cover 6, the abrasive element 14 is now seen to have been attached to the end of the wire. Subsequently, the cover 6 is held open at each end by a grasping device, which also holds the cover 6 under tension against the tissue to be abraded. With the cover anchored thus, the abrasive element 14 is pulled into place by the wire 4a/b, replacing the wire, as has occurred for FIGS. 61 and 62. With the abrasive element in position and the abrasive element cover 6 tightly held open and against the tissue to be abraded, the abrasion element 14 may be pulled back and forth, under tension, against the tissue to be abraded, as in FIG. 62. Alternatively, the abrasive element may be pulled in a single direction across the tissue to be abraded. FIG. 63 illustrates the cover 6 following removal of the abrasive element. Said cover may remain in placed as a compression bandage, under tension against the freshly abraded surface, in order to promote hemostasis, promote tissue remodeling, and trap debris post operatively.

Figure 64:
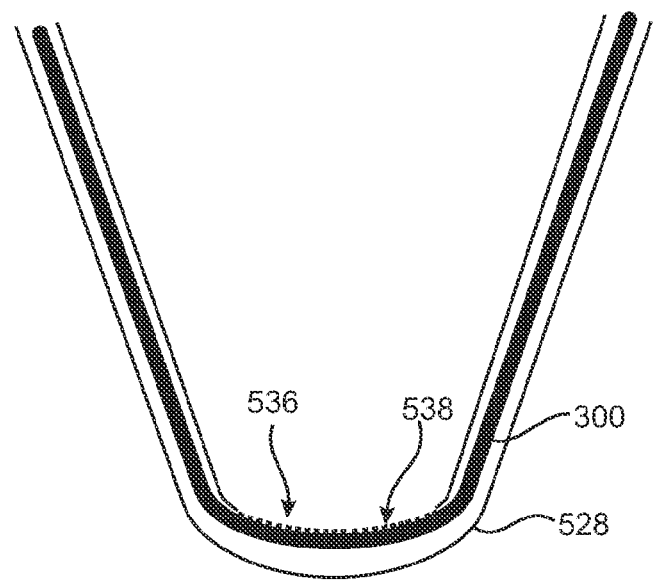
FIG. 64 is a cross-sectional view of an embodiment of the tissue removal apparatus.

FIG. 64 illustrates that the tissue removal apparatus can have the tissue removal device 300 and the tissue protection barrier 528. The tissue removal device 300 can be slidably attached to an inside conduit, channel or hollow of the tissue protection barrier 528. The tissue removal device 300 can have the working surface 538. The working surface 538 can be configured to damage, and/or destroy, and/or remove the impinging tissue. Part or all of the working surface 538 can be exposed through the window 536. The window 536 can be on the front side of the tissue protection barrier 528. The tissue barrier protection 528 can have and/or elute a lubricious coating or material, for example on the surface of the inside conduit, channel or hollow. The tissue removal device 300 can have and/or elute a lubricious coating or material on the entire surface and/or on the surface other than on the working surface 538.

Figure 65:
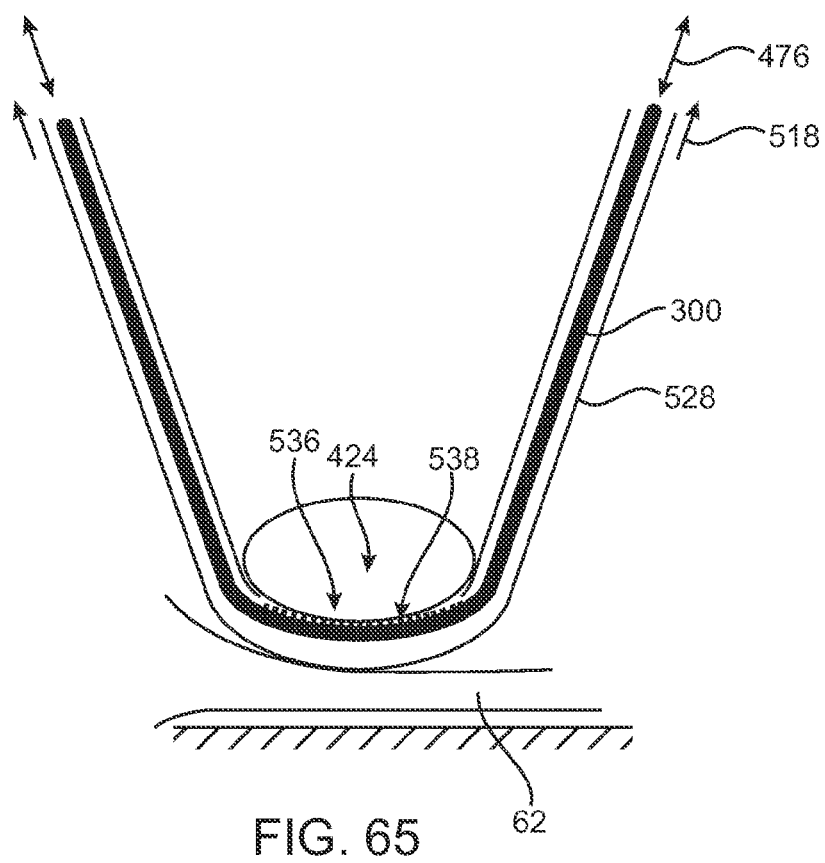
FIG. 65 is a cross-sectional view of an embodiment of a method for using the tissue removal apparatus.

FIG. 65 illustrates that a method of using the tissue removal apparatus 538 can include deploying the window adjacent to the impinging tissue 424. A tension, as shown by arrows 518, can be applied to the tissue protection barrier 528. The tissue removal device 300 can be reciprocated or oscillated, as shown by arrows 476. The oscillation can, for example, result in the working surface 538 to separate impinging tissue 424. The separated impinging tissue 424 can be removed, for example by suction, through the tissue protection barrier 528 and/or the tissue removal device 300. Section D can be equivalent to sections A, B, or C.

The working surface 538 can have one or more non-powered mechanical tissue removal elements. The non-powered mechanical tissue removal elements can be abrasives such as abrasive belts or ribbons, cutting elements such as blades, knives, scissors or saws, rongeurs, grinders, files, debriders, scrapers, graters, forks, picks, burrs, rasps, shavers, or combinations thereof.

The mechanical tissue removal elements can be used in combination or not in combination with the energy delivery device. The mechanical tissue removal elements can be pushed into and/or drawn across the impinging tissue 424 to remove the tissue by cutting, shaving, slicing, scissoring, guillotining, scraping, tearing, abrading, debriding, poking, mutilating, or combinations thereof. The mechanical tissue removal elements (e.g., blades) can be drawn across the impinging tissue 424 in a single direction and/or can be reciprocated. The mechanical tissue removal elements can be manually controlled and/or electronically, pneumatically or hydraulically powered. The mechanical tissue removal elements can be embedded with abrasives and/or have abrasive coatings, such as a diamond or oxide coating.

The blades can have various shapes, sizes and configurations. The blades can coact, for example, in a guillotine-type or scissor-type cutting action. The blades can be attached to or integral with the tissue removal device. The blades can be formed by grinding, punching or stamping through the tissue removal device. The blades can be formed by grinding of a punched or stamped edge of the tissue removal device. The blades can be formed by a chemical etching process. The blades can have a 3-dimensional profile to facilitate cutting, for example, a bow or a corrugation or a 'cheese grater' profile. The blades can be placed at one or more angles relative to the direction of tissue removal. The blades can be configured with the blade cutting across the tissue (i.e., similar to a band saw). The blades can have cutting surfaces. The cutting surfaces can be oriented in a single or multiple directions. The blades can be serrated.

The saw can be a wire saw or saws. The wire saw can be a Gigli saw. Multiple wire saws or Gigli saws can be joined or woven together or flattened to form a substantially planar cutting surface. The wire saw can be mounted on a flat ribbon. The ribbon can be a depth stop, for example, limiting for saw penetration.

The tissue removal device 300 can have one or more powered mechanical tissue removal elements. The powered mechanical tissue removal elements can have, for example, band saws, belt shavers, rotary burrs or blades, reciprocating burrs or blades, or combinations thereof.

Devices and elements known to those having ordinary skill in the art can be used to remove debris from, and/or irrigate, and/or provide suction to, the epidural space 42 including the lateral recess 108 and neural foramen 110 and/or to the tissue removal device itself. The devices and elements for removing debris can be integral with the needle 464 and/or the catheter 24. Debris removal, and/or suction and/or irrigation may be provided intermittently or continuously, as desired by the medical practitioner. Debris removal can include suction and/or irrigation. The tissue removal device 300 can capture debris. Irrigation and/or suction in the tissue removal device 300 can remove the debris from the tissue removal device 300, for example by the debris exiting along the needle 464 and/or catheter 24.

Figure 66A:
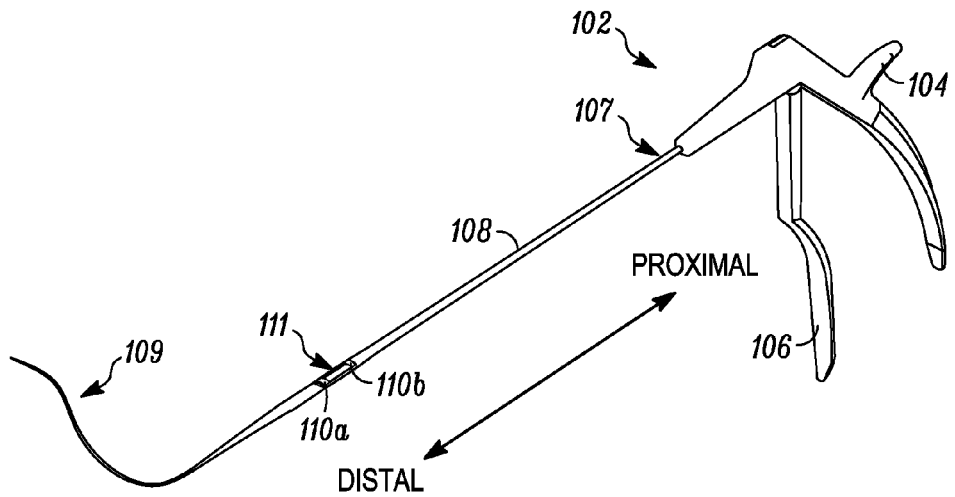
FIG. 66A is a perspective view of a tissue modification device according to one embodiment of the present invention.

Turning now to FIG. 66A-66I, more detailed figures of one embodiment of tissue modification device 102 are shown. Referring to FIG. 66A, tissue modification device 102 may include elongate body 108 having proximal portion 107 and distal portion 109, a window 111 disposed along elongate body 108, two tissue modifying blades 110 exposed through window 111, and handle 104 with actuator 106 coupled with proximal portion 107. In the embodiment shown, the tissue modifying members comprise blades 110, although in alternative embodiments other tissue modifying members may be added or substituted.

In various embodiments, elongate body 108 may have any number of dimensions, shapes, profiles and amounts of flexibility. For example, distal portion 109 is shown having a curved shape to demonstrate that at least a portion of elongate body 108 may be flexible. In various embodiments, elongate body 108 may have one or more of a round, ovoid, ellipsoid, flat, cambered flat, rectangular, square, triangular, symmetric or asymmetric cross-sectional shape. As shown in FIGS. 66C and 66D, in the pictured embodiment, elongate body 108 has a relatively flat configuration, which may facilitate placement of body 108 between target and non-target tissues. Distal portion 109 of body 108 may be tapered, to facilitate its passage into or through narrow spaces as well as through small incisions on a patient's skin. Body 108 may also include a slightly widened portion around the area of window 111 and blades. In one embodiment, such as an embodiment used for modifying tissue in a spine, body 108 may have a small profile, such as having a height of not more than 10 mm at any point along its length and a width of not more than 20 mm at any point along its length, or more preferably a height not more than 5 mm at any point along its length and a width of not more than 10 mm at any point along its length, or even more preferably a height not more than 2 mm at any point along its length and a width of not more than 4 mm at any point along its length. Body 108 may be long enough to extend through a first incision on a patient, between target and non-target tissue, and out a second incision on a patient. Alternatively, body 108 may be long enough to extend through a first incision, between the target and non-target tissue, and to an anchoring location within the patient. In another alternative embodiment, body 108 may be long enough to extend through a first incision, between the target and non-target tissue, to a location nearby but distal to the target tissue within the patient, with some portion of tissue modification device 102 anchored to guide member 116. In some embodiments, elongate body 108 includes at least one feature for allowing passage of the body over a guidewire or other guide member or to allow passage of one or more guide members over or through body 108. For example, in various embodiments body 108 may include one or more guidewire lumens, rails, tracks, lengthwise impressions or some combination thereof.

In one embodiment, elongate body 108 is predominantly flexible along its length and comprises any suitable flexible material, such as thin, flexible metals, plastics, fabrics or the like. In some embodiments, it may be advantageous to include one or more rigid sections in elongate body 108, such as to impart pushability to a portion of body 108 or to facilitate application of force to tissue modification members 110 without causing unwanted bending or kinking of elongate body 108. In such embodiments, rigidity may be conferred by using additional materials in body 108 or by making the rigid portions thicker or wider or of a different shape.

Handle 104 may have any suitable configuration according to various embodiments. Similarly, actuator 106 may include any of a number of actuation devices in various embodiments. In the embodiment shown in FIG. 66A, actuator 106 comprises a trigger or moving handle portion, which is grasped by a user and pulled or squeezed toward handle 104 to bring blades 110 together to cut tissue. In an alternative embodiment, actuator 106 instead may include a switch or button for activating a radiofrequency surgical ablation tissue modifying member. In yet another embodiment, actuator 106 may include a combination trigger and switch, one or more pull wires, any suitable form of lever and/or some combination thereof.

Figure 66B:
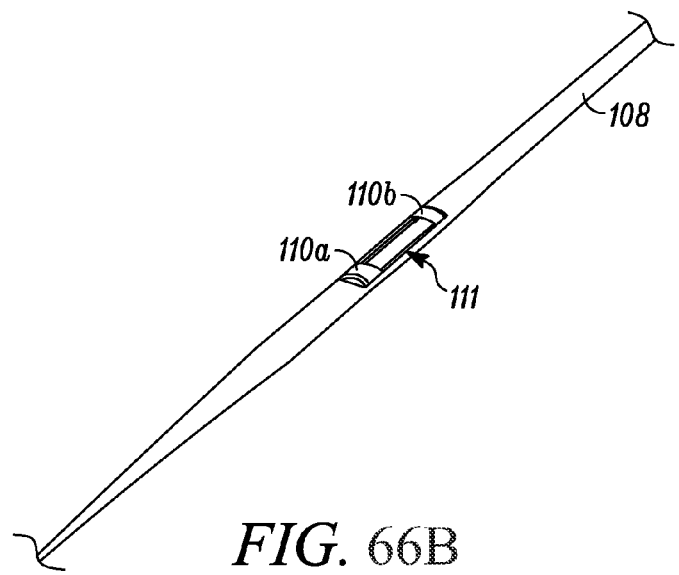
FIG. 66B is a perspective view of a portion of the tissue modification device of FIG. 66A.
Figure 66C:
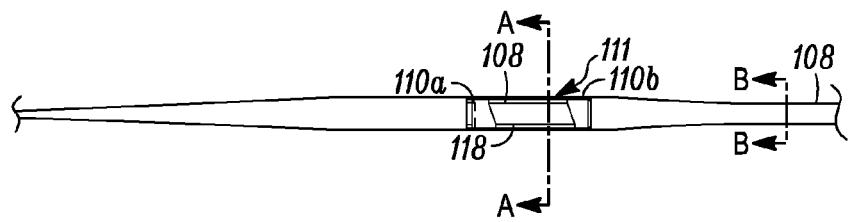
FIG. 66C is a top view of the portion shown in FIG. 66B.
Figure 66D:
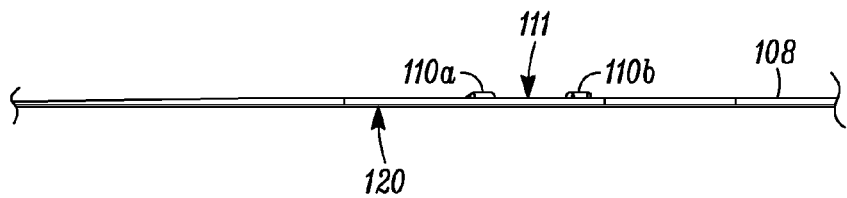
FIG. 66D is a side view of the portion shown in FIGS. 66B and 66C.

FIGS. 66B-66D show in greater detail a portion of tissue modification device 102. In these figures, window 111 and blades 110 are more clearly seen. In one embodiment, at least a portion of elongate body 108 and blades 110 may have a slightly curved configuration. In alternative embodiments, at least a portion of elongate body 108 and blades 110 may be flat. In other alternative embodiments, tissue modification members such as blades 110 may be proud to elongate body 108.

Blades 110 include a distal 110a and a proximal blade 110b that reside at the distal and proximal edges, respectively, of window 111 of elongate body 108. Window 111 of body 108 may accommodate both soft and hard tissue when the device is forcibly applied to the surface of a target tissue site. The top view of the distal portion of elongate body 108, shown in FIG. 66C, depicts the angled edges of distal blade 110a and proximal blade 110b, which facilitate shearing of target tissue. In alternative embodiments, blades 110 may have any of a number of alternative shapes and configurations. The distal portion of body 108 may have a very low profile (height compared to width), as shown in side view FIG. 66D, where only blades 110 protrude from the top surface of the elongate body 108. In one embodiment, also as shown in FIG. 66D, a guidewire tube 120 (or lumen) may extend from (or be coupled with) a lower surface of elongate body 108. The lower surface of elongate body 108 is an example of a protective or non-tissue-modifying surface.

Figure 66E:
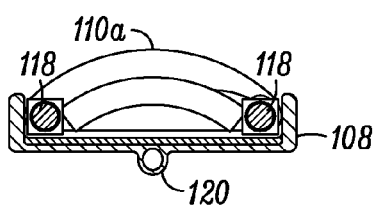
FIGS. 66E and 66F are cross-sectional views of a portion of the tissue modification device taken through lines A-A and B-B, respectively, shown in FIG. 66C.
Figure 66F:
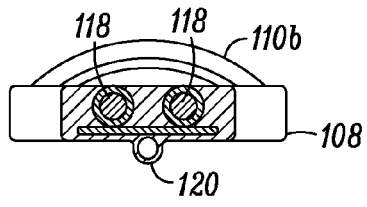

In one embodiment, distal blade 110a is coupled with two pull-wires 118, as seen in FIGS. 66C, 66E and 66F. Pull-wires 118 coupled to and translated by actuator 106 on handle 104 may be used to drive distal blade 110a proximally to contact the cutting edge of proximal blade 110b, thus cutting tissue. Other alternative mechanisms for driving blades 110, such as gears, ribbons or belts, magnets, electrically powered, shape memory alloy, electro magnetic solenoids and/or the like, coupled to suitable actuators, may be used in alternative embodiments. As mentioned, in one embodiment distal blade 110a and/or proximal blade 110b may have an outwardly curvilinear shape along its cutting edge. Alternatively, distal blade 110a may have a different blade shape, including flat, rectilinear, v-shaped, and inwardly curvilinear (concave vs. convex). The cutting edge of either blade 110 may have a sharp edge formed by a simple bevel or chamfer. Alternatively or in addition, a cutting edge may have tooth-like elements that interlock with a cutting edge of an opposing blade, or may have corrugated ridges, serrations, rasp-like features, or the like. In various embodiments, both blades 110 may be of equal sharpness, or alternatively one blade 110 may be sharp and the other substantially flat to provide a surface against which the sharp blade 110 may cut. Alternately or in addition, both cutting edges may be equally hard, or a first cutting edge may be harder than a second, the latter of which deflects under force from the first harder edge to facilitate shearing of the target tissue.

FIGS. 66E and 66F show cross-sectional views through elongate body at lines A-A and B-B, respectively, of FIG. 66C. In some embodiments, all or a portion of elongate body 108, such as the lower surface shown in FIG. 66E, may include a lubricious surface for facilitating manipulation of the tool in the surgical space and at the anatomical site. The lubricious lower surface also provides a barrier between blades 110 and non-target tissue in the surgical space. The lower surface may include a guide member lumen 120 to accommodate a guidewire or other access device or rail. FIG. 66E shows distal blade 110 coupled with pull wires 118. FIG. 66F shows proximal blade 110b, which is not coupled with pull wires 118 but rather fixed to body 108. In various alternative embodiments, proximal blade 110b may be movable distally while distal blade 110a is static, both blades may be moved toward one another, or a different number of blades may be used, such as one blade drawn toward a backstop or more than two blades, one or more of which may be mobile. In various alternative embodiments, guide member lumen 120 may be accommodated on a side surface or more centrally within elongate body 108. In further alternative embodiments, the one or more guide member lumens 120 may comprise one or more various cross sectional shapes, for example substantially round, substantially oval, or substantially rectabular, to accommodate alternative guide members, for example flat or rectangular guidewires, needles or rails. In still other alternative embodiments guide member lumen 120 may be adjustably coupled with the elongate body 108 to enable manipulation of the location of the elongate body 108 and therefore the tissue modifying members 110 relative to the guiding member.

Figure 66G:
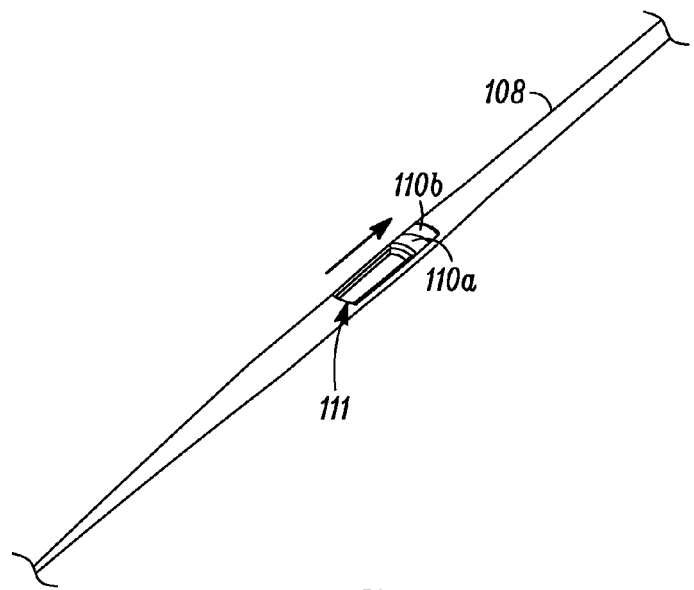
FIG. 66G is a perspective view of a portion of the tissue modification device of FIGS. 66B-66F, shown with a blade of the device in a closed position according to one embodiment of the present invention.
Figure 66H:
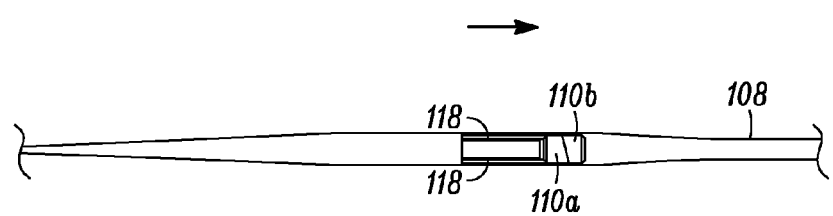
FIG. 66H is a top view of the portion shown in FIG. 66G.
Figure 66I:
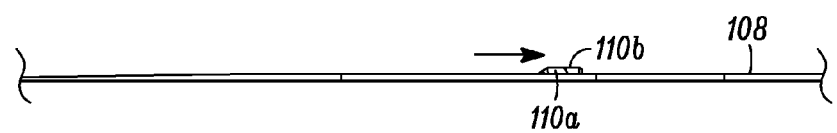
FIG. 66I is a side view of the portion shown in FIGS. 66G and 66H.

Referring now to FIGS. 66G-66I, blades 110 are shown in their closed position. In one embodiment, when distal blade 110a is drawn proximally to cut tissue, at least some of the cut tissue is captured in a hollow interior portion of elongate body 108. Various embodiments may further include a cover, a cut tissue housing portion and/or the like for collecting cut tissue and/or other tissue debris. Such collected tissue and debris may then be removed from the patient during or after a tissue modification procedure. During a given tissue modification procedure, distal blade 110a may be drawn proximally to cut tissue, allowed to retract distally, and drawn proximally again to further cut tissue as many times as desired to achieve a desired amount of tissue cutting.

Blades 110 may be made from any suitable metal, polymer, ceramic, or combination thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill. USA), Conichrome® (Carpenter Technology, Reading, Pa., USA), or Phynox® (Imphy SA, Paris, France). In some embodiments, materials for the blades or for portions or coatings of the blades may be chosen for their electrically conductive or thermally resistive properties. Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stuffiness. Ceramics may include but are not limited to aluminas, zirconias, and carbides. In various embodiments, blades 110 may be manufactured using metal injection molding (MIM), CNC machining, injection molding, grinding and/or the like. Pull wires 118 be made from metal or polymer and may have circular, oval, rectangular, square or braided cross-sections. In some embodiments, a diameter of a pull wire 118 may range from about 0.00"-0.050", and more preferably from about 0.010"-0.020".

Depending on the tissue to be treated or modified, activating blades 110 (or other tissue modifying members in alternative embodiments) may cause them to modify target tissue along an area having any of a number of suitable lengths. In use, it may also be advantageous to limit the extent of action of blades 110 or other tissue modifying members to a desired length of tissue, thus not allowing blades 110 to affect tissue beyond that length. In so limiting the effect of blades, unwanted modification of or damage to, surrounding tissues and structures may be limited or even eliminated. In one embodiment, for example, where the tissue modification device is used to modify tissue in a spine, blades 110 may operate along a length of target tissue of no more than 10 cm, and preferably no more than 6 cm, and even more preferably no more than 3 cm. Of course, in other parts of the body and to address other tissues, different tissue modification devices may be used and tissue modifying members may have many different lengths of activity. In one embodiment, to facilitate proper location of tissue modifying members, such as blades 110, relative to target tissue, the tissue modifying members and/or the elongate body and/or one or more additional features intended for just such a purpose may be composed of a material readily identifiable via x-ray, fluoroscopic, magnetic resonance or ultrasound imaging techniques.

In various embodiments, a number of different techniques may be used to prevent blades 110 (or other tissue modifying members) from extending significantly beyond the target tissue. In one embodiment, for example, preventing blades 110 from extending significantly beyond the target tissue involves holding tissue modification device 102 as a whole predominantly stable to prevent device 102 from translating in a direction toward its proximal portion or toward its distal portion white activating blades 110. Holding device 102 stable is achieved by anchoring one end of the device and applying tensioning force at or near the other end, as described further below.

In the embodiment shown in FIGS. 66A-66I, pull wires 118 are retracted proximally by squeezing actuator 106 proximally. In an alternative embodiment, squeezing actuator 106 may cause both blades 110 to translate inward so that they meet approximately in the middle of window 111. In a further embodiment, distal blade 110a may be returned to it's starting position by a pulling force generated from the distal end of device 102, for example by using a distal actuator that is attached to distal wires, or by pulling on the distal guide member which is attached to distal blade 110a. In yet another alternative embodiment, proximal blade 110b may be moved to cut by a pulling force generated from the distal end of device 102, for example by using a distal actuator that is attached to distal wires, or by pulling on the distal guide member which is attached to proximal blade 110b. In yet another embodiment, squeezing actuator 106 my cause proximal blade 110b to move distally while distal blade 110a stays fixed. In other alternative embodiments, one or more blades 110 may move side-to-side, one or more blades 110 may pop, slide or bow up out of window 111 when activated, or one or more blades 110 may expand through window. In another embodiment, one or more blades 110 and/or other tissue modifying members of device 102 may be powered devices configured to cut, shave, grind, abrade and/or resect target tissue. In other embodiments, one or more blades may be coupled with an energy transmission device, such as a radiofrequency (RF) or thermal resistive device, to provide energy to blade(s) 110 for cutting, ablating, shrinking, dissecting, coagulating or heating and thus enhancing tissue modification. In another embodiment, a rasp or file may be used in conjunction with or coupled with one or more blades. In any of these embodiments, use of actuator 106 and one or more moving blades 110 provides for tissue modification with relatively little overall translation or other movement of tissue modification device 102. Thus, target tissue may be modified without extending blades 110 or other tissue modification members significantly beyond an area of target tissue to be treated.

Figure 67A:
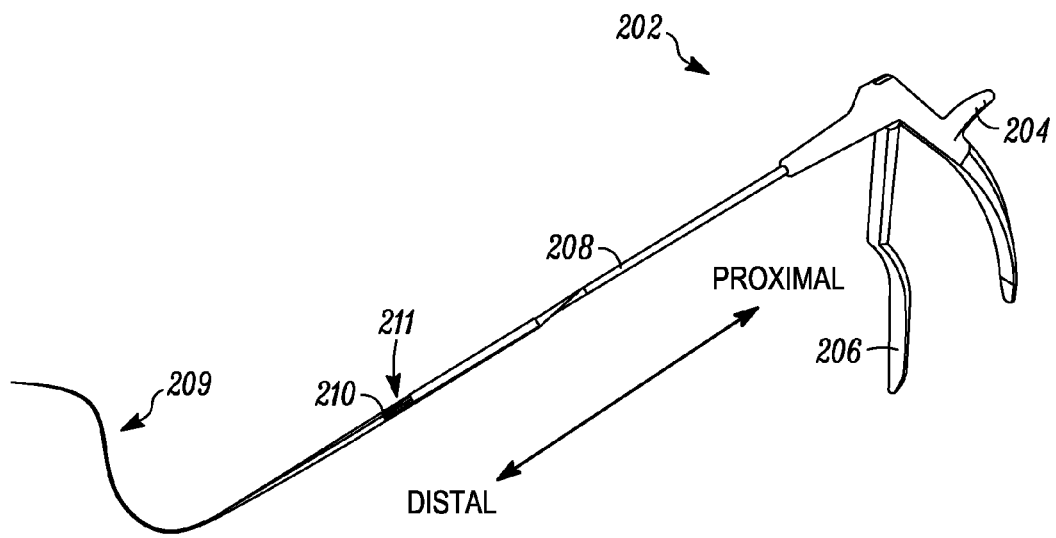
FIG. 67A is a perspective view of a tissue modification device according to one embodiment of the present invention.
Figure 67B:
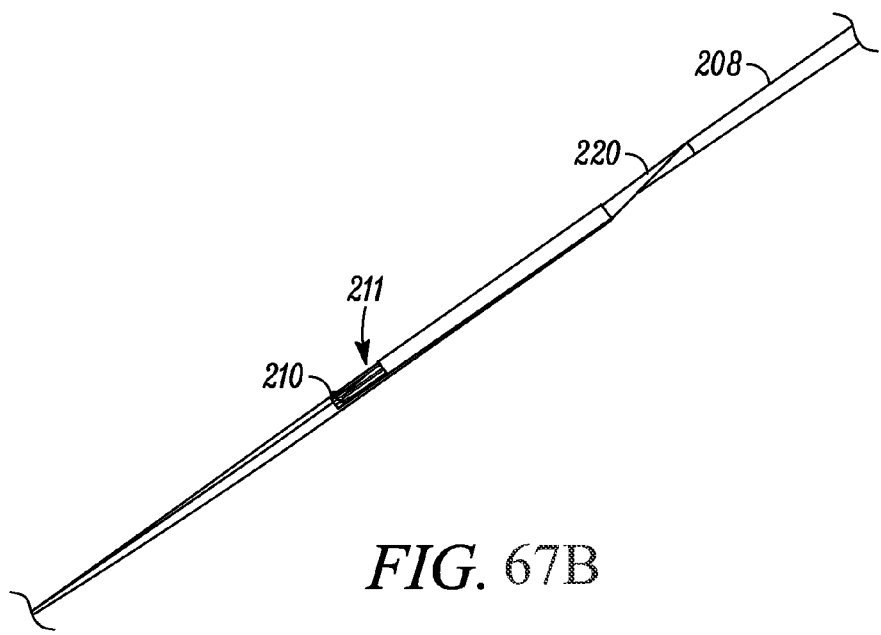
FIG. 67B is a perspective view of a portion of the tissue modification device of FIG. 4A.
Figure 67C:
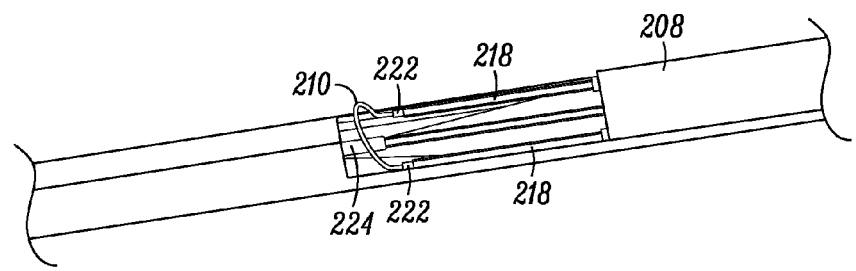
FIG. 67C is a close-up, perspective view of a portion of the tissue modification device of FIGS. 67A and 67B, showing a tissue modifying member according to one embodiment of the present invention.

Referring now to FIGS. 67A-67C, in an alternative embodiment, a tissue modification device 202 may include an elongate body 208 having a proximal portion and a distal portion 209, a handle 204 and actuator 206 coupled with proximal portion, and a window 211 and tissue modifying member 210 disposed near distal portion 209. As seen more clearly in FIGS. 4B and 4C, in the embodiment shown, tissue modifying member 210 comprises an RF electrode wire loop. Wire loop 210 may comprise any suitable RF electrode, such as those commonly used and known in the electrosurgical arts, and may be powered by an internal or external RF generator, such as the RF generators provided by Gyrus Medical, Inc. (Maple Grove, Minn.). Any of a number of different ranges of radio frequency may be used, according to various embodiments. For example, some embodiments may use RF energy in a range of between about 70 hertz and about 5 megahertz. In some embodiments, the power range for RF energy may be between about 0.5 Watts and about 200 Watts. Additionally, in various embodiments, RF current may be delivered directly into conductive tissue or may be delivered to a conductive medium, such as saline or Lactate Ringers solution, which may in some embodiments be heated or vaporized or converted to plasma that in turn modifies target tissue. Distal portion 209 includes a tapered tip, similar to that described above, to facilitate passage of elongate body 208 into narrow anatomical sites. Handle 204 and actuator 206 are similar to those described above, although in the embodiment of FIGS. 67A-67C, actuator 206 may be used to change the diameter of the wire loop 210. Using actuator 206, wire loop 210 may be caused to extend out of window 211, expand, retract, translate and/or the like. Some embodiments may optionally include a second actuator (not shown), such as a foot switch for activating an RF generator to delivery RF current to an electrode.

Elongate body 208 may be fabricated from any suitable material and have any of a number of configurations. In one embodiment, body 208 comprises a metal tube with a full-thickness slit (to unfold the tube into a flat form—not shown) or stiffening element (not shown). The split tube provides for a simple manufacturing process as well as a conductive pathway for bi-polar RF operation.

Referring to FIG. 67C, insulators 222 may be disposed around a portion of wire loop 210 so that only a desired portion of wire loop 210 may transfer RF current into the tissue for tissue modifying capability. Wire loop 210, covered with insulators 222 may extend proximally into support tubes 218. In various alternative embodiments, an electrode tissue modifying member (of which wire loop 210 is but one example) may be bipolar or monopolar. For example, as shown in FIG. 67C, a sleeve 224 housed toward the distal portion of window 211 may act as a return electrode for wire loop 210 in a bipolar device. Wire loop electrodes 210 may be made from various conductive metals such as stainless steel alloys, nickel titanium alloys, titanium alloys, tungsten alloys and the like. Insulators 222 may be made from a thermally and electrically stable polymer, such as polyimide, polyetheretherketone (PEEK), polytetrafluoroethylene (PTFE), polyamide-imide, or the like, and may optionally be fiber reinforced or contain a braid for additional stiffness and strength. In alternative embodiments, insulators 222 may be composed of a ceramic-based material.

In one embodiment, wire loop 210 may be housed within elongate body 208 during delivery of tissue modification device 202 into a patient, and then caused to extend up out of window 211, relative to the rest of body 208, to remove tissue. Wire loop 210 may also be flexible so that it may pop or bow up out of window 211 and may deflect when it encounters hard tissue surfaces. Wire loop 210 may have any of a number of shapes, such as curved, flat, spiral or ridged. Wire loop 210 may have a diameter similar to the width of body 208, while in alternative embodiments it may expand when extended out of window 211 to have a smaller or larger diameter than that of body 208. Pull wires (not shown) may be retracted proximally, in a manner similar to that described above, in order to collapse wire loop 210, decrease the diameter and lower the profile of the wire loop 210, and/or pull wire loop 210 proximally to remove tissue or be housed within body 208. The low profile of the collapsed wire loop 210, facilitates insertion and removal of tissue modification device 202 prior to and after tissue modification. As the wire loop 210 diameter is reduced, support tubes 218 deflect toward the center of elongate body 208.

In an alternative embodiment (not shown), tissue modification device 202 may include multiple RF wire loops 210 or other RF members. In another embodiment, device 202 may include one or more blades as well as RF wire loop 210. In such an embodiment, wire loop 210 may be used to remove or otherwise modify soft tissues, such as ligamentum flavum, or to provide hemostasis, and blades may be used to modify hard tissues, such as bone. In other embodiments, as described further below, two separate tissue modification devices (or more than two devices) may be used in one procedure to modify different types of tissue, enhance modification of one type of tissue or the like.

In other alternative embodiments, tissue modification devices 202 may include tissue modifying members such as a rongeur, a curette, a scalpel, a scissors, a forceps, a probe, a rasp, a file, an abrasive element, one or more small planes, a rotary powered mechanical shaver, a reciprocating powered mechanical shaver, a powered mechanical burr, a laser, an ultrasound crystal a cryogenic probe, a pressurized water jet, a drug dispensing element, a needle, a needle electrode, or some combination thereof. In some embodiments, for example, it may be advantageous to have one or more tissue modifying members that stabilize target tissue, such as by grasping the tissue or using tissue restraints such as barbs, hooks, compressive members or the like. In one embodiment, soft tissue may be stabilized by applying a contained, low-temperature substance (for example, in the cryo-range of temperatures) that hardens the tissue, thus facilitating resection of the tissue by a blade, rasp or other device. In another embodiment, one or more stiffening substances or members may be applied to tissue, such as bioabsorbable rods.

Figure 68A:
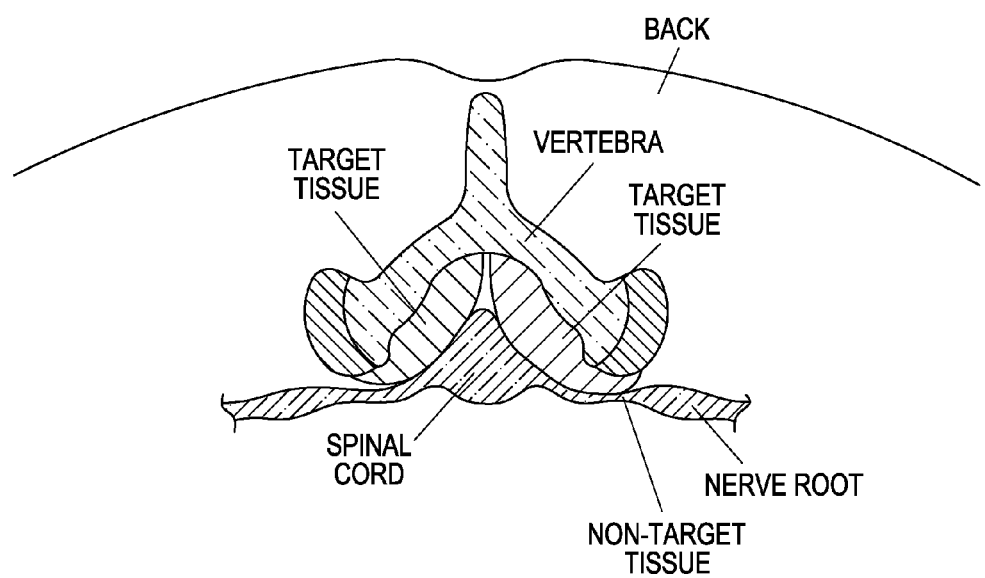
FIGS. 68A-68D are cross-sectional views of a spine and demonstrate a method for using a tissue modification device according to one embodiment of the present invention.

Referring now to FIGS. 68A-68D, one embodiment of a method for modifying tissue in a spine is demonstrated in simplified, diagrammatic, cross-sectional views of a portion of a patient's back and spine. FIG. 68A shows a portion of the patient's back in cross section, with a portion of a vertebra, the spinal cord with branching nerve roots, and target tissue, which in this illustration is the ligamentum flavum and possibly a portion of the facet capsule. The target tissue is typically impinging directly on one or more of the group including nerve roots, neurovascular structures, dorsal root ganglia, cauda equina, or individual nerves.

Figure 68B:
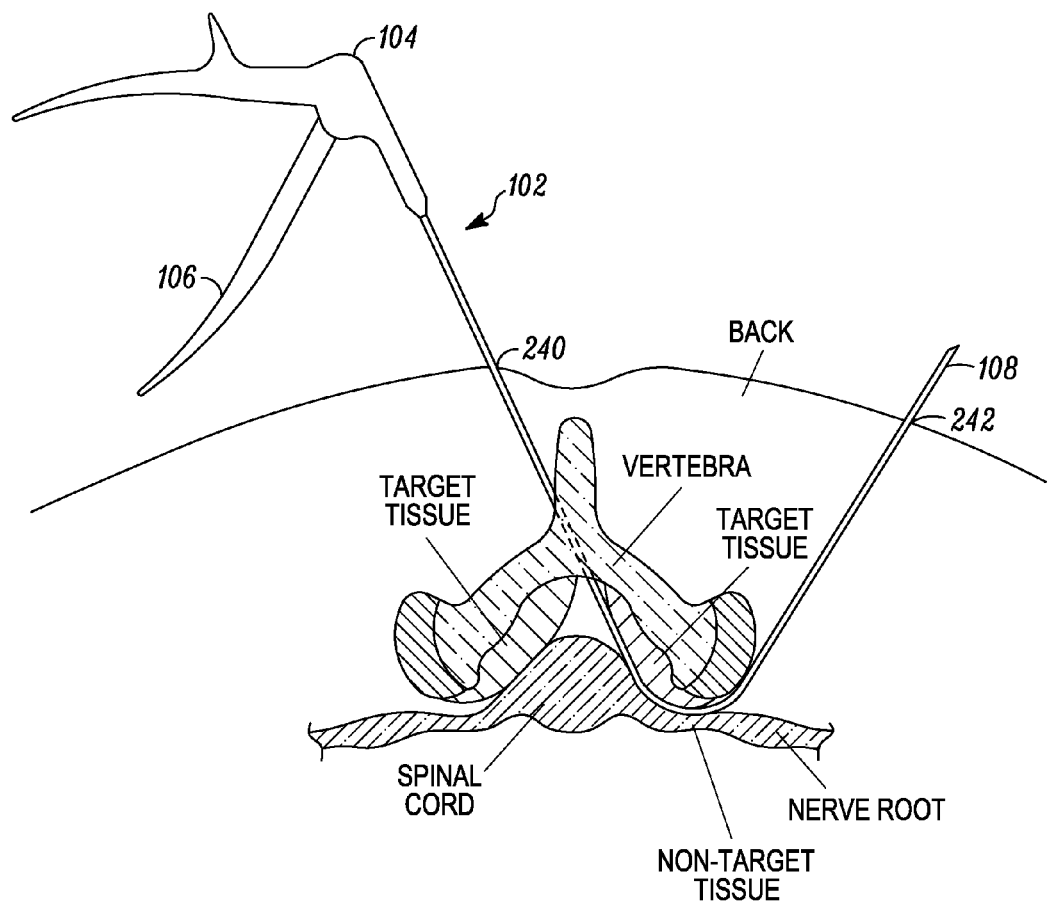

In FIG. 68B, tissue modification device 102 has been positioned in the patient's back to perform a tissue modification procedure. Various methods, devices and systems for introducing device 102 into the patient and advancing it to the position for modifying tissue are described in further detail below. Generally, device 102 my be positioned via a percutaneous Or open surgical procedure, according to various embodiments. In one embodiment, device 102 may be inserted into the patient through a first incision 240, advanced into the spine and between target tissue and non-target tissue (such as spinal cord, nerve roots, nerves and/or neurovascular tissue), and further advanced so a distal portion of elongate body 108 exits a second (or distal) incision 242 to reside outside the patient. In positioning device 102, one or more tissue modifying members (not shown) are positioned to face the target tissue, while one or more protective portions of elongate body 108 face non-target tissue.

Figure 68C:
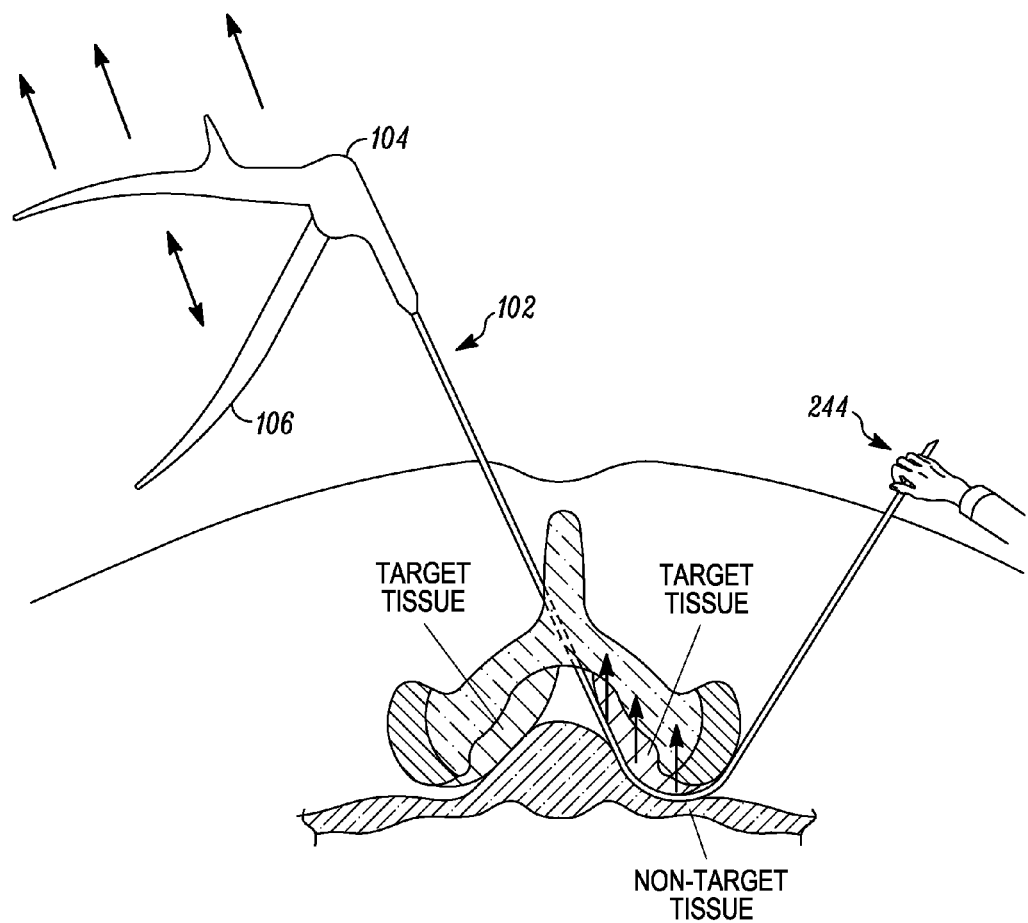

Referring to FIG. 68C, once device 102 is positioned in a desired location, anchoring force may be applied at or near the distal portion of elongate body 108. In one embodiment, applying anchoring force involves a user 244 grasping body 108 at or near its distal portion. In alternative embodiments, as described further below, anchoring force may be applied by deploying one or more anchor members disposed at or near the distal portion of body 108, or by grasping a guidewire or other guide member extending through at least part of body 108. Once the anchoring force is applied, proximally-directed tensioning force may be applied to device 102, such as by pulling proximally on handle 104 (one-directional, diagonal arrows). This tensioning force, when applied to the substantially anchored device 102, may help urge the tissue modifying member(s) against the target tissue (one-directional, vertical arrows near target tissue), thus enhancing contact with the target tissue and facilitating its modification. With the tissue modifying member(s) contacting the target tissue, actuator 106 may be squeezed or pulled (two-headed arrow) to cause the tissue modifying member(s) to modify tissue. (Alternative actuators may be activated in different ways in alternative embodiments.)

In various alternative embodiments, certain of the above-described steps may be carried out in different order. For example, in one embodiment the distal portion of elongate body 108 may be anchored within or outside the patient before the tissue modifying members are positioned adjacent the target tissue. In another alternative embodiment, the proximal portion of device 102 may be anchored, and the tensioning force may be applied to the distal portion of device 102. In yet another embodiment, tensioning force may be applied to both ends of the device. In yet another embodiment, a second handle and actuator may be coupled with the distal end of body 108 after it exits the patient's back, allowing tensioning forces as well as tissue modifying actuation to occur at both the proximal and distal portions of device 102. By anchoring one end of device 102 and applying tensioning force to the opposite end, contact of the tissue modifying members with the target tissue is enhanced, thus reducing or eliminating the need for translating or otherwise moving device 102 as a whole and reducing the overall profile and the resulting access pathway required to position the device. Reducing movement and profile of device 102 and using tissue modifying members confined to a relatively small area of device 102 helps facilitate target tissue modification while minimizing or eliminating damage to surrounding tissues or structures.

As mentioned above, tissue may be modified using one tissue modification device or multiple devices, according to various embodiments. In one embodiment, for example, an RF electrosurgical tissue modification device may be used in the patient to remove soft tissue such as ligament, and a bladed tissue modification device such as a rongeur may then be used to remove additional soft tissue, calcified soft tissue, or hard tissue such as bone. In some embodiments, such multiple devices may be inserted, used and removed serially, while in alternative embodiments such devices may be inserted into the patient at the same time to be used in combination.

Figure 68D:
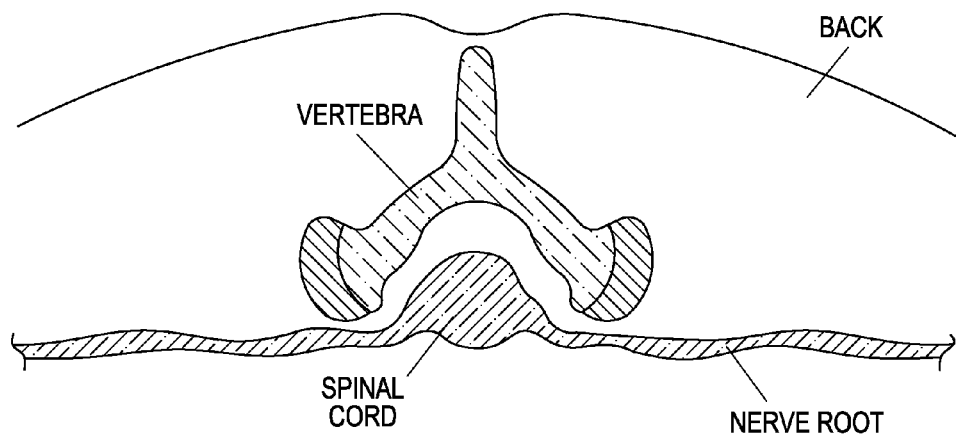

Referring to FIG. 68D, using one or more tissue modification devices 102, a desired amount of target tissue may be removed from more than one area in the spine. FIGS. 68A-68C demonstrate removal of target tissue on one side of the spine, and that method or a similar method may also be used to remove target tissue on an opposite side of the spine, as shown in FIG. 68D, where target tissue has been removed from both sides. That the desired amount of tissue has been removed may be confirmed by tactile feedback from the device or from a separate device, by testing nerve conduction through one or more previously impinged nerves, by testing blood flow through one or more previously impinged blood vessels, by passing (independently or over the guide member) a measurement probe or sound through the treated portion, through one or more radiographic tests, through some combination thereof, or by any other reasonable means.

Referring now to FIG. 69A, tissue modification device 102 is shown with one embodiment of a distal anchoring member 250 deployed at the patient's skin. In various embodiments, anchoring members may include but are not limited to one or more handles, barbs, hooks, screws, toggle bolts, needles, inflatable balloons, meshes, stents, wires, lassos, backstops or the like. In some embodiments, anchoring members 250 may be disposed at the extreme distal portion 109 of elongate body 108, while in other embodiments anchoring members 250 may be located more proximally. In the embodiment shown, anchoring members 250 are deployed at the patient's skin. In an alternative embodiment, anchoring may be achieved outside the patient by deploying one or more anchoring members 250 above the skin and having a user grasp the anchoring members 250. In an alternative embodiment, anchoring may be achieved outside the patient by deploying one or more anchoring members 250 above the skin and having a user grasp anchoring members 250, after tissue modification device 102 has been anchored to the guide member. In another alternative embodiment, anchoring may be achieved outside the patient by attaching anchoring member 250 to an external device, for example one that is mounted on the patient or on the procedure table. In a further alternative embodiment, anchoring may be achieved outside the patient by attaching the guide member to an external device, for example one that is mounted to on the patient or on the procedure table, after tissue modification device 102 has been anchored to the guide member. Anchoring members 250 generally are deployable from a first, contracted configuration to facilitate delivery of device 102, to a second, expanded configuration to facilitate anchoring. This change in configuration may be achieved, for example, by using shape memory or super-elastic materials, by spring loading anchoring members 250 into body 108 or the like. In most embodiments, anchoring members 250 may also be collapsed down into the first, contracted configuration after a tissue modification procedure has been performed, to facilitate withdrawal of device 102 from the patient. In an alternative embodiment, anchoring members 250 may detach from body 108 and may be easily removable from the patient's skin.

Figure 69B:
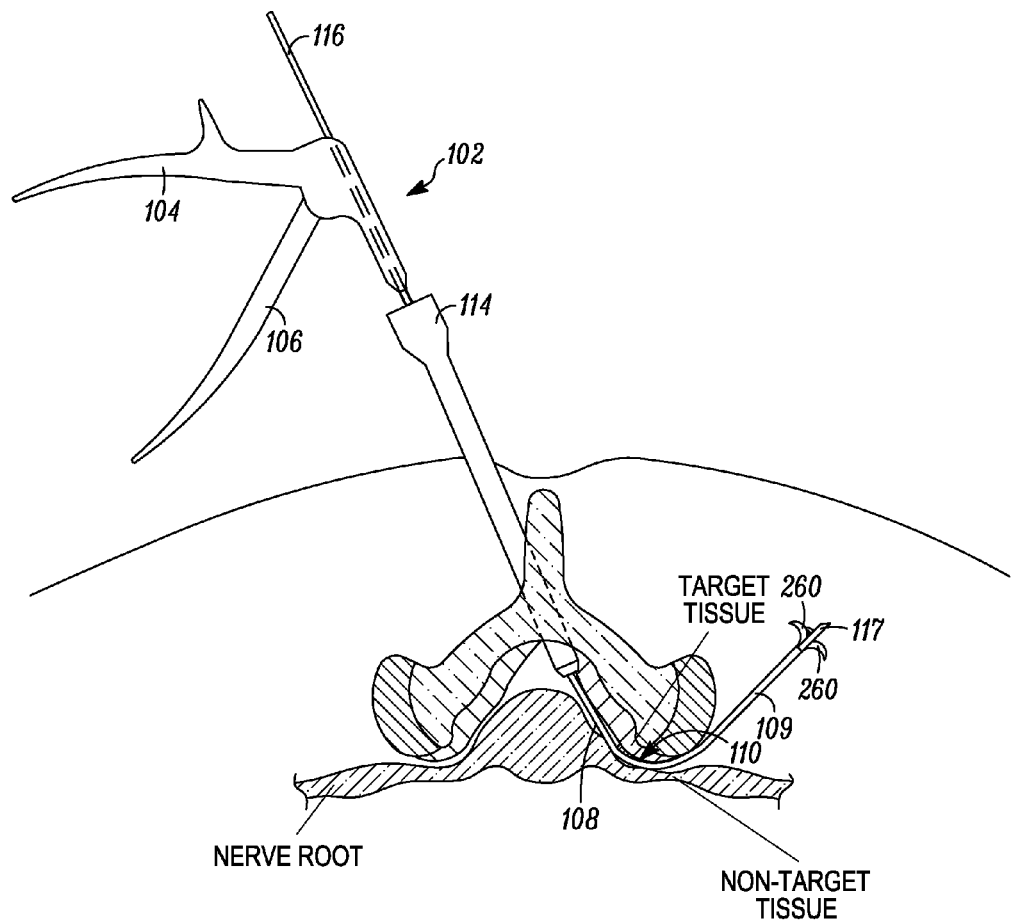
FIG. 69B is a cross-sectional view of a portion of a patient's spine and back, with apparatus for modifying tissue in position for modifying spinal tissue and with a distal portion of the apparatus anchored inside the patient according to one embodiment of the present invention.

FIG. 69B shows tissue modification device 102 with an alternative embodiment of a distal anchoring member 260.

Here, distal anchoring member 260 includes multiple hooks or barbs extended out the distal portion 109 of elongate body 108 within the patient's back. In using such an embodiment, it may not be necessary to pass guide member 117 through a second, distal incision on the patient, although in some embodiments guide member 117 may extend significantly beyond distal portion 109. Anchoring member(s) 260, according to various embodiments, may be deployed so as to anchor to bone, ligament, tendon, capsule, cartilage, muscle, or any other suitable tissue of the patient. They may be deployed into vertebral bone or other suitable tissue immediately adjacent an intervertebral foramen or at a location more distant from the intervertebral foramen. When a tissue modification procedure is complete, anchoring members 260 are retracted within elongate body for removal of device 102 from the patient.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

What is claimed is:

1. A method of performing a minimally invasive carpal tunnel release procedure to cut a target transverse carpal ligament, the method comprising:
    advancing a probe percutaneously through a patient's skin from a first location;
    advancing a tissue modification device from the first location and between the target ligament and non-target tissue so that a proximal handle on the tissue modification device extends from the patient at the first location, wherein the tissue modification device includes a flexible distal region having uni-directional blades, wherein the tissue modification device comprises an atraumatic cover forming an aperture through which the blades may engage the target ligament;
    attaching a distal handle in communication with the distal end of the tissue modification device, wherein the distal handle extends from the patient at a second location; and
    reciprocating the tissue modification device using the proximal handle and distal handles to incise the transverse carpal ligament with the uni-directional blades.

2. The method of claim 1, wherein reciprocating further comprises tensioning the tissue modification device to urge the blades towards the target ligament.

3. The method of claim 1, further comprising verifying correct device placement with a nerve stimulator.

4. The method of claim 3, further comprising attaching a nerve stimulator to a tissue modification device assembly.

5. A method of performing a minimally invasive carpal tunnel release procedure to cut a target transverse carpal ligament, the method comprising: advancing a tissue modification device through a small incision at a first location on a subject's skin and between the target ligament and non-target tissue so that a proximal handle on the tissue modification device extends from the patient at the first location, wherein the tissue modification device includes a flexible distal region having uni-directional blades, wherein the tissue modification device comprises an atraumatic cover forming an aperture through which the blades may engage the target ligament; attaching a distal handle in communication with the distal end of the tissue modification device, wherein the distal handle extends from the patient at a second location; and reciprocating the tissue modification device using the proximal handle and distal handles to incise the transverse carpal ligament with the uni-directional blades.

6. The method of claim 5, wherein reciprocating further comprises tensioning the tissue modification device to urge the blades towards the target ligament.

7. The method of claim 5, further comprising verifying correct device placement with a nerve stimulator.

8. The method of claim 7, further comprising attaching a nerve stimulator to a tissue modification device assembly.

9. A method for modifying a transverse carpal ligament in a patient, the method comprising: advancing a distal portion of an elongate tissue modification device into the patient's body and along a path between target and non-target tissues, such that a distal end of the distal portion exits the patient's body, wherein the tissue modification device comprises an atraumatic cover forming an aperture through which one or more tissue modifying members may engage the target ligament; applying a first force to a distal portion of the tissue modification device outside the patient; applying a second force to a proximal portion of the tissue modification device, the first and second forces urging one or more tissue modifying members of the tissue modification device against the target tissue; and reciprocating at least a portion of the tissue modification device back and forth to cause the one or more tissue modifying members to modify the target tissue.

10. The method of claim 9, wherein the target tissue is the transverse carpal ligament.

11. The method of claim 10, wherein reciprocating at least a portion of the tissue modification device back and forth causes the one or more tissue modifying members incise the transverse carpal ligament.

12. The method of claim 9, further comprising coupling a first handle with the distal portion of the tissue modification device outside the patient and applying the first force to the distal handle.

* * * * *